US008067100B2

(12) United States Patent
Walters et al.

(10) Patent No.: US 8,067,100 B2
(45) Date of Patent: *Nov. 29, 2011

(54) COMPLEXES WITH TRIDENTATE LIGANDS

(75) Inventors: Robert W. Walters, Export, PA (US); Jui-Yi Tsai, Newtown, PA (US); Peter Borden MacKenzie, Kingsport, TN (US); Scott Beers, Flemington, NJ (US)

(73) Assignee: Universal Display Corporation, Ewing, NJ (US)

( * ) Notice: Subject to any disclaimer, the term of this patent is extended or adjusted under 35 U.S.C. 154(b) by 114 days.

This patent is subject to a terminal disclaimer.

(21) Appl. No.: 12/240,584

(22) Filed: Sep. 29, 2008

(65) Prior Publication Data

US 2009/0115322 A1    May 7, 2009

(51) Int. Cl.
*H01J 1/63* (2006.01)
*C07F 15/00* (2006.01)

(52) U.S. Cl. ........ 428/690; 428/917; 313/504; 548/103; 546/4

(58) Field of Classification Search .................. None
See application file for complete search history.

(56) References Cited

U.S. PATENT DOCUMENTS

| 4,769,292 | A | 9/1988 | Tang et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,048,630 | A | 4/2000 | Burrows et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,310,360 | B1 | 10/2001 | Forrest et al. |
| 6,337,102 | B1 | 1/2002 | Forrest et al. |
| 6,383,666 | B1 | 5/2002 | Kim et al. |
| 6,420,057 | B1 | 7/2002 | Ueda et al. |
| 6,468,819 | B1 | 10/2002 | Kim et al. |
| 6,548,956 | B2 | 4/2003 | Forrest et al. |
| 6,576,134 | B1 | 6/2003 | Agner |
| 6,602,540 | B2 | 8/2003 | Gu et al. |
| 7,011,897 | B2 | 3/2006 | Thompson et al. |
| 7,026,480 | B2 | 4/2006 | Che et al. |
| 2001/0015432 | A1 | 8/2001 | Igarashi |
| 2001/0019782 | A1 | 9/2001 | Igarashi et al. |
| 2002/0024293 | A1 | 2/2002 | Igarashi et al. |
| 2002/0034656 | A1 | 3/2002 | Thompson et al. |
| 2002/0048689 | A1 | 4/2002 | Igarashi et al. |
| 2002/0063516 | A1 | 5/2002 | Tsuboyama et al. |
| 2002/0064681 | A1 | 5/2002 | Takiguchi et al. |
| 2002/0071963 | A1 | 6/2002 | Fujii |
| 2002/0121638 | A1 | 9/2002 | Grushin et al. |
| 2002/0179885 | A1 | 12/2002 | Che et al. |
| 2002/0182441 | A1 | 12/2002 | Lamansky et al. |
| 2002/0190250 | A1 | 12/2002 | Grushin et al. |
| 2003/0068526 | A1 | 4/2003 | Kamatani et al. |
| 2003/0068536 | A1 | 4/2003 | Tsuboyama et al. |
| 2003/0072964 | A1 | 4/2003 | Kwong et al. |
| 2003/0091862 | A1 | 5/2003 | Tokito et al. |
| 2003/0096138 | A1 | 5/2003 | Lecloux et al. |
| 2003/0141809 | A1 | 7/2003 | Furugori et al. |
| 2003/0162299 | A1 | 8/2003 | Hsieh et al. |
| 2004/0075096 | A1 | 4/2004 | Grushin et al. |
| 2004/0174116 | A1 | 9/2004 | Lu et al. |
| 2004/0209116 | A1 | 10/2004 | Ren et al. |
| 2005/0170206 | A1 | 8/2005 | Ma et al. |
| 2005/0258433 | A1 * | 11/2005 | Djurovich et al. ............ 257/79 |
| 2005/0260449 | A1 | 11/2005 | Walters et al. |
| 2006/0258043 | A1 * | 11/2006 | Bold et al. ...................... 438/99 |
| 2007/0184301 | A1 * | 8/2007 | Oshiyama et al. ........... 428/690 |
| 2009/0115322 | A1 * | 5/2009 | Walters et al. ................ 313/504 |

FOREIGN PATENT DOCUMENTS

| EP | 1 191 613 | 3/2002 |
| EP | 1 191 614 | 3/2002 |
| EP | 1 239 526 | 9/2002 |
| JP | 2008266163 | 11/2008 |
| WO | WO 92/02714 | 2/1992 |
| WO | WO 02/02714 | 1/2002 |
| WO | WO 02/15645 | 2/2002 |
| WO | WO 02/074015 | 9/2002 |
| WO | WO 03/084972 | 10/2003 |
| WO | WO 03/099959 | 12/2003 |
| WO | WO 2005019373 A2 * | 3/2005 |
| WO | WO 2006067074 A1 * | 6/2006 |

OTHER PUBLICATIONS

PCT International Search Report and Written Opinion for PCT/US2008/078697, mailed on Jan. 16, 2009.

Baldo et al., "Highly Efficient Phosphorescent Emission from Organic Electroluminescent Devices," Nature, vol. 395, pp. 151-154 (1998).

Baldo et al., "Very High-Efficiency Green Organic Light-Emitting Devices Based on Electrophosphorescence," Appl. Phys. Lett., vol. 75, No. 3, pp. 4-6 (1999).

Adachi et al., "Nearly 100% Internal Phosphorescent Efficiency in an Organic Light Emitting Device," J. Appl. Phys., vol. 90, pp. 5048-05051 (2001).

"Inorganic Chemistry" ($2^{nd}$ Edition) by Gary L. Miessler and Donald A. Tarr, Prentice Hall, pp. 1-3, 422-424, 442, Aug. 1999 version.

Thomas H. Lowry et al., "Mechanism and Theory in Organic Chemistry," Harper & Row Publishers, New York, p. 256 (1976).

Nicholas J. Turro, Modern Molecular Photochemistry, University Science Books, Sausalito, California, pp. 109-110.

(Continued)

*Primary Examiner* — Dawn L. Garrett
*Assistant Examiner* — Andrew K Bohaty
(74) *Attorney, Agent, or Firm* — Kenyon & Kenyon LLP

(57) ABSTRACT

The present invention relates to organic light emitting devices (OLEDs), and more specifically to phosphorescent organic materials used in such devices. More specifically, the present invention relates to emissive phosphorescent material which comprise at least one tridentate ligand bound to a metal center, wherein at least one of the bonds to the tridentate ligand is a carbon-metal bond.

6 Claims, 75 Drawing Sheets

OTHER PUBLICATIONS

Nemcsok et al., "The Significance of π Interactions in Group 11 Complexes with N-Heterocyclic Carbenes", Organometallics, vol. 23, pp. 3640-3646, 2004.

Koizumi et al., "Terpyridine-Analogous (N,N,C)-Tridentate Ligands: Synthesis, Structures, and Electrochemical Properties of Ruthenium (II) Complexes Bearing Gtridentate Pyridinium and Pyridinylidene Ligands," Organometallics, vol. 22, pp. 970-975 (2003).

Bourissou et al., "Stable Carbenes," Chem Rev. vol. 100, pp. 39-91 (2000).

Ashekenazi et al., "Discovery of the First Metallaquinone," J. Am. Chem. Soc., vol. 122, pp. 8797-8798 (2000).

Cattoen, et al., "Amino-Aryl-Carbenes: Alternative Ligands for Transition Metals?" J. Am. Chem. Soc., vol. 126, pp. 1342-1343 (2004).

Wong et al., "Ruthenium (II) o-Acetylide and Carbene Complexes Supported by the Terpyridine-Bipyridine Ligand Set: Structural, Spectroscopic, and Photochemical Studies," Organometallics, vol. 23, pp. 2263-2272 (2004).

Klapars et al., "A General and Efficient Copper Catalyst for the Amidation of Aryl Halides and the N-Arylation of Nitrogen Heterocycles," J. Am. Chem. Soc., vol. 123, pp. 7727-7729 (2001).

Lai et al., "Carbene andf Isocyanide Ligation at Luminescent Cyclometalated 6-Phenyl-2,2'-bipyridyl Platinum (II) Complexes: Structural and Spectroscopic Studies," Organometallics, vol. 18, pp. 3327-3336 (1999).

Xue et al., "Spectroscopic and Excited-State Properties of Luminescent Rhenium (I) N-Heterocyclic Carbene Complexes Containing Aromatic Diimine Ligands," Organometallics, vol. 17, pp. 1622-1630 (1998).

Wang et al., "Facile Synthesis of Silver (I)-Carbene Complexes. Useful Carbene Transfer Agents," Organometallics, vol. 17, pp. 972-975 (1998).

Cardin et al., "Transition Metal-Carbene Complexes," Chem. Rev., vol. 72, pp. 545-574 (1972).

S. Strauss et al., "The Search for Larger and More Weakly Coordinating Anions", Chem. Rev., 1993, 93, pp. 927-642.

Kunkley et al., "Optical Properties of Transition Metal Complexes with N-Heterocyclic Carbenes as Ligands. 1,3-di-t-Butylimidazol-2-ylidene as Charge Transfer Donor and Acceptor," J. Organometallic Chem., vol. 684, pp. 113-116 (2003).

Anthony R. Chianese et al., "Abnormal C5-Bound N-Heterocyclic Carbenes: Extremely Strong Electron Donor Ligands and Their Iridium (I) and Iridium (III) Complexes," Organometallics, vol. 23, pp. 2461-2468 (2004).

Xile Hu et al., "Group 11 Metal Complexes of N-Heterocyclic Carbene Ligands: Nature of the Metal-Carbene Bone," Organometallics, vol. 23, pp. 755-764 (2004).

Xile Hu et al., "A Bis-Carbenealkenyl Copper(I) Complex from a Tripodal Tris-Carbene Ligand," Organometallics, vol. 22, pp. 3016-3018 (2003).

Siu-Wai Lai et al., "[{Pt(CN)($C_{10}H_{21}N_4$)}$_6$]: A Luminescent Hexanuclear Platinum (II) Macrocycle Containing Chelating Dicarbene and Bridging Cyanide Ligands," Angnew. Chem. Int. Ed., vol. 37, No. 1/2, pp. 182-184 (1998).

Xile Hu et al., "Silver Complexes of a Novel Tripodal N-Heterocyclic Carbene Ligand: Evidence for Significant Metal-Carbene n-Interaction," Organometallics, vol. 22, pp. 612-614 (2003).

James P. Collman et al., "Principles and Applications of Organotransition Metal Chemistry," University Science Books, Mill Valley, CA, pp. 119-121(1987).

S. Lamansky, et al., "Highly Phosphorescent Bis-Cyclometalated Iridium Complexes: Synthesis, Photophysical Characterization, and Use in Organic Light Emitting Diodes", *J. Am. Chem. Soc.*, 2001, 123, pp. 4304-4312.

R.J. Holmes, et al., "Efficient, deep-blue organic electrophosphorescence by guest charge trapping", *Applied Physics Letters*, vol. 83, No. 18, pp. 3618-3818, Nov. 3, 2003.

Son et al., "Synthesis of Ru(II) Complexes of N-Heterocyclic Carbenes and Their Promising Photoluminescence Properties in Water", Iorg. Chem., vol. XX, No. XX, pp. A-C.

U.S. Appl. No. 10/233,470, to Shtein et al., filed Sep. 4, 2002.

* cited by examiner

| | CIE x | CIE y |
|---|---|---|
| Device DA | 0.22 | 0.55 |
| Device DC | 0.29 | 0.57 |
| Device DB | 0.23 | 0.56 |
| Device DD | 0.29 | 0.59 |

HIL4 [10nm] / NPD [30nm] / CBP:es-5, 6% [30nm] / HPT [5nm] / Alq [45nm] / LiF [0.5nm] / Al [100nm]

HIL4 [10nm] / NPD [30nm] / CBP:es-5, 6% [30nm] / HPT [5nm] / Alq [45nm] / LiF [0.5nm] / Al [100nm]

HIL4 [10nm] / NPD [30nm] / CBP:es-5, 6% [30nm] / HPT [5nm] / Alq [45nm] / LiF [0.5nm] / Al [100nm]

HIL4 [10nm] / NPD [30nm] / CBP:es-5, 6% [30nm] / HPT [5nm] / Alq [45nm] / LiF [0.5nm] / Al [100nm]

HIL4 [10nm] / NPD [30nm] / CBP:es-5, 10% [30nm] / HPT [5nm] / Alq [45nm] / LiF [0.5nm] / Al [100nm]

HIL4 [10nm] / NPD [30nm] / CBP:es-5, 10% [30nm] / HPT [5nm] / Alq [45nm] / LiF [0.5nm] / Al [100nm]

HIL4 [10nm] / NPD [30nm] / CBP:es-5, 10% [30nm] / HPT [5nm] / Alq [45nm] / LiF [0.5nm] / Al [100nm]

HIL4 [10nm] / NPD [30nm] / CBP:es-5, 10% [30nm] / HPT [5nm] / Alq [45nm] / LiF [0.5nm] / Al [100nm]

CuPc [10nm] / NPD [30nm] / CBP:es-5, 6% [30nm] / HPT [5nm] / Alq [45nm] / LiF [0.5nm] / Al [100nm]

CuPc [10nm] / NPD [30nm] / CBP:es-5, 6% [30nm] / HPT [5nm] / Alq [45nm] / LiF [0.5nm] / Al [100nm]

CuPc [10nm] / NPD [30nm] / CBP:es-5, 6% [30nm] / HPT [5nm] / Alq [45nm] / LiF [0.5nm] / Al [100nm]

CuPc [10nm] / NPD [30nm] / CBP:es-5, 10% [30nm] / HPT [5nm] / Alq [45nm] / LiF [0.5nm] / Al [100nm]

CuPc [10nm] / NPD [30nm] / CBP:es-5, 10% [30nm] / HPT [5nm] / Alq [45nm] / LiF [0.5nm] / Al [100nm]

CuPc [10nm] / NPD [30nm] / CBP:es-5, 10% [30nm] / HPT [5nm] / Alq [45nm] / LiF [0.5nm] / Al [100nm]

CuPc [10nm] / NPD [30nm] / CBP:es-5, 10% [30nm] / HPT [5nm] / Alq [45nm] / LiF [0.5nm] / Al [100nm]

HIL4 [10nm] / NPD [30nm] / CBP:es-5, 6% [30nm] / CBP [5nm] / Alq [45nm] / LiF [0.5nm] / Al [100nm]

HIL4 [10nm] / NPD [30nm] / CBP:es-5, 6% [30nm] / CBP [5nm] / Alq [45nm] / LiF [0.5nm] / Al [100nm]

HIL4 [10nm] / NPD [30nm] / CBP:es-5, 6% [30nm] / CBP [5nm] / Alq [45nm] / LiF [0.5nm] / Al [100nm]

HIL4 [10nm] / NPD [30nm] / CBP:es-5, 15% [30nm] / HPT[5nm] / Alq [45nm] / LiF [0.5nm] / Al [100nm]

HIL4 [10nm] / NPD [30nm] / CBP:es-5, 15% [30nm] / HPT[5nm] / Alq [45nm] / LiF [0.5nm] / Al [100nm]

HIL4 [10nm] / NPD [30nm] / CBP:es-5, 15% [30nm] / HPT[5nm] / Alq [45nm] / LiF [0.5nm] / Al [100nm]

HIL4 [10nm] / NPD [30nm] / CBP:es-5, 15% [30nm] / HPT[5nm] / Alq [45nm] / LiF [0.5nm] / Al [100nm]

HIL4 [10nm] / NPD [30nm] / CBP:es-5, 6% [30nm] / Alq [45nm] / LiF [0.5nm] / Al [100nm]

HIL4 [10nm] / NPD [30nm] / CBP:es-5, 6% [30nm] / Alq [45nm] / LiF [0.5nm] / Al [100nm]

HIL4 [10nm] / NPD [30nm] / CBP:es-5, 6% [30nm] / Alq [45nm] / LiF [0.5nm] / Al [100nm]

HIL4 [10nm] / NPD [30nm] / CBP:es-5, 6% [30nm] / Alq [45nm] / LiF [0.5nm] / Al [100nm]

HIL4 [10nm] / NPD [30nm] / CBP:es-5, 15% [30nm] / Alq [45nm] / LiF [0.5nm] / Al [100nm]

HIL4 [10nm] / NPD [30nm] / CBP:es-5, 15% [30nm] / Alq [45nm] / LiF [0.5nm] / Al [100nm]

HIL4 [10nm] / NPD [30nm] / CBP:es-5, 15% [30nm] / Alq [45nm] / LiF [0.5nm] / Al [100nm]

HIL4 [10nm] / NPD [30nm] / CBP:es-5, 15% [30nm] / Alq [45nm] / LiF [0.5nm] / Al [100nm]

es-1 es-2 es-3 es-4 es-5 es-6 es-7 es-8

1,000 nits Lifetime

COMPLEXES WITH TRIDENTATE LIGANDS

RESEARCH AGREEMENTS

The claimed invention was made by, on behalf of, and/or in connection with one or more of the following parties to a joint university corporation research agreement: Princeton University, The University of Southern California, The University of Michigan and Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and more specifically to phosphorescent organic materials used in such devices. More specifically, the present invention relates to emissive phosphorescent material which comprise at least one tridentate ligand bound to a metal center, wherein at least one of the bonds to the tridentate ligand is a carbon-metal bond.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules. In general, a small molecule has a well-defined chemical formula with a single molecular weight whereas a polymer has a chemical formula and a molecular weight that may vary from molecule to molecule.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

The carbene ligand has been well known in organometallic chemistry, and is used to generate a wide range of thermally stable catalytic materials. The carbene ligands have been employed both as active groups, directly engaged in the catalytic reactions, and serving a role of stabilizing the metal in a particular oxidation state or coordination geometry. However, applications of carbene ligands are not well known in photochemistry.

One issue with many of the existing organic electroluminescent compounds is that they are not sufficiently stable for use in commercial devices. This has been particularly true of phosphorescent emissive materials that emit in the blue portion of the spectra. An object of the invention is to provide a class of organic emissive compounds having improved stability. An object of the invention is to provide a class of organic emissive compounds that can emit light with various spectra, including high energy spectra such as blue, in a stable manner.

SUMMARY OF THE INVENTION

The present invention is directed to an organic light emitting device having an emissive layer comprising a phosphorescent organometallic emissive material having at least one tridentate ligand bound to a metal center through at least one carbene-metal bond. In a preferred embodiment, the emissive material comprises two tridentate ligands, which may be the same or different, bound to the metal center, wherein at least one of the tridentate ligands has a carbene-metal bond.

In a preferred embodiment, the invention is directed to an organic light emitting device comprising an anode, a cathode, and a phosphorescent emissive region disposed between the anode and the cathode, wherein the emissive region comprises an emissive material having the formula I:

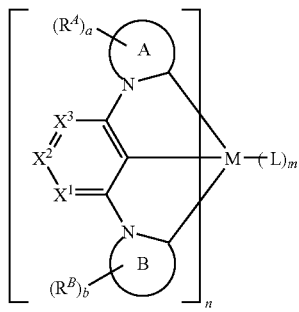

wherein:
M is a second or third row transition metal;
L is an ancillary ligand;
Ring A is selected from the group consisting of:
 (a) an 8- to 12-membered bicyclic group having from 3 to 5 ring heteroatoms;
 (b) an 11- to 18-membered tricyclic group having from 3 to 6 ring heteroatom;
 (c) an 11- to 14-membered fused tricyclic group; and
 (d) a 14- to 18-membered fused tetracyclic group;
each $R^A$ is independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;
a is 0 to 4
Ring B is selected from a 5- or 6-membered cyclic group, an 8- to 12-membered bicyclic group, an 11- to 18-membered tricyclic group, an 11- to 14-membered fused tricyclic group, and a 14- to 18-membered fused tetracyclic group;
each $R^B$ is independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;
b is 0 to 4;
$X^1$ is selected from C—R$^1$ and N;
$X^2$ is selected from C—R$^2$ and N;
$X^3$ is selected from C—R$^3$ and N;
R$^1$, R$^2$, and R$^3$ are independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;
alternatively, R$^1$ and R$^2$, or R$^2$ and R$^3$ taken together form a 5- or 6-membered cyclic group, an 8- to 10-membered fused bicyclic group, an 11- to 14-membered fused tricyclic group, which may be optionally substituted with one or more substituents independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;
additionally or alternatively, R$^1$ and an R$^B$ taken together form a 5- or 6-membered cyclic group, or an 8- to 10-membered fused bicyclic group;
additionally or alternatively, R$^3$ and an R$^A$ taken together form a 5- or 6-membered cyclic group, or an 8- to 10-membered fused bicyclic group;
each R' is independently selected from H, alkyl, alkenyl, alkynyl, aralkyl, aryl and heteroaryl;
each R" is independently selected from H, alkyl, alkenyl, alkynyl and aralkyl;
n is 1 or 2; and
m is 0 to 3, wherein when n is 1, m is 1 to 3, and when n is 2, m is 0.

DETAILED DESCRIPTION

Figure 1:
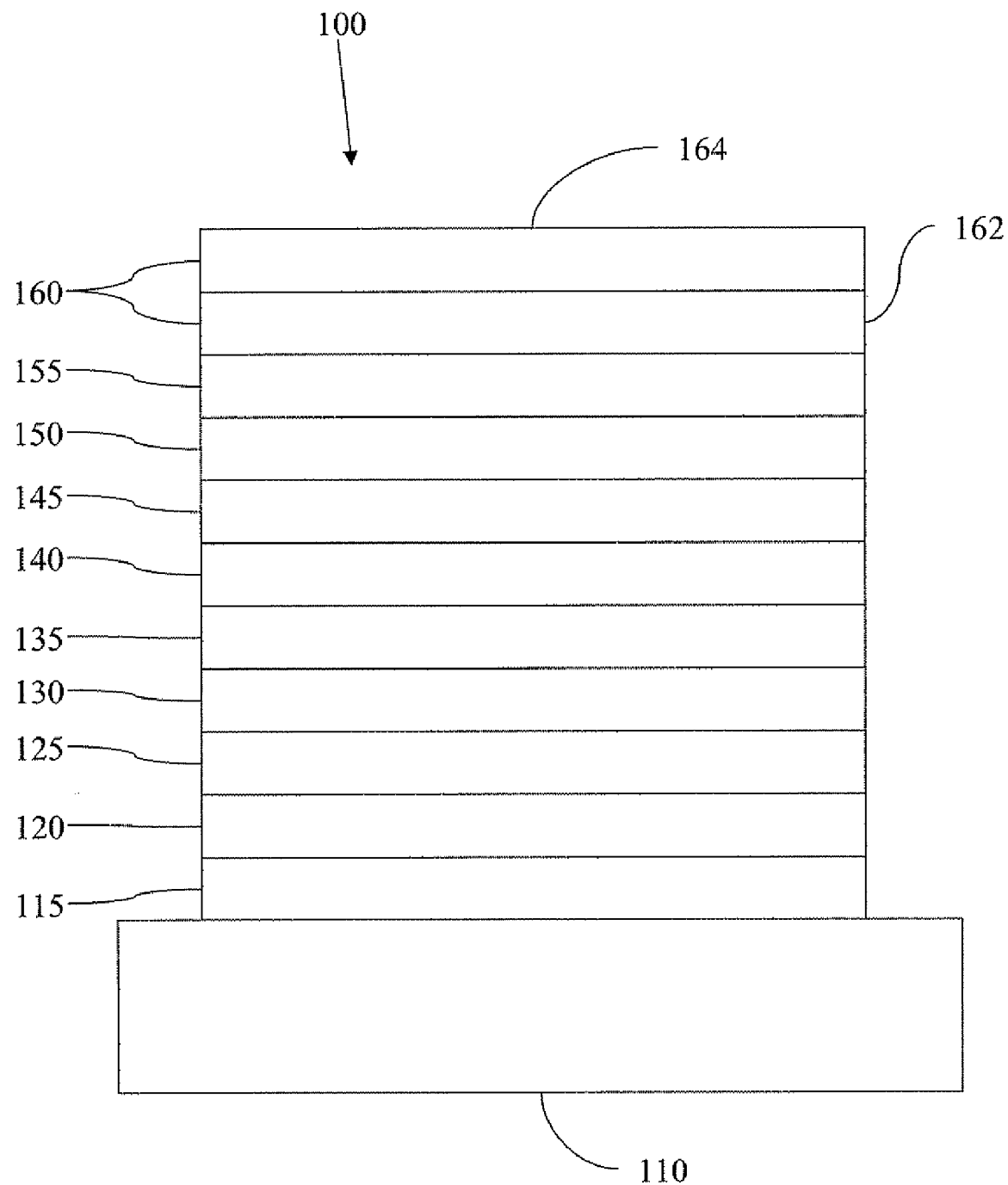
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that an organic material that exhibits phosphorescence at liquid nitrogen temperatures typically does not exhibit phosphorescence at room temperature. But, as demonstrated by Baldo, this problem may be addressed by selecting phosphorescent compounds that do phosphoresce at room temperature. Representative emissive layers include doped or undoped phosphorescent organometallic materials such as disclosed in U.S. Pat. Nos. 6,303,238 and 6,310,360; U.S. Patent Application Publication Nos. 2002-0034656; 2002-0182441; 2003-0072964; and WO-02/074015.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak.

The term "organometallic" as used herein is as generally understood by one of ordinary skill in the art and as given, for example, in "Inorganic Chemistry" (2nd Edition) by Gary L. Miessler and Donald A. Tarr, Prentice Hall (1998). Thus, the term organometallic refers to compounds which have an organic group bonded to a metal through a carbon-metal bond. This class does not include per se coordination compounds, which are substances having only donor bonds from heteroatoms, such as metal complexes of amines, halides, pseudohalides (CN, etc.), and the like. In practice organometallic compounds generally comprise, in addition to one or more carbon-metal bonds to an organic species, one or more donor bonds from a heteroatom. The carbon-metal bond to an organic species refers to a direct bond between a metal and a carbon atom of an organic group, such as phenyl, alkyl, alkenyl, etc., but does not refer to a metal bond to an "inorganic carbon," such as the carbon of CN or CO.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. Nos. 5,844,363 and 6,602,540 B2, which are incorporated by reference in their entireties. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in United States Patent Application Publication No. 2002-0071963 A1 to Forrest et al., which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material which may be capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include $Ir(ppy)_3$. Examples of fluorescent emissive materials include DCM and DMQA. Examples of host materials include $Alq_3$, CBP and mCP. Examples of emissive and host materials are disclosed in U.S. Pat. No. 6,303,238 to Thompson et al., and U.S. Application Publication No. US-2004-0209116 A1, each of which is incorporated by reference in its entirety. Emissive material may be included in emissive layer 135 in a number of ways. For example, an emissive small molecule may be incorporated into a polymer. This may be accomplished by several ways: by doping the small molecule into the polymer either as a separate and distinct molecular species; or by incorporating the small molecule into the backbone of the polymer, so as to form a co-polymer; or by bonding the small molecule as a pendant group on the polymer. Other emissive layer materials and structures may be used. For example, a small molecule emissive material may be present as the core of a dendrimer.

Many useful emissive materials include one or more ligands bound to a metal center. A ligand may be referred to as "photoactive" if it contributes directly to the photoactive properties of an organometallic emissive material. A "photoactive" ligand may provide, in conjunction with a metal, the energy levels from which and to which an electron moves when a photon is emitted. Other ligands may be referred to as "ancillary." Ancillary ligands may modify the photoactive properties of the molecule, for example by shifting the energy levels of a photoactive ligand, but ancillary ligands do not directly provide the energy levels involved in light emission. A ligand that is photoactive in one molecule may be ancillary in another. These definitions of photoactive and ancillary are intended as non-limiting theories.

Electron transport layer 145 may include a material capable of transporting electrons. Electron transport layer 145 may be intrinsic (undoped), or doped. Doping may be used to enhance conductivity. $Alq_3$ is an example of an intrinsic electron transport layer. An example of an n-doped electron transport layer is BPhen doped with Li at a molar ratio of 1:1, as disclosed in United States Patent Application Publication No. 2002-0071963 A1 to Forrest et al., which is incorporated by reference in its entirety. Other electron transport layers may be used.

The charge carrying component of the electron transport layer may be selected such that electrons can be efficiently injected from the cathode into the LUMO (Lowest Unoccupied Molecular Orbital) energy level of the electron transport layer. The "charge carrying component" is the material responsible for the LUMO energy level that actually transports electrons. This component may be the base material, or it may be a dopant. The LUMO energy level of an organic material may be generally characterized by the electron affinity of that material and the relative electron injection efficiency of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436, 5,707,745, 6,548,956 B2 and 6,576,134 B2, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 145. Blocking layers may also be used to block excitons from diffusing out of the emissive layer. The theory and use of blocking layers is described in more detail in U.S. Pat. No. 6,097,147 and United States Patent Application Publication No. 2002-0071963 A1 to Forrest et al., which are incorporated by reference in their entireties.

As used herein, and as would be understood by one skilled in the art, the term "blocking layer" means that the layer provides a barrier that significantly inhibits transport of charge carriers and/or excitons through the device, without suggesting that the layer necessarily completely blocks the charge carriers and/or excitons. The presence of such a blocking layer in a device may result in substantially higher efficiencies as compared to a similar device lacking a blocking layer. Also, a blocking layer may be used to confine emission to a desired region of an OLED.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the HIL and the hole transporting layer on the opposite side of the HIL. The "charge carrying component" is the material responsible for the HOMO energy level that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are further distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., which is incorporated by reference in its entirety.

Figure 2:
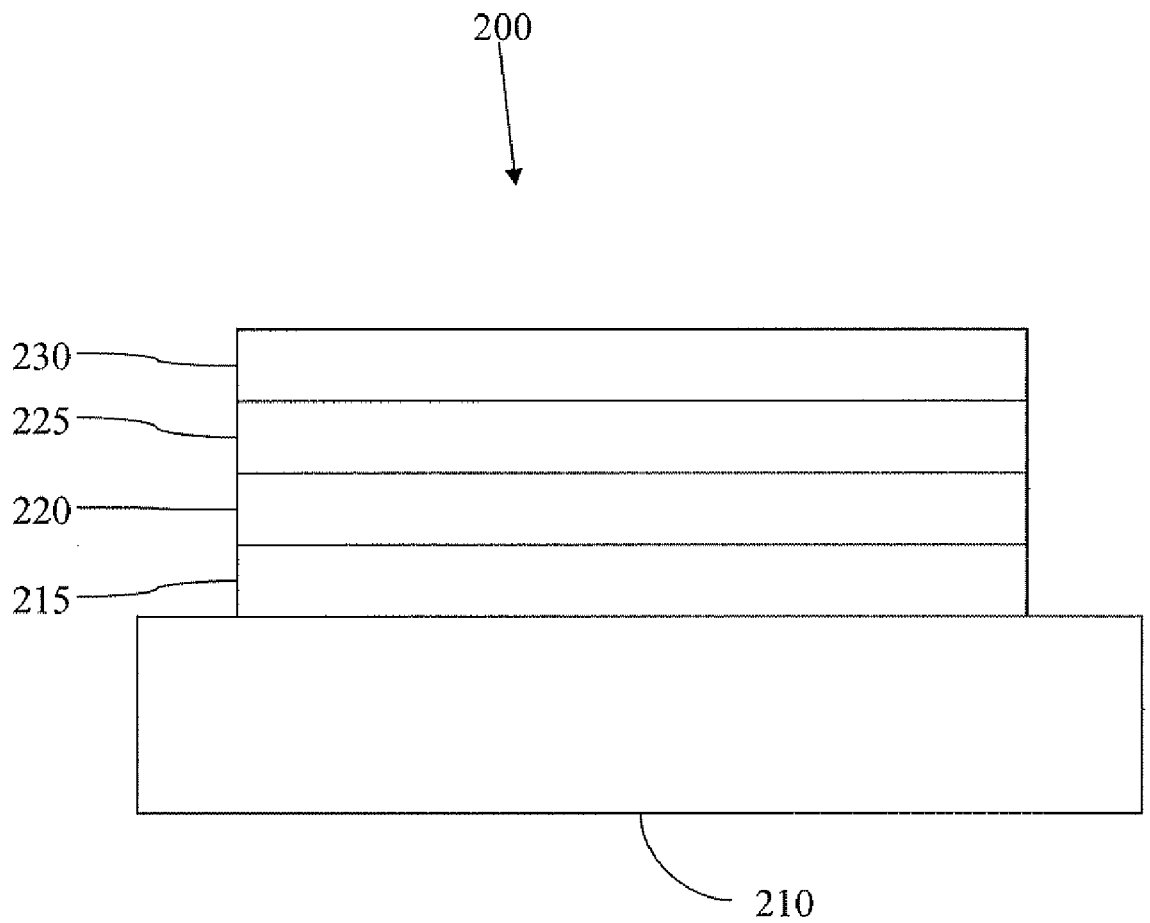
FIG. 2 shows an inverted organic light emitting device that does not have a separate electron transport layer.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al., which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

The molecules disclosed herein may be substituted in a number of different ways without departing from the scope of the invention. For example, substituents may be added to a compound having two or more mono-, bi- and/or tridentate ligands, such that after the substituents are added, one or more of the mono-, bi- and/or tridentate ligands are linked together to form, for example, a tetradentate or hexadentate ligand. Other such linkages may be formed. It is believed that this type of linking may increase stability relative to a similar compound without linking, due to what is generally understood in the art as a "chelating effect."

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The present invention is directed to a device having an emissive layer comprising a phosphorescent organometallic emissive material having at least one tridentate ligand bound to a metal center through at least one carbon-metal bond. The metal center is selected from the second and third row transition metals and is preferably selected from Ru, Os, Re, Rh, Ir, Pd and Pt. In particularly preferred embodiments, M is selected from Os and Ru, and in still more preferred embodiments, M is Os. The emissive material may additionally contain ancillary ligand to fill the coordination sphere of the metal center. In a preferred embodiment, the emissive material comprises two tridentate ligands, which may be the same or different, bound to the metal center, wherein at least one of the tridentate ligands has a carbon-metal bond. In a particularly preferred embodiment, the metal center is osmium. The device may contain additional emissive materials that may be phosphorescent emissive materials or fluorescent emissive materials.

In a preferred embodiment of the invention, the carbon-metal bond to the tridentate ligand of the emissive material is a carbene-metal bond. Thus, in this embodiment, the emissive material comprises at least one tridentate ligand bound to a metal center through at least one carbene-metal bond. The two other bonds to the metal center may be selected from (i) dative bonds from a heteroatom selected from N, O, S, and P, (ii) carbon-metal bonds that are not carbene-metal bonds, (iii) carbene-metal bonds, or any combination thereof.

As used herein, the term "carbene" refers to compounds having a divalent carbon atom with only six electrons in its valence shell when not coordinated to a metal. A useful exercise to determine whether a ligand includes a carbene-metal bond is to mentally deconstruct the complex as a metal fragment and a ligand, and to then determine whether a carbon atom in the ligand that was previously bound to the metal is a neutral divalent carbon atom in the deconstructed state. The resonance forms of a preferred embodiment may be shown as:

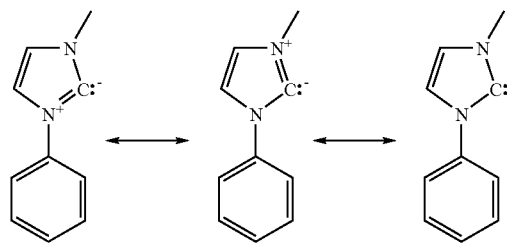

This definition of carbene is not limited to metal-carbene complexes synthesized from carbenes, but is rather intended to address the orbital structure and electron distribution associated with the carbon atom that is bound to the metal. The definition recognizes that the "carbene" may not technically be divalent when bound to the metal, but it would be divalent if it were detached from the metal. Although many such compounds are synthesized by first synthesizing a carbene and then binding it to a metal, the definition is intended to encompass compounds synthesized by other methods that have a similar orbital structure and electron configuration. Lowry & Richardson, *Mechanism and Theory in Organic Chemistry* 256 (Harper & Row, 1976) defines "carbene" in a way that is consistent with the way the term is used herein. Some references may define "carbene" as a carbon ligand that forms a double bond to a metal. While this definition is not being used in the present application, there may be some overlap between the two definitions. A variety of representations are used to depict the bonding in such carbenes, including those in which a curved line is used to indicate partial multiple bonding between the carbene carbon and the adjacent heteroatom(s).

Carbene ligands are especially desirable in OLED applications due to the high thermal stability exhibited by metal-carbene complexes. It is believed that the carbene, which behaves much as an electron donative group, generally bonds strongly to the metals, thus forming a more thermally stable complex than, for example, previous cyclometallated complexes used as phosphorescent emitters.

Moreover, due to the nature of a carbene-metal bond, it is believed that the emissive molecule comprising a carbene-metal bond may have increased stability, for example in comparison to a compound that is a non-carbene analog. It is further believed that the emissive spectra of the molecule including a carbene-metal bond may be different from the emissive spectra of the analog without a carbene.

Metal-carbene complexes may be tuned to emit a wide variety of spectra from the near-ultraviolet across the entire visible spectra by the selection of substituents and/or chemical groups on the ligand(s). More significantly, it may now be possible to obtain saturated blue color emissions with peak wavelengths at about 450 nm. Because it is believed to be materially easier to reduce than to increase the triplet energy by tuning an emissive compound, the ability to make stable blue emitters at such high energies would also allow for the possibility of obtaining any color by reducing the energy so as to red-shift the emission.

The appropriate selection of substituents and/or chemical groups attached to carbene ligands may also minimize quantum efficiency losses associated with increasing temperatures. The observable difference in lifetime measurements between emission at room temperature and at low temperatures (e.g. 77 K) is believed to be attributed to non-radiative quenching mechanisms that compete with phosphorescent emission. Such quenching mechanisms are further believed to be thermally activated, and consequently, at cooler temperatures of about 77 K, where energy loss due to quenching is not an issue, quantum efficiency is about 100%. It is believed that appropriate substituents on the carbene ligand, or doping in a more rigid matrix, such as disclosed in Turro, "Modern Molecular Photochemistry", University Science Books (1991), 109-10, may increase quantum efficiency at room temperature and correspondingly show longer lifetimes.

In some embodiments, the triplet energy of the carbene complex has a corresponding wavelength in the deep blue or ultraviolet (UV) part of the spectra. In some embodiments, the phosphorescent emissive compound has triplet energy corresponding to a wavelength of less than 450 nm. In preferred embodiments, the triplet energy corresponds to a wavelength of less than 440 nm, and in even more preferred embodiments, it corresponds to a wavelength less than 400 nm, which is believed to be in the UV region of the spectrum, since 400 nm is believed to represent the cut-off between the UV and the visible regions of the spectrum. Such high triplet energy may make these compounds useful in optically pumping down converting layers. For such applications, an overlap is preferred between the emission spectra of the ultraviolet carbene compound and the absorption spectra of the down converting layer. It is believed that when about 50% of the integral of the curve for the normalized electroluminescent spectra of the device is at a wavelength less than about 450 nm, there is sufficient energy to optically pump a down converting layer. More preferably, greater than 90% of the emission may be produced below 440 nm, as disclosed herein. Preferably, 50% of the integral of the curve for the normalized electroluminescent spectra is less than about 440 nm, and more preferably, it is less than about 400 nm. The wavelength cutoffs mentioned above are not intended to be absolute limitations as they depend on the energy of the material to be pumped. It is also believed that these emissions may occur at room temperature.

The strong metal-carbon bond is also believed to lead to greater spin-orbit coupling in metal carbene complexes. Moreover, the triplet energy of coordinated carbenes are shown to be significantly higher than pyridine analogs. The emission may be in the near-ultraviolet range of the spectrum even at room temperature. It is believed herein that metal carbene complexes may be capable of emitting at similarly high energies due to the strong metal-ligand bond associated with carbene ligands.

The stability of metal-carbene complexes may also allow increased versatility in the types of ligands and metals that may be used as phosphorescent emitters in OLEDs. The strong metal-carbene bond may allow a variety of metals to form useful phosphorescent complexes with carbene ligands to give novel emissive compounds.

The emissive materials of the present invention comprise a tridentate ligand that is a photoactive ligand. A ligand is referred to as "photoactive" because it is believed that it contributes to the photoactive properties of the emissive material. The emissive material may further include ancillary ligands. These ligands are referred to as "ancillary" because it is believed that they may modify the photoactive properties of the molecule, as opposed to directly contributing to the photoactive properties. The definitions of photoactive and ancillary are intended as non-limiting theories. The ancillary ligands may be selected from those disclosed in the following references:

U.S. Pat. Application Publ. No. 2002-0034656 (K&K 10020/15303), FIGS. 11-50, U.S. Pat. Application Publ. No. 2003-0072964 (Thompson et al.), paragraphs 7-132; and FIGS. 1-8; U.S. Pat. Application Publ. No. 2002-0182441 (Lamansky et al.), paragraphs 13-165, including FIGS. 1-9(g); U.S. Pat. No. 6,420,057 B1 (Ueda et al.), col. 1, line 57, through col. 88, line 17, including each compound I-1 through XXIV-12; U.S. Pat. No. 6,383,666 B1 (Kim et al.), col. 2, line 9, through col. 21, lin3 67; U.S. Pat. Application Publ. No. 2001-0015432 A1 (Igarashi et al.), paragraphs 2-57, including compounds (1-1) through (1-30); U.S. Pat. Application Publ. No. 2001-0019782 A1 (Igarashi et al.), paragraphs 13-126, including compounds (1-1) through (1-70), and (2-1) through (2-20); U.S. Pat. Application Publ. No. 2002-0024293 (Igarashi et al.), paragraphs 7-95, including general formulas K-I through K-VI, and example compounds (K-1) through (K-25); U.S. Pat. Application Publ. No. 2002-0048689 A1 (Igarashi et al.), paragraphs 5-134, including compounds 1-81, and example compounds (1-1) through (1-81); U.S. Pat. Application Publ. No. 2002-0063516 (Tsuboyama et al.), paragraphs 31-161, including each compound 1-16; U.S. Pat. Application Publ. No. 2003-0068536 (Tsuboyama et al.), paragraphs 31-168, including each compound in Tables 1-17, corresponds to EP-1-239-526-A2; U.S. Pat. Application Publ. No. 2003-0091862 (Tokito et al.), paragraphs 10-190, including each compound in Tables 1-17, corresponds to EP-1-239-526-A2; U.S. Pat. Application Publ. No. 2003-0096138 (Lecloux et al.), paragraphs 8-124, including FIGS. 1-5; U.S. Pat. Application Publ. No. 2002-0190250 (Grushin et al.), paragraphs 9-191; U.S. Pat. Application Publ. No. 2002-0121638 (Grushin et al.), paragraphs 8-125; U.S. Pat. Application Publ. No. 2003-0068526 (Kamatani et al.), paragraphs 33-572, including each compound in Tables 1-23; U.S. Pat. Application Publ. No. 2003-0141809 (Furugori et al.), paragraphs 29-207; U.S. Pat. Application Publ. No. 2003-0162299 A1 (Hsieh et al.), paragraphs 8-42; WO 03/084972, (Stossel et al.), Examples 1-33; WO 02/02714 A2 ((Petrov et al.), pages 2-30, including each compound in Tables 1-5; EP 1-191-613 A1 (Takiguchi et al.), paragraphs 26-87, including each compound in Tables 1-8, (corresponding to U.S. Pat. Application Publ. No. 2002-0064681); and EP 1-191-614 A2 (Tsuboyama et al.), paragraphs 25-86, including each compound in Tables 1-7; which are incorporated herein by reference in their entirety.

In a preferred embodiment, the invention is directed to an organic light emitting device comprising an anode, a cathode, and a phosphorescent emissive region disposed between the anode and the cathode, wherein the emissive region comprises an emissive material having the formula I:

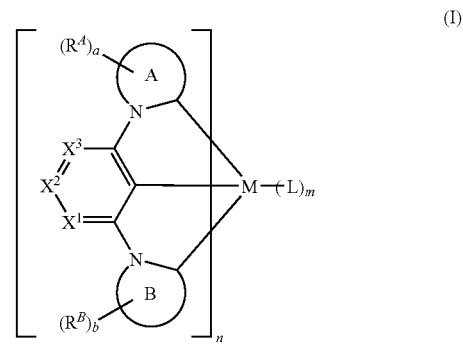

wherein:
M is a second or third row transition metal;
L is an ancillary ligand;
Ring A is selected from the group consisting of;
  (a) an 8- to 12-membered bicyclic group having from 3 to 5 ring heteroatoms;
  (b) an 11- to 18-membered tricyclic group having from 3 to 6 ring heteroatom;
  (c) an 11- to 14-membered fused tricyclic group; and
  (d) a 14- to 18-membered fused tetracyclic group;
each $R^A$ is independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;
a is 0 to 4
Ring B is selected from a 5- or 6-membered cyclic group, an 8- to 12-membered bicyclic group, an 11- to 18-membered tricyclic group, an 11- to 14-membered fused tricyclic group, and a 14- to 18-membered fused tetracyclic group;
each $R^B$ is independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;
b is 0 to 4;
$X^1$ is selected from C—$R^1$ and N;
$X^2$ is selected from C—$R^2$ and N;
$X^3$ is selected from C—$R^3$ and N;
$R^1$, $R^2$, and $R^3$ are independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;
alternatively, $R^1$ and $R^2$, or $R^2$ and $R^3$ taken together form a 5- or 6-membered cyclic group, an 8- to 10-membered fused bicyclic group, an 11- to 14-membered fused tricyclic group, which may be optionally substituted with one or more substituents independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;

additionally or alternatively, R$^1$ and an R$^B$ taken together form a 5- or 6-membered cyclic group, or an 8- to 10-membered fused bicyclic group;

additionally or alternatively, R$^3$ and an R$^A$ taken together form a 5- or 6-membered cyclic group, or an 8- to 10-membered fused bicyclic group;

each R' is independently selected from H, alkyl, alkenyl, alkynyl, aralkyl, aryl and heteroaryl;

each R" is independently selected from H, alkyl, alkenyl, alkynyl and aralkyl;

n is 1 or 2; and m is 0 to 3, wherein when n is 1, m is 1 to 3, and when n is 2, m is 0.

All value ranges, for example those given for n and m, are inclusive over the entire range. Thus, for example, a range between 0-4 would include the values 0, 1, 2, 3 and 4.

In preferred embodiments of the invention, M is selected from Ru, Os, Re, Rh, Ir, Pd and Pt. In particularly preferred embodiments, M is selected from Os and Ru, and in still more preferred embodiments, M is Os. For certain preferred embodiments, Os is the preferred metal as it is relatively easy to oxidize. In further preferred embodiments, the emissive material has an oxidation potential that is more positive than about −0.7 volts, more preferably more positive than about −0.3 volts, and still more preferably more positive than about 0 volts, relative to Ferrocene/Ferrocenium cation.

In another preferred embodiment, the compound according to the formula I is a neutral compound. Neutral compound may have the advantage of being easier to process in the manufacture of the device as they may be deposited using sublimation techniques.

In the case where the compound according to the formula I is a charged compound, the compound will include a counterion to balance the charge. In this case the metal complex will have as positive charge ranging from 1$^+$ to 6$^+$, and preferably from 1$^+$ to 3$^+$. The counterion may be selected from any appropriate anion which does not interfere with the function of the compound in the device, for example, as an emissive material. The anion is selected to be electrochemically inert over the operational voltage range of the device. Preferred counteranions are typically weakly coordinating anions. The term "weakly coordinating anion" is well known in the art per se and generally refers to a large bulky anion capable of delocalization of the negative change of the anion. Suitable weakly coordinating anions, not all of which would be considered bulky, include, but are not limited to: PF$_6^-$, BF$_4^-$, SbCl$_6^-$, trifluoromethansulfonate, BAr$_4^-$ (Ar=C$_6$F$_5$), BAr'$_4^-$ (Ar'=3,5-bis(trifluoromethyl)phenyl, and the like. The weakly coordinating nature of such anions is known to those skilled in the art and described in the literature (S. Strauss et al., Chem. Rev., 1993, 93, 927).

In the embodiments of the invention in which n is 1, m is an integer selected to satisfy the valency of M; plural L may be the same or different; and (L)$_m$ collectively comprise a 6-electron donor, uninegative ligand or group of ligands.

In certain embodiments of the invention, Ring A is different from Ring B. In preferred embodiments of the invention, Ring A and Ring B are selected to be the same.

In further embodiments of the invention the emissive material has the formula I$_a$:

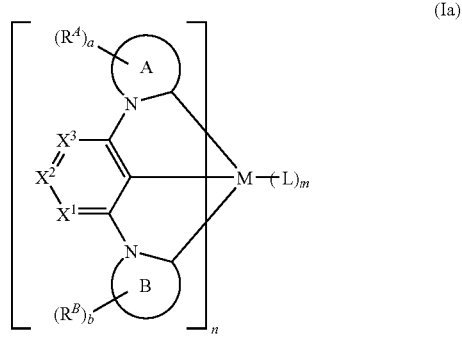

(Ia)

wherein:
M is a second or third row transition metal;
L is an ancillary ligand;
Ring A is selected from the group consisting of:
 (a) an 8- to 12-membered bicyclic group having from 3 to 5 ring heteroatoms;
 (b) an 11- to 18-membered tricyclic group having from 3 to 6 ring heteroatom;
 (c) an 11- to 14-membered fused tricyclic group; and
 (d) a 14- to 18-membered fused tetracyclic group;
each R$^A$ is independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;
a is 0 to 4
Ring B is selected from the group consisting of:
 (a) an 8- to 12-membered bicyclic group having from 3 to 5 ring heteroatoms;
 (b) an 11- to 18-membered tricyclic group having from 3 to 6 ring heteroatom;
 (c) an 11- to 14-membered fused tricyclic group; and
 (d) a 14- to 18-membered fused tetracyclic group;
each R$^B$ is independently selected from alkyl alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;
b is 0 to 4;
X$^1$ is selected from C—R$^1$ and N;
X$^2$ is selected from C—R$^2$ and N;
X$^3$ is selected from C—R$^3$ and N;
R$^1$, R$^2$, and R$^3$ are independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;
alternatively, R$^1$ and R$^2$, or R$^2$ and R$^3$ taken together form a 5- or 6-membered cyclic group, an 8- to 10-membered fused bicyclic group, an 11- to 14-membered fused tricyclic group, which may be optionally substituted with one or more substituents independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;
additionally or alternatively, R$^1$ and an R$^B$ taken together form a 5- or 6-membered cyclic group, or an 8- to 10-membered fused bicyclic group;
additionally or alternatively, R$^3$ and an R$^A$ taken together form a 5- or 6-membered cyclic group, or an 8- to 10-membered fused bicyclic group;
each R' is independently selected from H, alkyl, alkenyl, alkynyl, aralkyl, aryl and heteroaryl;

each R" is independently selected from H, alkyl, alkenyl, alkynyl and aralkyl;

n is 1 or 2; and m is 0 to 3, wherein when n is 1, m is 1 to 3, and when n is 2, m is 0.

In a further preferred embodiment of a compound according to the formula I, the metal center is bound to two tridentate ligand (n=2, m=0) to give a compound having the formula II:

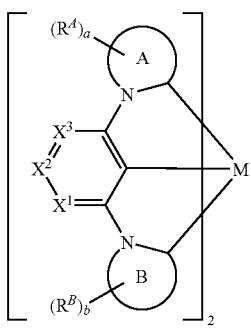

(II)

wherein $X^1$, $X^2$, $X^3$, $R^A$, $R^B$, M, Ring A, Ring B, a, and b are as described for a compound of the formula I.

Compounds of the present invention which comprise two tridentate ligands are preferred. Such compounds are preferred as it is believed that such ligand configurations may improve the stability of the materials when incorporated into an organic light emitting device. Further, such materials may have the additional advantage of being more stable to sublimation during preferred deposition techniques such as OVPD.

The term "5- or 6-membered cyclic group" refers to five or six membered rings, which may be saturated, partially unsaturated, or aromatic, and may optionally contain one or more ring heteroatoms.

When Ring A (and Ring B in certain embodiments) is selected to be (a) an 8- to 12-membered bicyclic group having from 3 to 5 ring heteroatoms, the rings of the bicyclic group may optionally be fused. In preferred embodiments, the rings of the bicyclic group are aromatic. Preferred bicyclic groups having from 3 to 5 ring heteroatoms may be selected from the following ring systems:

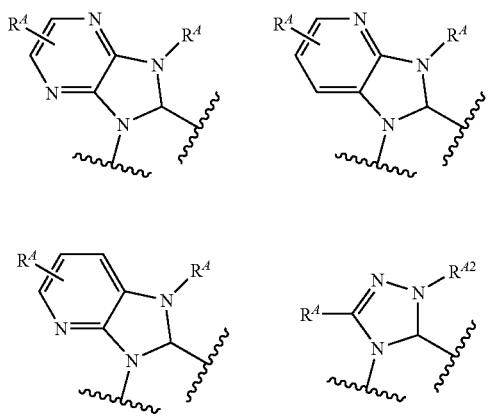

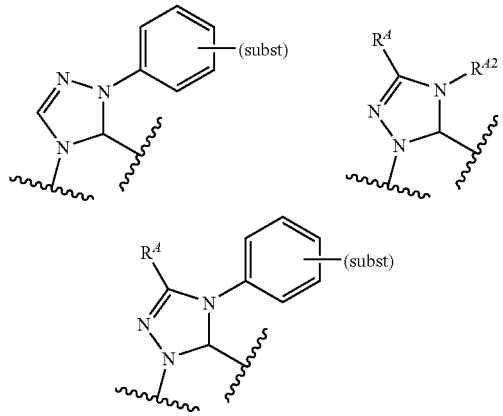

wherein $R^{A2}$ is a 5- to 6-membered cyclic group; and subst represents an optional substituent selected from halo, alkyl, CN, $CO_2R$, $C(O)R$, $NR_2$, cyclic-amino, $NO_2$, and OR.

The term "8- to 10-membered fused bicyclic group" refers to an eight to ten membered ring system, wherein each of the rings is fused (i.e., the rings share two adjacent ring atoms) and may be saturated, partially unsaturated, or aromatic, and may optionally contain one or more ring heteroatoms.

When Ring A (and Ring B in certain embodiments) is selected to be (b) an 11- to 18-membered tricyclic group having from 3 to 6 ring heteroatom, the two of the rings of the tricyclic group may optionally be fused. In preferred embodiments, the rings of the tricyclic group are aromatic. Preferred tricyclic groups having from 3 to 5 ring heteroatoms may be selected from the following ring systems:

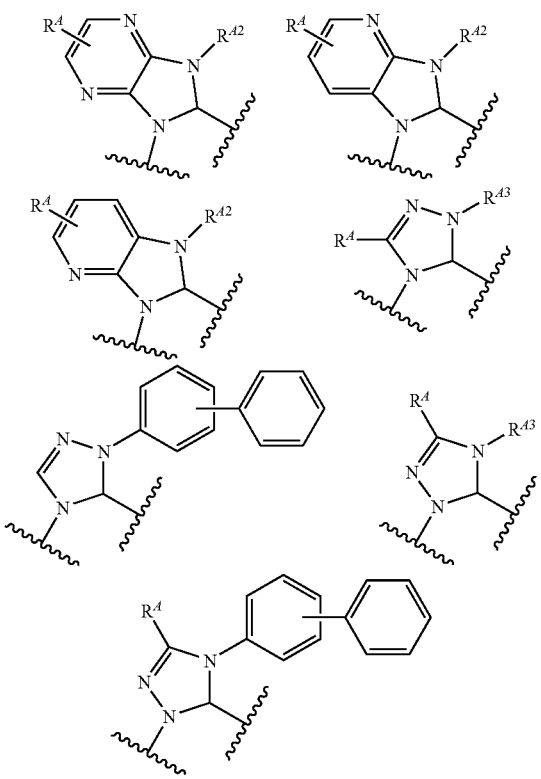

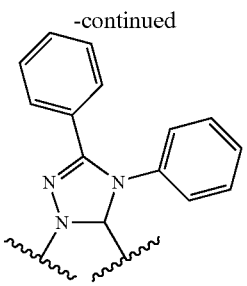

wherein $R^{42}$ is a 5- to 6-membered cyclic group; and $R^{43}$ is selected from an 8- to 12-membered bicyclic group.

The term "11- to 14-membered fused tricyclic group" refers to an eleven to fourteen membered ring system, wherein each of the rings may be saturated, partially unsaturated, or aromatic, and may optionally contain one or more ring heteroatoms.

In certain embodiments, Ring A (and Ring B in certain embodiments) is selected to be (c) an 11- to 14-membered fused tricyclic group. Preferred 11- to 14-membered fused tricyclic groups may be selected from the following ring systems:

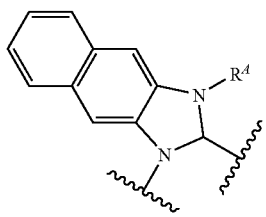

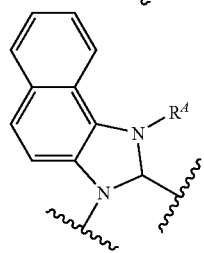

The term "14- to 18-membered fused tetracyclic group" refers to a fourteen to eighteen membered ring system, wherein each of the rings may be saturated, partially unsaturated, or aromatic, and may optionally contain one or more ring heteroatoms.

In certain embodiments, Ring A (and Ring B in certain embodiments) is selected to be (d) a 14- to 18-membered fused tetracyclic group. Preferred 14- to 18-membered fused tetracyclic groups may be selected from the following ring systems:

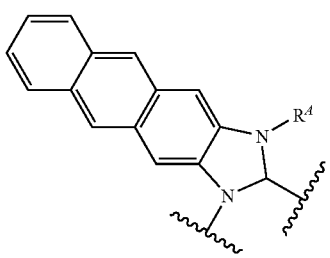

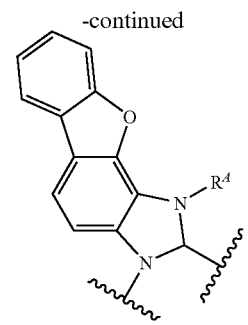

In a further embodiment of the invention, the emissive material has the formula III:

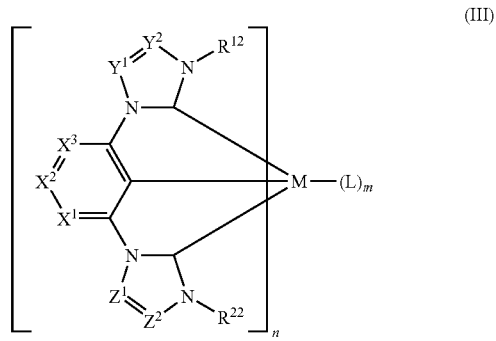

(III)

wherein:
M is a second or third row transition metal;
L is an ancillary ligand;
$Y^1$ is selected from N and C—$R^4$;
$Y^2$ is selected from N and C—$R^5$;
$R^4$ and $R^5$ are independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;
alternatively, $R^4$ and $R^5$ taken together form a 5- or 6-membered cyclic group, an 8- to 10-membered fused bicyclic group, an 11- to 14-membered fused tricyclic group, which may be optionally substituted with one or more substituents independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;
$R^{12}$ is selected from alkyl, aryl, aralkyl, cycloalkyl and C(O)R';
$Z^1$ is selected from N and C—$R^6$;
$Z^2$ is selected from N and C—$R^7$;
$R^6$ and $R^7$ are independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;
alternatively, $R^6$ and $R^7$ taken together form a 5- or 6-membered cyclic group, an 8- to 10-membered fused bicyclic group, an 11- to 14-membered fused tricyclic group, which may be optionally substituted with one or more substituents independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;
$R^{22}$ is selected from alkyl, aryl, aralkyl, cycloalkyl and C(O)R';
$X^1$ is selected from C—$R^1$ and N;
$X^2$ is selected from C—$R^2$ and N;
$X^3$ is selected from C—$R^3$ and N;
$R^1$, $R^2$, and $R^3$ are independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;

alternatively, $R^1$ and $R^2$, or $R^2$ and $R^3$ taken together form a 5- or 6-membered cyclic group, an 8- to 10-membered fused bicyclic group, an 11- to 14-membered fused tricyclic group, which may be optionally substituted with one or more substituents independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;

additionally or alternatively, $R^1$ and $R^6$ taken together form a 5- or 6-membered cyclic group, or an 8- to 10-membered fused bicyclic group;

additionally or alternatively, $R^3$ and $R^4$ taken together form a 5- or 6-membered cyclic group, or an 8- to 10-membered fused bicyclic group;

each R' is independently selected from H, alkyl, alkenyl, alkynyl, aralkyl, aryl and heteroaryl;

each R" is independently selected from H, alkyl, alkenyl, alkynyl and aralkyl;

n is 1 or 2; and m is 0 to 3, wherein when n is 1, m is 1 to 3, and when n is 2, m is 0.

In certain preferred embodiments of the emissive material of formula III, at least one of $Y^1$ and $Y^2$ is N. In particularly preferred embodiments, $R^{12}$ is further selected to be an aryl group.

In certain preferred embodiments of the emissive material of formula III, at least one of $Z^1$ and $Z^2$ is N. In particularly preferred embodiments, $R^{22}$ is further selected to be an aryl group.

In other preferred embodiments of the emissive material of formula III, $Y^1$ and $Y^2$ are C—$R^4$ and C—$R^5$, respectively, and $R^4$ and $R^5$ taken together form an 8- to 10-membered fused bicyclic group, or an 11- to 14-membered fused tricyclic group, which may be optionally substituted with one or more substituents independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl.

In other preferred embodiments of the emissive material of formula III, $Z^1$ and $Z^2$ are C—$R^6$ and C—$R^7$, respectively, and $R^6$ and $R^7$ taken together form an 8- to 10-membered fused bicyclic group, or an 11- to 14-membered fused tricyclic group, which may be optionally substituted with one or more substituents independently selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl.

In a further embodiment of the invention, the emissive material has the formula IV:

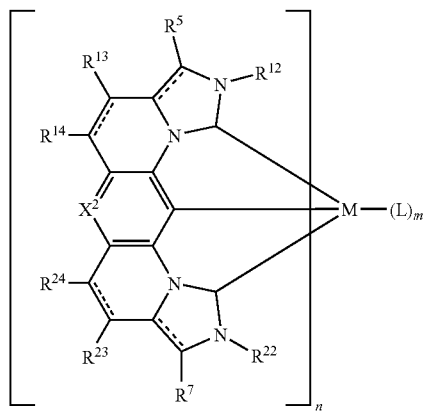

(IV)

wherein:

M is a second or third row transition metal;

dotted lines represent optional double bonds;

$X^2$ is selected from C—$R^2$ or N;

$R^2$ is selected from H, alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;

$R^5$ is selected from H, alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;

$R^7$ is selected from H, alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;

$R^{12}$ is selected from alkyl, aryl, aralkyl, cycloalkyl and C(O)R';

$R^{13}$ and $R^{14}$ are independently selected from H, alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;

additionally or alternatively $R^{13}$ and $R^{14}$ form a fused 5- or 6-membered cyclic group, wherein the fused cyclic group is optionally substituted with one of more substituents selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;

$R^{22}$ is selected from alkyl, aryl, aralkyl, cycloalkyl and C(O)R';

$R^{23}$ and $R^{24}$ are independently selected from H, alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;

additionally or alternatively $R^{23}$ and $R^{24}$ form a fused 5- or 6-membered cyclic group, wherein the fused cyclic group is optionally substituted with one of more substituents selected from alkyl, alkenyl, alkynyl, aralkyl, O—R', N(R')$_2$, SR', C(O)R', C(O)OR', C(O)NR'$_2$, CN, CF$_3$, NO$_2$, SO$_2$R', SOR', SO$_3$R', Si(R")$_3$, halo, aryl and heteroaryl;

each R' is independently selected from H, alkyl, alkenyl, alkynyl, aralkyl, aryl and heteroaryl;

and each R" is independently selected from H, alkyl, alkenyl, alkynyl and aralkyl.

In preferred embodiments of the invention, each of $X^1$, $X^2$ and $X^3$ are selected to be C—$R^1$, C—$R^2$, C—$R^3$, respectively.

Preferred substituents off of the aryl and heteroaryl groups include CF$_3$, CN, CH$_3$, F, and phenyl. In preferred embodiments, the substituent $R^2$ is selected from CF$_3$, CN, CH$_3$, F, and phenyl, with CF$_3$ and CN being particularly preferred.

In a preferred embodiment of the invention, the device comprises an emissive material selected from Set 1, Set 2, or Table 1, which provides Density Function Theory (DFT) calculations using the G98/B31 yp/cep-31 g basis set to obtain estimates of the HOMO, LUMO, HOMO-LUMO gap, singlet energy S1, and triplet energy T1 for various compounds of the present invention.

Set 1
Os1a
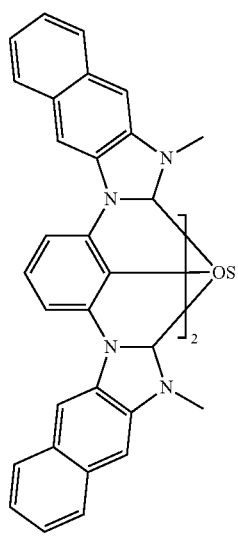
Os2a
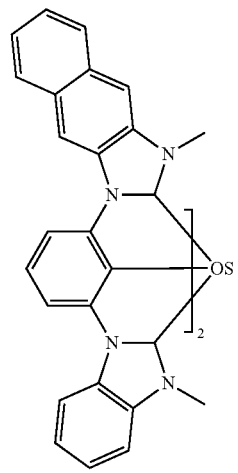
Os3
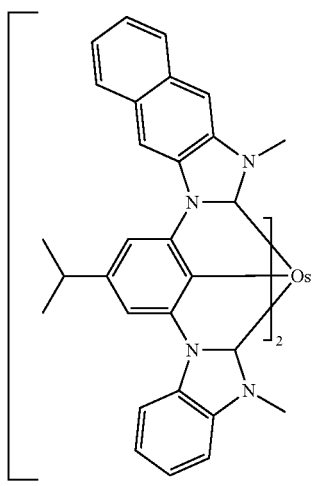
Os4
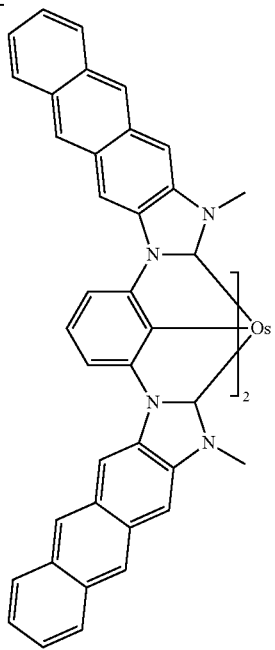
Os5
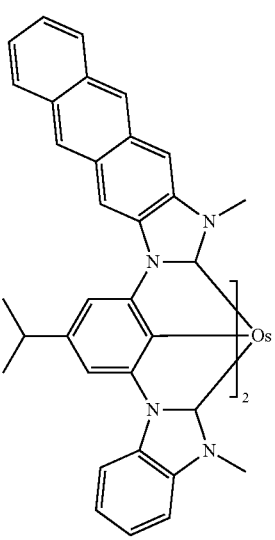
Os6
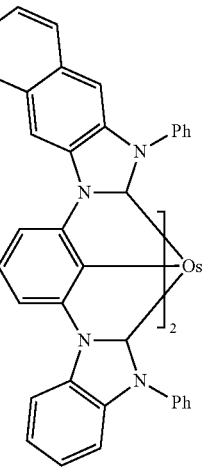

29
-continued
Os6
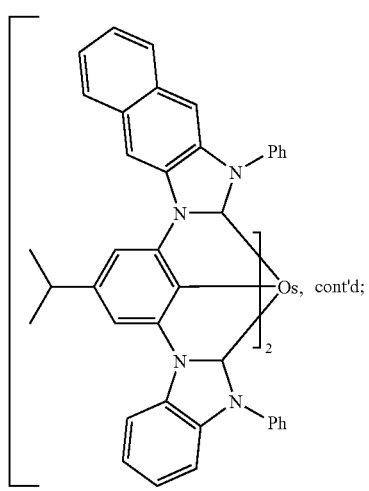
Os7
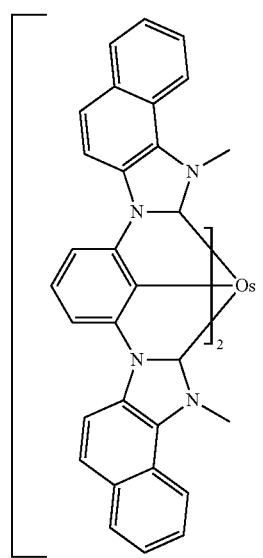
Os8
30
-continued
Os9
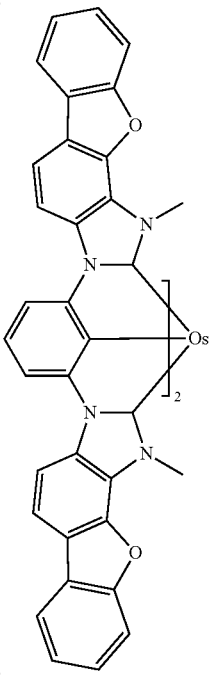
Os10
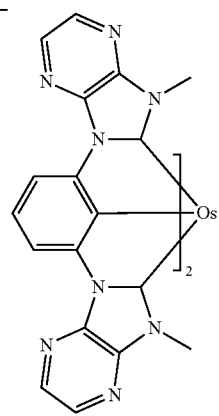
Os10
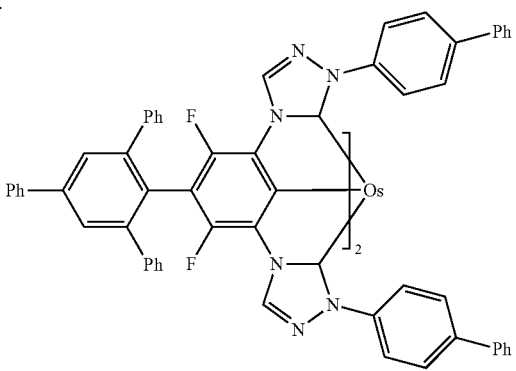

| | |
|---|---|
| Os12 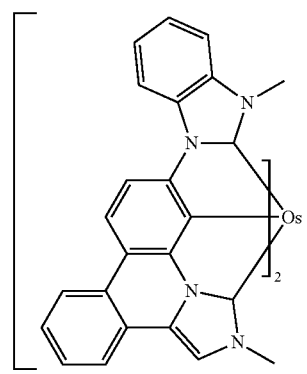 | Os15 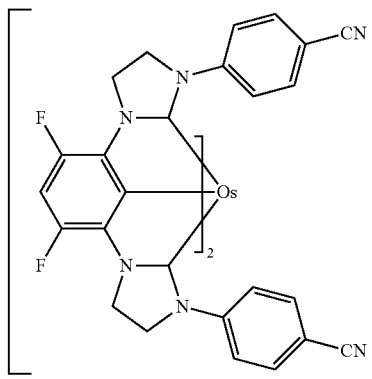 |
| Os13 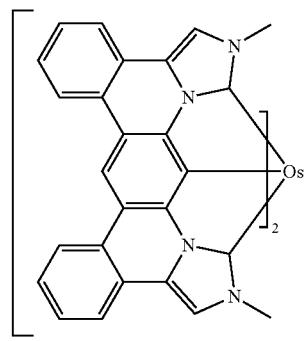 | Os16 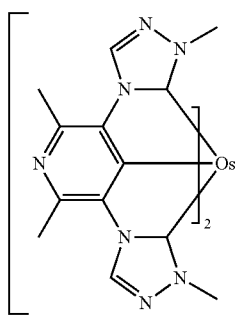 |
| Os13 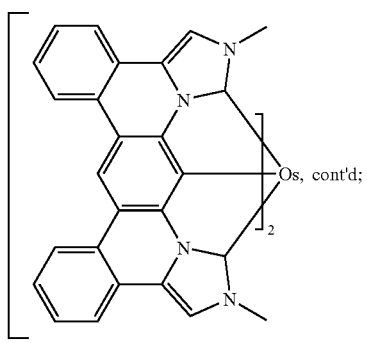 | Os17 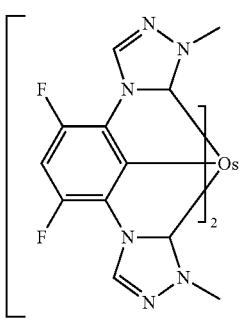 |
| Os14 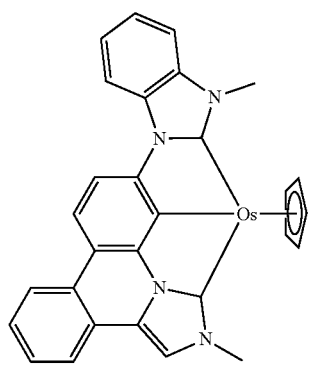 | Os18 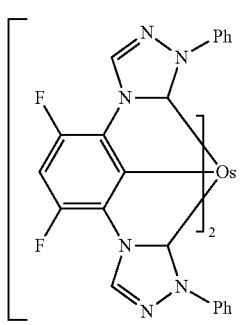 |
| | Os18 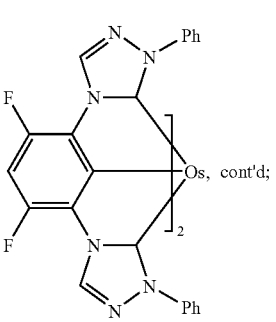 |

Os19 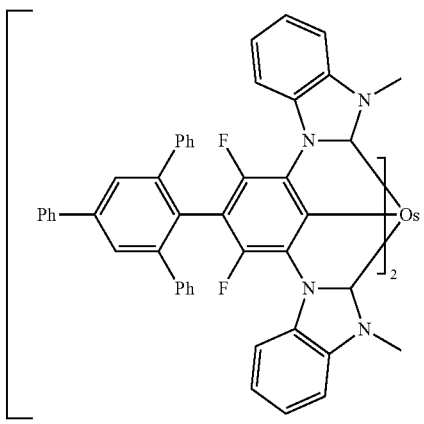
Os20 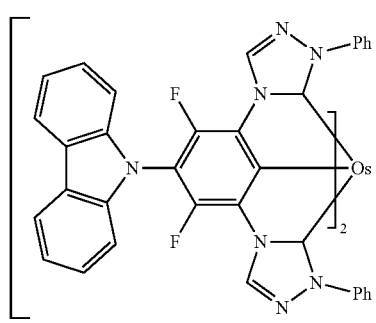
Os21 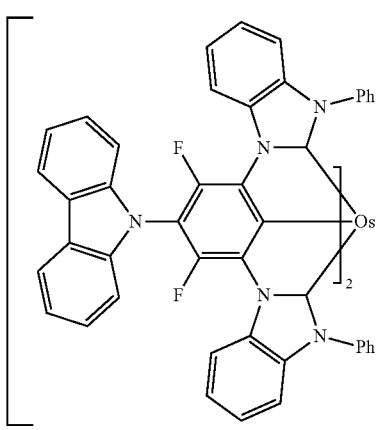
Os22 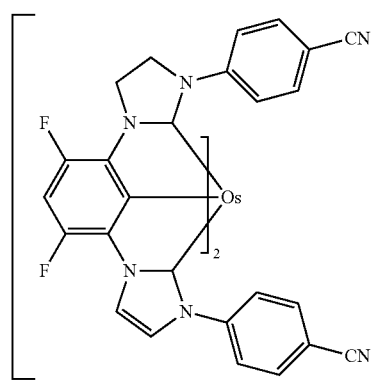
Os22 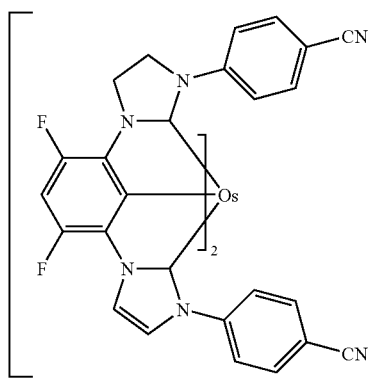
Os23 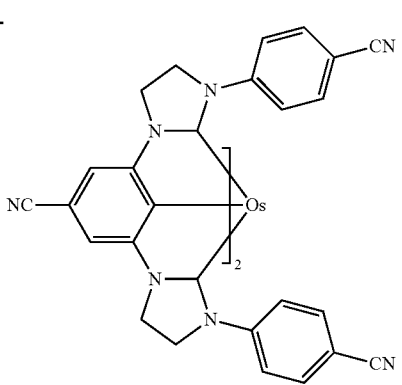
Os24 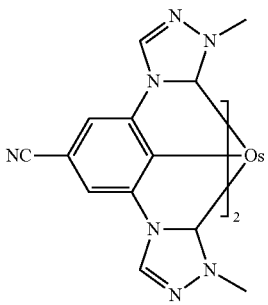
Os25 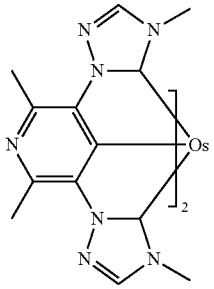

Os26
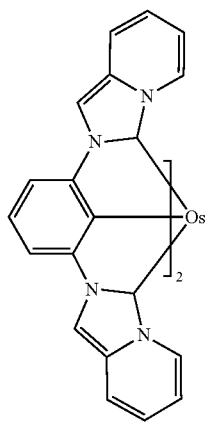
Os26
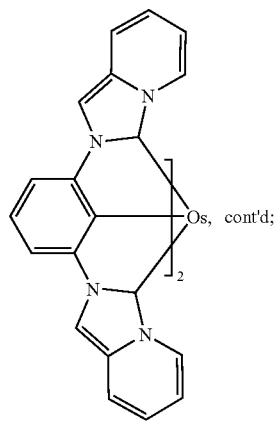
Os, cont'd;
Os27
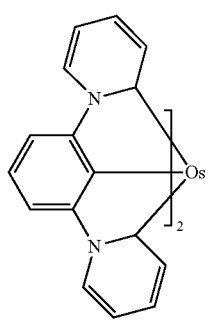
Os28
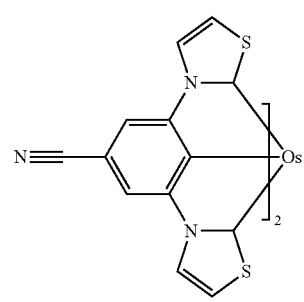
Os29
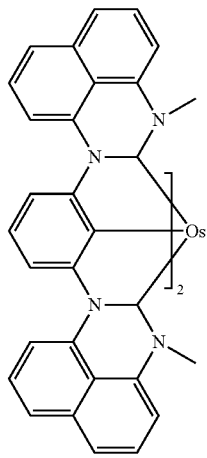
Os29
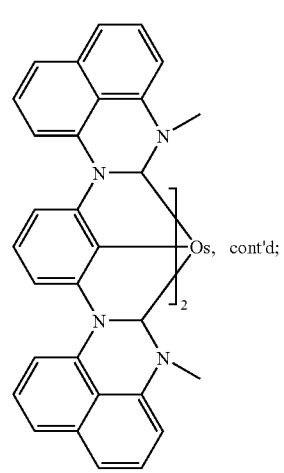
Os, cont'd;
Set 2
es-1
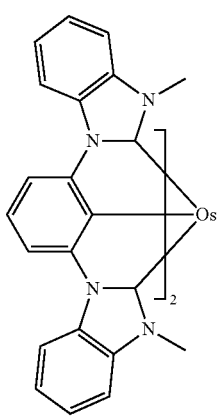

-continued
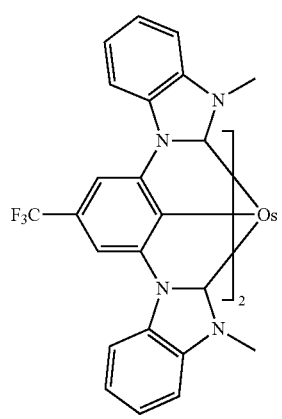
es-2
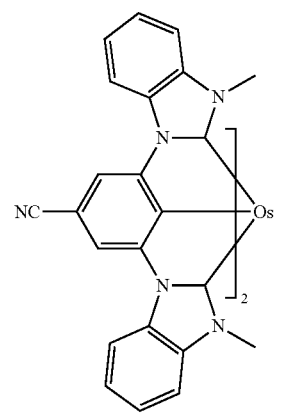
es-3
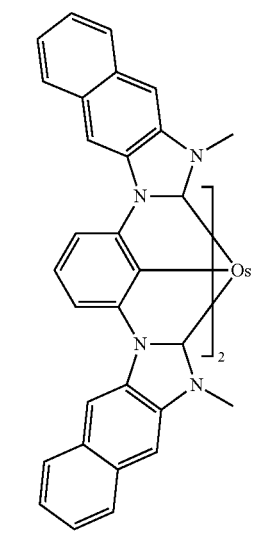
es-4
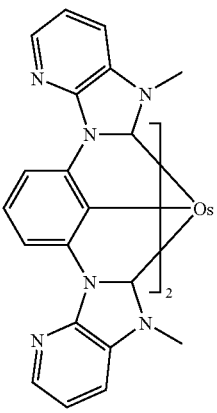
es-5
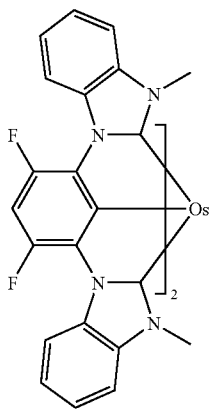
es-6
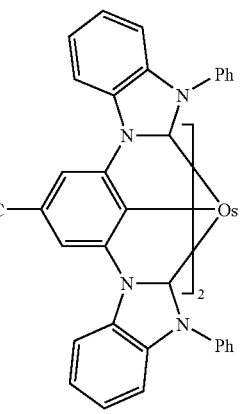
es-7
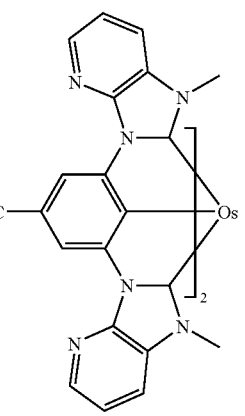
es-8 es-9
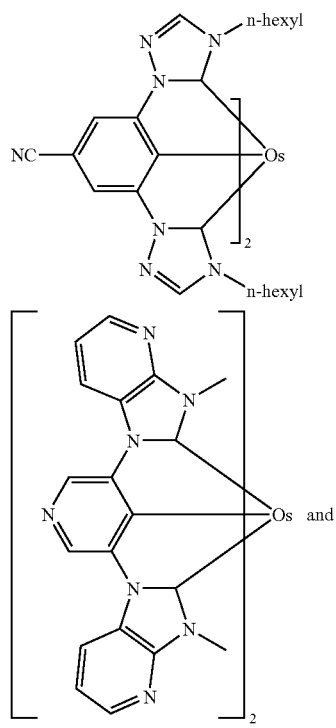
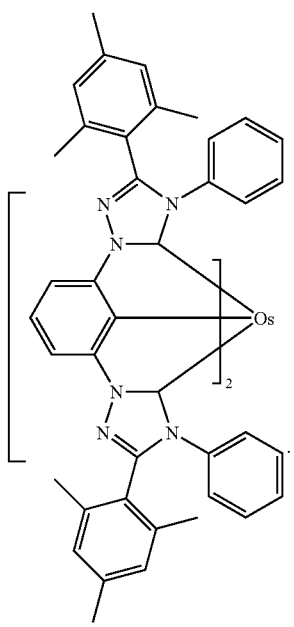
TABLE 1
| | Density Functional Theory Calculations (using Gaussian98/B31yp/cep-31 g); | | | | | |
|---|---|---|---|---|---|---|
| Entry | Compounds | Cal. HOMO (ev) | Cal. LUMO (ev) | Cal. Gap (ev) | Cal. S1 (intensity) (nm) | Cal. T1 (nm) |
| | | −3.89 | −0.11 | 3.79 | 412 | 451 |
| | | −4.65 | −0.87 | 3.78 | 397 | 448 |

TABLE 1-continued

Density Functional Theory Calculations (using Gaussian98/B31yp/cep-31 g);

| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
| | (structure) | −4.32 | −0.68 | 3.64 | 437 | 469 |
| | (structure) | −4.21 | −0.70 | 3.52 | 440 | 482 |
| | (structure) | −4.99 | −1.11 | 3.88 | 411 | 441 |

TABLE 1-continued

Density Functional Theory Calculations (using Gaussian98/B31yp/cep-31 g);

| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
| | [structure] | −4.09 | −0.76 | 3.33 | 471 | 496 |
| | [structure] | −4.12 | −0.62 | 3.50 | 431 | 462 |
| | [structure] | −5.44 | −1.54 | 3.90 | 390 | 432 |

TABLE 1-continued
Density Functional Theory Calculations (using Gaussian98/B31yp/cep-31 g);
| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
| | 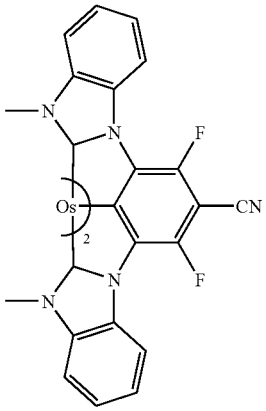 | −5.45 | −1.37 | 4.08 | 396 | 460 |
| | 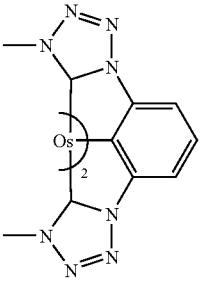 | −5.37 | −1.93 | 3.43 | 442 | 491 |
| | 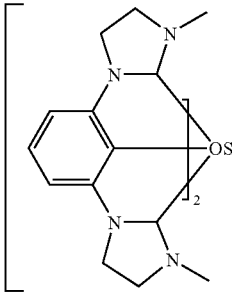 | −3.53 | 0.65 | 4.18 | 399 | 440 |
| | 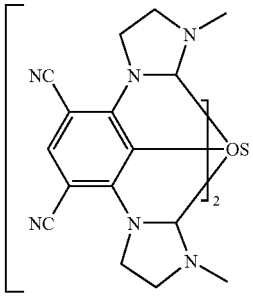 | −4.82 | −1.33 | 3.48 | | |

TABLE 1-continued

Density Functional Theory Calculations (using Gaussian98/B31yp/cep-31 g);

| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
|  | [Os complex with bis(N-methylbenzimidazole) and CN-substituted phenyl] | −4.97 | −1.15 | 3.83 | 428 | 458 |
|  | [Os complex with bis(N-methylbenzimidazole) and difluoro-substituted phenyl] | −4.86 | −0.87 | 3.99 | 395 | 434 |
|  | [Os complex with bis(N-methylbenzimidazole) and SiF$_3$-substituted phenyl] | −5.23 | −1.28 | 3.95 |  |  |

TABLE 1-continued

Density Functional Theory Calculations (using Gaussian98/B31yp/cep-31 g);

| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
| | [structure with Os, benzimidazole groups, F, and triazole] | −5.42 | −1.33 | 4.09 | | |
| | [structure with Os, benzimidazole groups, F, and carbazole] | −5.05 | −1.04 | 4.01 | | |
| | [structure with Os, triazole groups, and F] | −5.32 | −1.24 | 4.08 | 381 | 405 |
| | [structure with Os, triazole groups, F, and CN] | −5.99 | −1.84 | 4.15 | 387 | 451 |

TABLE 1-continued

Density Functional Theory Calculations (using Gaussian98/B31yp/cep-31 g);

| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
| | (Os complex structure) | −5.01 | −0.88 | 4.13 | | |
| | (Ir complex structure) | −4.85 | −1.30 | 3.55 | | |
| | (Os complex with F substituents) | −4.46 | −1.07 | 3.40 | | |
| | (Os complex with Ph substituents) | −3.92 | −0.23 | 3.69 | | |

TABLE 1-continued

Density Functional Theory Calculations (using Gaussian98/B31yp/cep-31 g);

| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
| | *(structure)* | −5.20 | −1.21 | 3.99 | 405 | 432 |
| | *(structure)* | −5.22 | −1.45 | 3.77 | 430 | 448 |
| | *(structure)* | −4.70 | −1.39 | 3.31 | 446 | 462 |
| | *(structure)* | −4.53 | −0.86 | 3.66 | 434 | 466 |

TABLE 1-continued
Density Functional Theory Calculations (using Gaussian98/B31yp/cep-31 g);
| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
| | 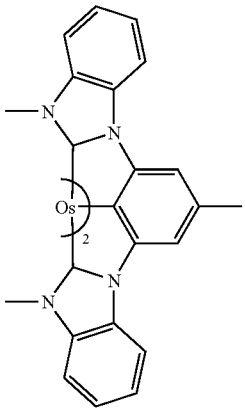 | −4.22 | −0.65 | 3.57 | 448 | 479 |
| | 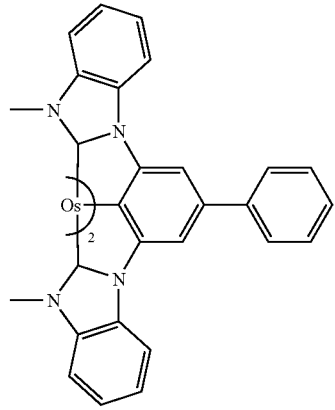 | −4.37 | −0.77 | 3.59 | 459 | 473 |
| | 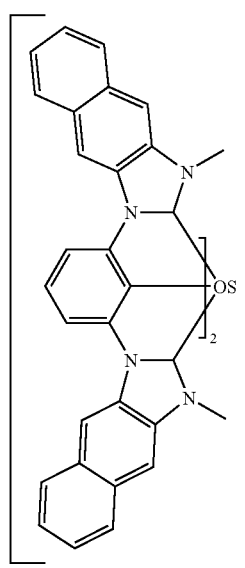 | −4.49 | −1.42 | 3.06 | 511 | 573 |

TABLE 1-continued

Density Functional Theory Calculations (using Gaussian98/B31yp/cep-31 g);

| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
| | *[structure]* | −4.15 | −0.88 | 3.27 | 487 | 545 |
| | *[structure]* | −4.06 | −0.99 | 3.06 | 521 | 587 |
| | *[structure]* | −3.99 | −0.93 | 3.06 | 524 | 578 |

TABLE 1-continued
Density Functional Theory Calculations (using Gaussian98/B31yp/cep-31 g);
| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
|  | 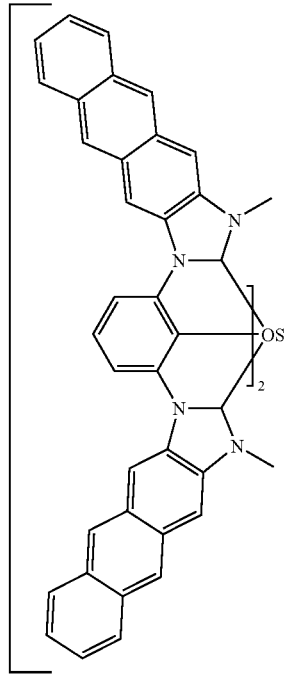 | −4.55 | −1.94 | 2.62 | 613 | 858 |
|  |  | −4.45 | −1.86 | 2.59 | 592 | 851 |

TABLE 1-continued

Density Functional Theory Calculations (using Gaussian98/B31yp/cep-31 g);

| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
| | [structure] | −4.41 | −1.34 | 3.07 | 502 | 562 |
| | [structure] | −5.22 | −2.13 | 3.09 | 490 | 521 |
| | [structure] | −5.13 | −1.94 | 3.18 | 484 | 533 |

TABLE 1-continued
Density Functional Theory Calculations (using Gaussian98/B31yp/cep-31 g);
| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
| | 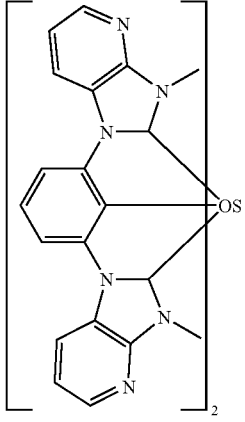 | −4.63 | −1.30 | 3.33 | 473 | 513 |
| | 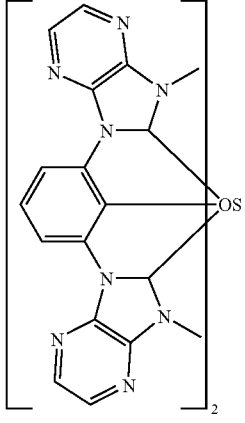 | −4.93 | −2.02 | 2.90 | 556 | 613 |
| | 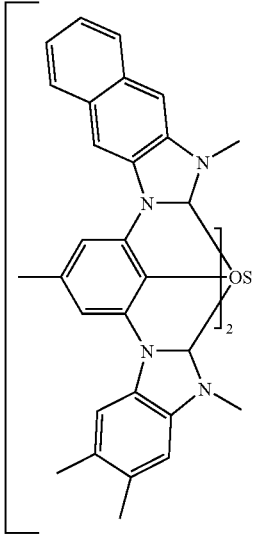 | −4.22 | −1.26 | 2.96 | 517 | 573 |

TABLE 1-continued
Density Functional Theory Calculations (using Gaussian98/B31yp/cep-31 g);
| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
| | 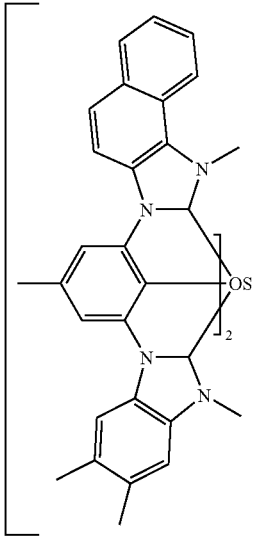 | −4.13 | −1.07 | 3.06 | 480 | 545 |
| | 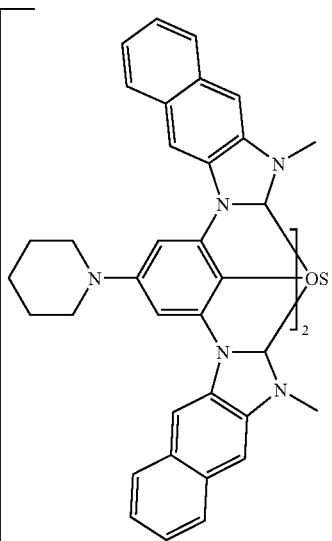 | −4.13 | −1.36 | 2.77 | 571 | 619 |

TABLE 1-continued

Density Functional Theory Calculations (using Gaussian98/B31yp/cep-31 g);

| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
| | [structure] | −4.76 | −0.92 | 3.83 | 426 | 462 |
| | [structure] | −4.81 | −1.16 | 3.65 | 439 | 461 |
| | [structure] | −4.48 | −1.26 | 3.22 | 492 | 538 |

TABLE 1-continued

Density Functional Theory Calculations (using Gaussian98/B31yp/cep-31 g):

| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
|  |  | −4.39 | −0.99 | 3.40 | 455 | 506 |
|  |  | −4.78 | −1.62 | 3.15 | 454 | 542 |
|  |  | −5.33 | −2.06 | 3.27 | 474 | 561 |
|  |  | −5.87 | −2.64 | 3.22 | 480 | 569 |

TABLE 1-continued

Density Functional Theory Calculations (using Gaussian98/B31yp/cep-31 g);

| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
| | *(structure)* | −4.78 | −1.08 | 3.70 | 441 | 458 |
| | *(structure)* | −5.22 | −1.25 | 3.97 | 406 | 458 |
| | *(structure)* | −4.24 | −1.03 | 3.21 | 463 | 488 |

TABLE 1-continued
Density Functional Theory Calculations (using Gaussian98/B31yp/cep-31 g);
| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
| | 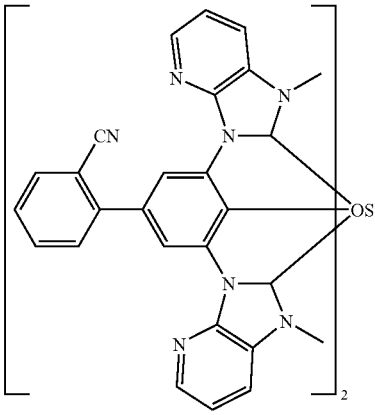 | −4.65 | −1.41 | 3.24 | 474 | 522 |
| | 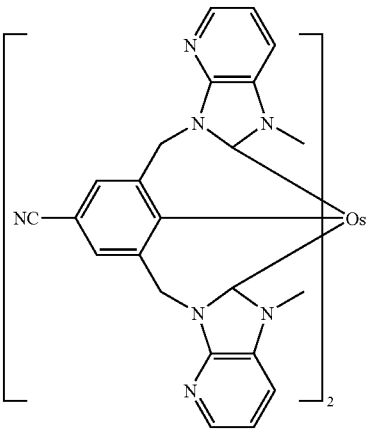 | −4.97 | −1.64 | 3.33 | 453 | 488 |
| | 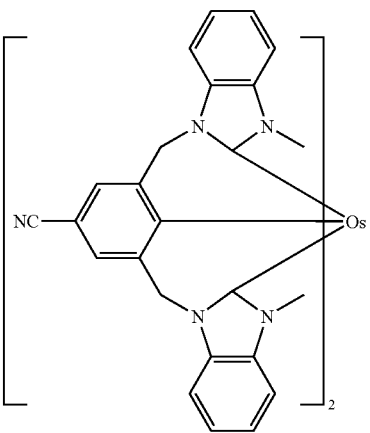 | −4.74 | −1.14 | 3.60 | 419 | 472 |

TABLE 1-continued

Density Functional Theory Calculations (using Gaussian98/B31yp/cep-31 g):

| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
| | | −4.91 | −1.69 | 3.22 | 513 | 524 |
| | | −4.76 | −1.50 | 3.26 | 474 | 519 |
| | | −5.01 | −1.34 | 3.68 | 107 | 473 |
| | | −5.96 | −3.21 | 2.75 | 595 | 624 |

TABLE 1-continued

Density Functional Theory Calculations (using Gaussian98/B31yp/cep-31 g):

| Entry | Compounds | Cal. HOMO (ev) | Cal. LUMO (ev) | Cal. Gap (ev) | Cal. S1 (intensity) (nm) | Cal. T1 (nm) |
|---|---|---|---|---|---|---|
| | [structure with NC-phenyl, triazole, Os complex] | −5.05 | −1.56 | 3.49 | 416 | 455 |
| | [Os bis-benzimidazole NO$_2$ complex, N-methyl] | −5.29 | −2.58 | 2.71 | 574 | 730 |
| | [Os bis-benzimidazole NO$_2$ complex, N-Ph] | −5.09 | −2.40 | 2.69 | 575 | 738 |

Preferred embodiments include osmium complexes which comprise two tridentate ligands each of which have a bond to the metal center from a carbenes and from an anionic phenyl ring.

The term "halo" or "halogen" as used herein includes fluorine, chlorine, bromine and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted with one or more substituents selected from halo, CN, CO$_2$R, C(O)R, NR$_2$, cyclic-amino, NO$_2$, and OR, wherein each R is independently selected from H, alkyl, alkenyl, alkynyl, aralkyl, aryl and heteroaryl.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted with one or more substituents selected from halo, CN, CO$_2$R, C(O)R, NR$_2$, cyclic-amino, NO$_2$, and OR.

The term "alkenyl" as used herein contemplates both straight and branched chain alkene radicals. Preferred alkenyl groups are those containing two to fifteen carbon atoms. Additionally, the alkenyl group may be optionally substituted with one or more substituents selected from halo, CN, CO$_2$R, C(O)R, NR$_2$, cyclic-amino, NO$_2$, and OR.

The term "alkynyl" as used herein contemplates both straight and branched chain alkyne radicals. Preferred alkyl groups are those containing two to fifteen carbon atoms. Additionally, the alkynyl group may be optionally substituted with one or more substituents selected from halo, CN, CO$_2$R, C(O)R, NR$_2$, cyclic-amino, NO$_2$, and OR.

The terms "aralkyl" as used herein contemplates an alkyl group that has as a substituent an aromatic group. Additionally, the aralkyl group may be optionally substituted on the aryl with one or more substituents selected from halo, CN, CO$_2$R, C(O)R, NR, cyclic-amino, NO$_2$, and OR.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperidino, pyrrolidino, and the like, and cyclic ethers, such as tetrahydrofuran, tetrahydropyran, and the like. Additionally, the heterocyclic group may be optionally substituted with one or more substituents selected from halo, CN, CO$_2$R, C(O)R, NR$_2$, cyclic-amino, NO$_2$, and OR.

The term "aryl" or "aromatic group" as used herein contemplates single-ring groups and polycyclic ring systems. The polycyclic rings may have two or more rings in which two carbons are common by two adjoining rings (the rings are "fused") wherein at least one of the rings is aromatic, e.g., the other rings can be cycloalkyls, cycloalkenyls, aryl, heterocycles and/or heteroaryls. Additionally, the aryl group may be optionally substituted with one or more substituents selected from halo, CN, CO$_2$R, C(O)R, NR$_2$, cyclic-amino, NO$_2$, and OR.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls, and include, for example, quinoline, isoquinoline, indole, carbazoles, etc. Additionally, the heteroaryl group may be optionally substituted with one or more substituents selected from halo, CN, CO$_2$R, C(O)R, NR$_2$, cyclic-amino, NO$_2$, and OR.

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting. For example, theories relating to charge transfer are not intended to be limiting.

Material Definitions:

As used herein, abbreviations refer to materials as follows:
CBP: 4,4'-N,N-dicarbazole-biphenyl
m-MTDATA 4,4',4"-tris(3-methylphenylphenlyamino)triphenylamine
Alq$_3$: 8-tris-hydroxyquinoline aluminum
Bphen: 4,7-diphenyl-1,10-phenanthroline
n-BPhen: n-doped BPhen (doped with lithium)
F$_4$-TCNQ: tetrafluoro-tetracyano-quinodimethane
p-MTDATA: p-doped m-MTDATA (doped with F$_4$-TCNQ)
Ir(ppy)$_3$: tris(2-phenylpyridine)-iridium
Ir(ppz)$_3$: tris(1-phenylpyrazoloto,N,C(2')iridium(III)
BCP: 2,9-dimethyl-4,7-diphenyl-1,10-phenanthroline
TAZ: 3-phenyl-4-(1'-naphthyl)-5-phenyl-1,2,4-triazole
CuPc: copper phthalocyanine.
ITO: indium tin oxide
NPD: N,N'-diphenyl-N—N'-di(1-naphthyl)-benzidine
TPD: N,N'-diphenyl-N—N'-di(3-toly)-benzidine
BAlq: aluminum(III)bis(2-methyl-8-hydroxyquinolinato)-4-phenylphenolate
mCP: 1,3-N,N-dicarbazole-benzene
DCM: 4-(dicyanoethylene)-6-(4-dimethylaminostyryl-2-methyl)-4H-pyran
DMQA: N,N'-dimethylquinacridone
PEDOT:PSS: an aqueous dispersion of poly(3,4-ethylenedioxytbiophene) with polystyrenesulfonate (PSS)
DTB 3,3'-di(triphenylen-2-yl)biphenyl
HIL4 fac-tris[2-(3-methyl-2-pyridinyl-κN)phenyl-κC]iridium(III)

Experimental:

Specific representative embodiments of the invention will now be described, including how such embodiments may be made. It is understood that the specific methods, materials, conditions, process parameters, apparatus and the like do not necessarily limit the scope of the invention.

Synthesis of Osmium Carbene Complex 1 (Os1)

Step 1: Os 1-A

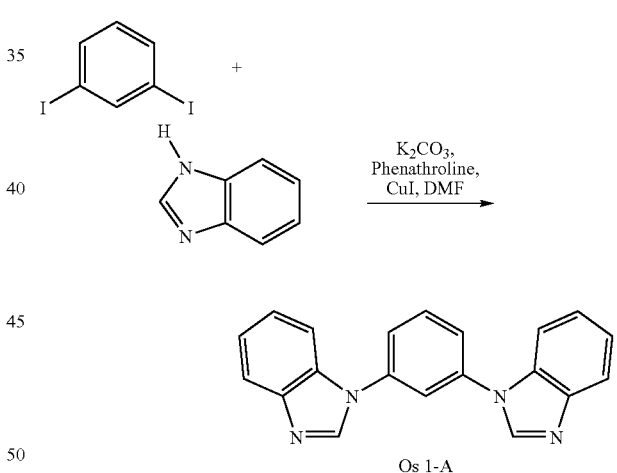

Os 1-A

A three neck 1000 mL round bottom flask was charged with 19.1 g of benzimidazole, 25.0 g of 1,3-diiodobenzene, 1.46 g of copper (I) iodide, 44.7 g of potassium carbonate, 2.77 g of 1,10-phenanthroline, and 500 mL of anhydrous N,N-dimethylformamide. The reaction mixture was heated to reflux under nitrogen for 2 days. After cooling to room temperature the reaction was filtered and the solvent removed from the filtrate by rotary evaporation. The crude product was purified by silica gel column chromatography using 95% dichloromethane/methanol as the eluent. The fractions containing the desired material were combined and the solvent removed by rotary evaporation. The product was crystallized from a dichloromethane/ethyl acetate mixture. The product (18 g) was collected by vacuum filtration as a white solid.

Step 2: Os 1-B

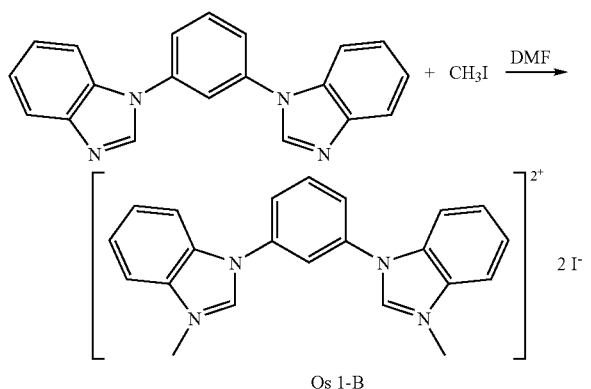

Os 1-B

A 1000 mL round bottom flask was charged with 15 g of Compound A, 30 g of iodomethane, and 400 mL of N,N-dimethylformamide. The mixture was heated to approximately 60° C. for 18 hours. The mixture was filtered and the solids were washed with ethyl acetate. The solids were then slurried in 400 ml of refluxing methanol, cooled, and then filtered to yield 20 g of the desired product as a white solid.

Step 3: OsH$_4$(PPh$_3$)$_3$

A 1000 mL three neck round bottom flask was charged with 3.6 g of triphenylphosphine and 100 ml of ethanol. The mixture is heated to reflux and 1.0 g of ammonium hexachloroosmate was added. A solution of 0.43 g of sodium borohydride in 50 ml of ethanol is then added dropwise. The reaction is refluxed for 30 minutes and then cooled to room temperature. The off white solids are collected by vacuum filtration. The solids were washed successively with ethanol, water, ethanol, and hexane.

Step 4: Os 1

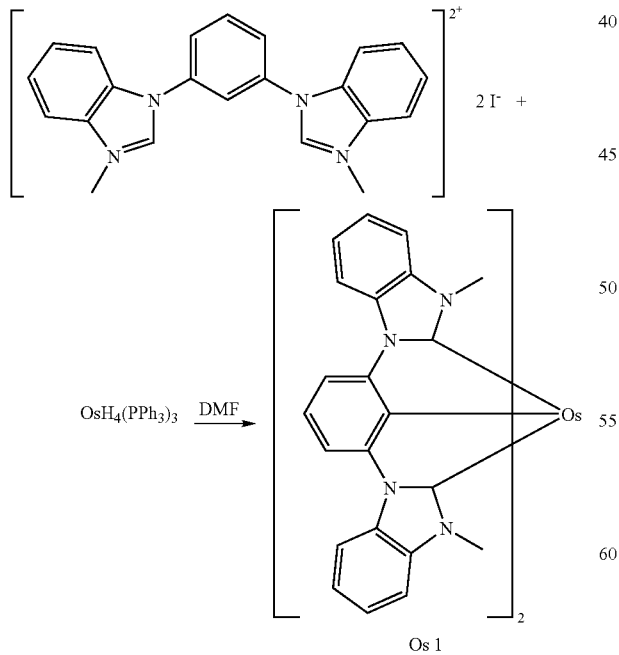

Os 1

A 250 ml three neck round bottom flask was charged with 4.0 g of compound B, 3.3 g of OsH$_4$(PPh$_3$)$_3$, and 125 mL of N,N-dimethylformamide. The mixture was heated to reflux for 20 hours under nitrogen. The solvent was removed by rotary evaporation and the crude product was purified by silica gel column chromatography using 80% hexanes/ethyl acetate as the eluent. The fractions containing the desired product were combined and the solvent removed by rotary evaporation. The product was crystallized from an ethyl acetate/hexane mixture. The product was confirmed by mass spectroscopy and $^1$H NMR.

Figure 3:
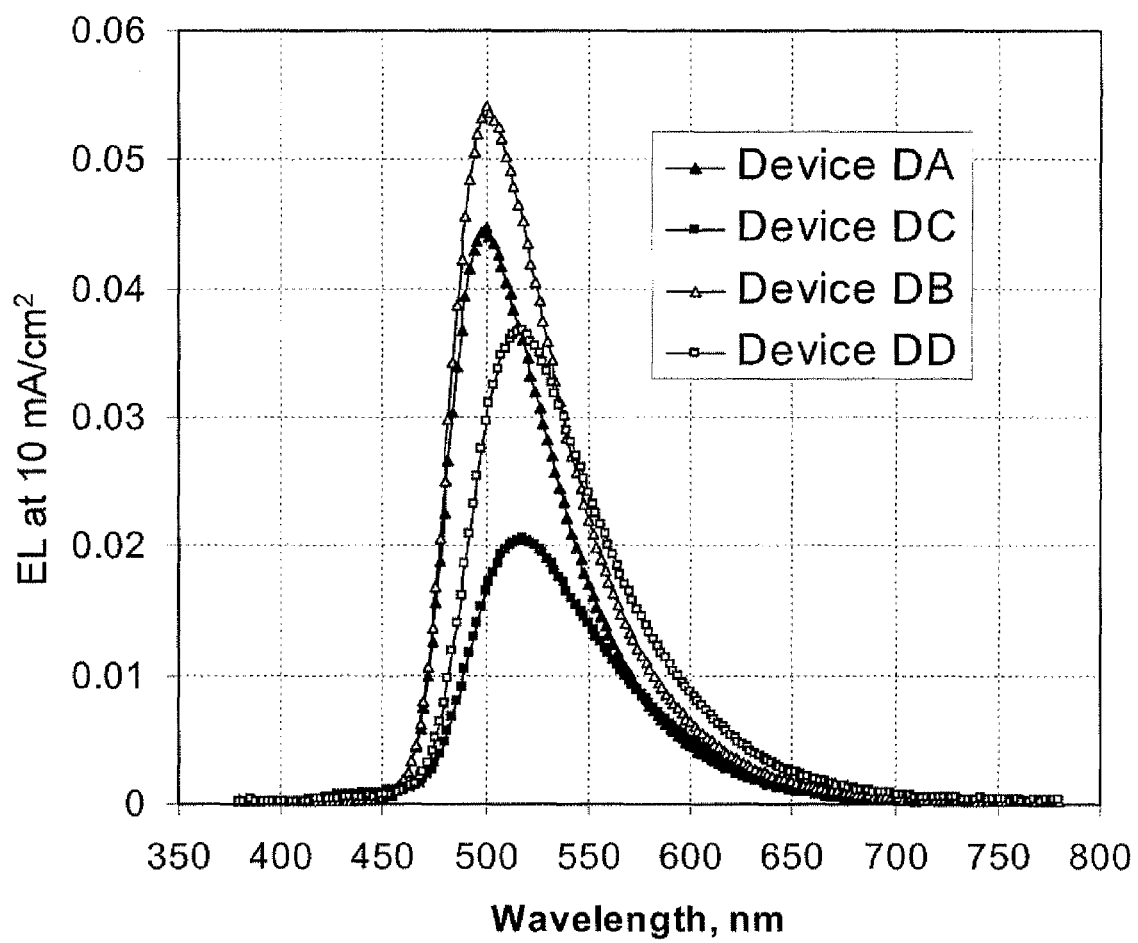
FIG. 3 shows the electroluminescent spectra (in arbitrary units) for devices DA, DB, DC and DD.

The emission spectra for Os 1 as a solution in toluene (degassed) at room temperature is shown in FIG. 3.

Example 2

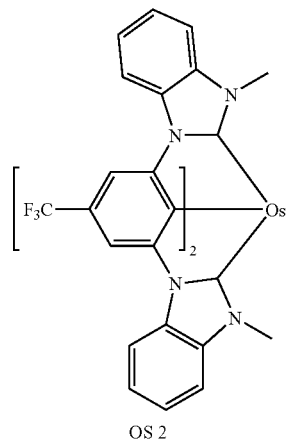

OS 2

Synthesis Osmium Carbene Complex OS2

Step 1

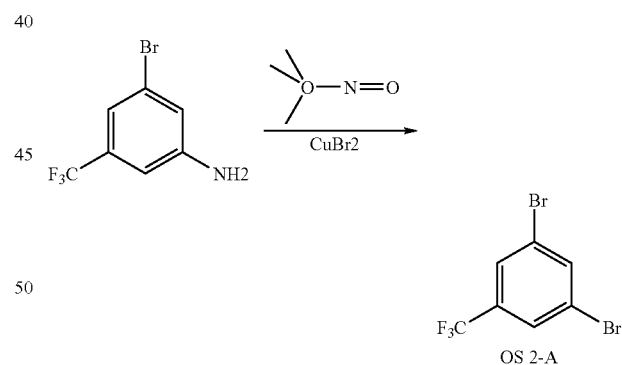

OS 2-A

To a Solution of CuBr$_2$ (26.8 g, 120 mmole) in anhydrous acetonitrile (500 ml) at 0° C. was added t-butyl nitrite (21.1 ml, 160 mmole) dropwise, and then 3-amino-5-bromobenzotrifluoride (25 g, 104.1 mmole) was added dropwise. The mixture was stirred at 0° C. for 1.5 h, then at room temperature for 16 h. The mixture was then concentrated to half of its original volume in vacuo, and then poured into 1 N HCl (620 ml). This mixture was extracted with ether (400 ml). The organic layer was washed with 1N HCl, dried (Na$_2$SO$_4$), filtered, and concentrated in vacuo. The residue was purified by flash column chromatography on silica gel using hexanes as the eluent and 18.33 g of OS 2-A was obtained. (57.8%)

Step 2

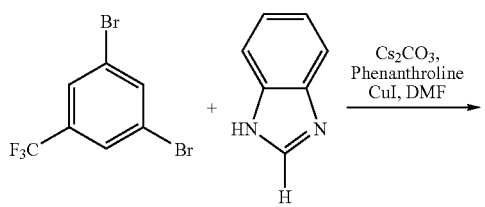

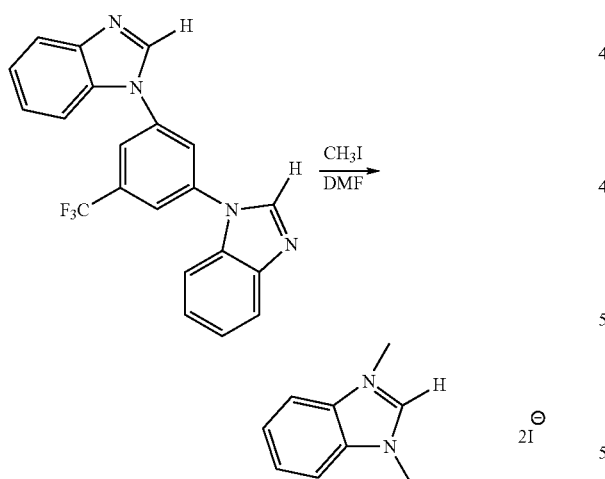

A 1000 mL round bottom flask was charged with 13.33 g of compound OS2-A, 12.43 g of benzimidazole, 1.668 g of copper (I) iodide, 3.15 g of 1,10-phenanthroline, 59.93 g of cesium carbonate, and 500 ml of N,N-dimethylformamide. The reaction mixture was heated to 150° C. under nitrogen for 60 hours. After cooling to room temperature; the reaction was filtered and the solvent was removed from the filtrate by rotary evaporation. The crude product was purified by silica gel column chromatography using 95% dichloromethane/ethyl acetate mixture. The product OS2-B (10 g, 60%) was collected by vacuum filtration as a white solid.

Step 3

A 1000 ml round bottom flask was charged with 8 g of compound OS2-C, 60 g of iodomethane and 50 ml of N,N-dimethylformamide. The mixture was heated to 41° C. for 70 hrs. 200 ml of toluene was added to induce the precipitation. The mixture was filtered and the solids were washed with ether to yield 9 g of OS2-C (64%).

Step 4

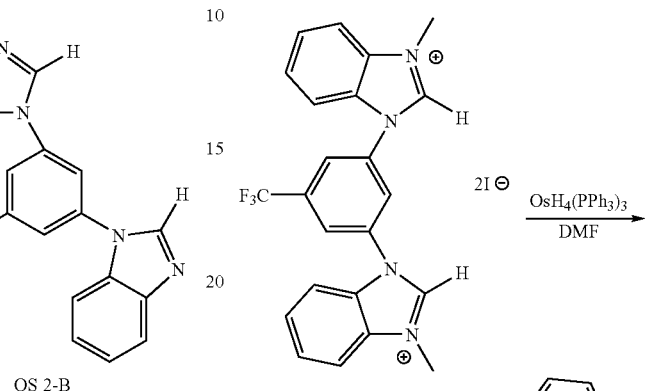

A 50 ml round bottom flask was charged with 310 mg of compound OS2-C, 230 mg of $OsH_4(PPh_3)_3$ and 35 ml of N,N-dimethylformamide. The mixture was heated to 150° C. for 3 hrs under nitrogen. The reaction mixture was dumped into water (150 ml) and extracted by ether. The ether was removed by rotary evaporation. The residue was purified by column chromatography ($SiO_2$, 80% hexanes/ethyl acetate) to yield OS2.

Figure 4:
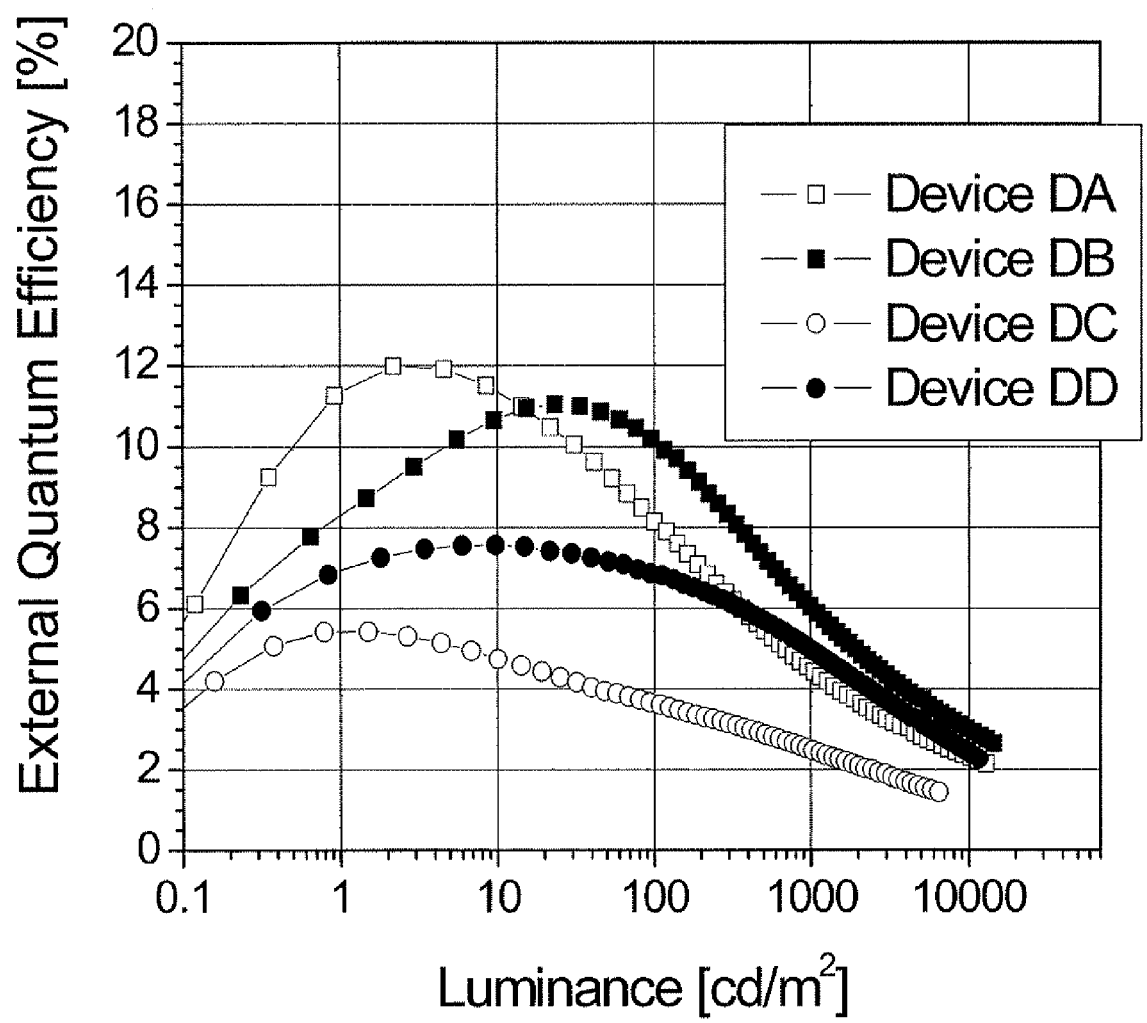
FIG. 4 shows the plots of external quantum efficiency vs. luminance for devices DA, DB, DC and DD.

The emission spectra for Os2 as a solution in toluene (degassed) at room temperature is shown in FIG. 4.

Example 3

Synthesis of es-4

A one neck 100 mL round bottom flask was charged with 15 g of 2,3 diaminonaphthalene and 30 ml of 99% formic acid. The mixture was heated to reflux for 3 hours. The mixture was extracted with ethyl acetate and water. The organic phase was discarded and the aqueous phase was neutralized with sodium hydroxide. The solid which formed was filtered and washed with water and isopropanol. The desired product was purified by vacuum distillation to yield 12 g of naphthamidazole as a white solid.

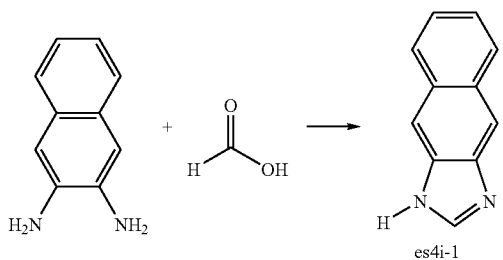

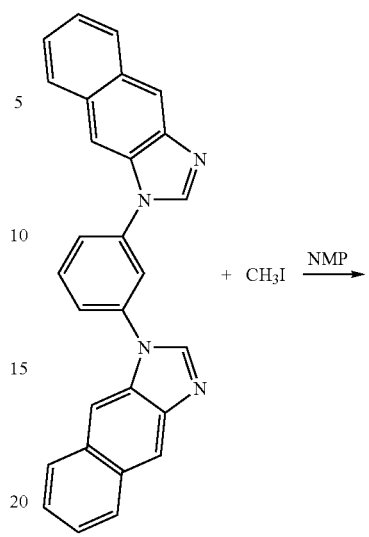

A three neck 500 mL round bottom flask was charged with 10 g of naphthamidazole, 8.9 g of 1,3-diiodobenzene, 0.56 g of copper (I) iodide, 17.2 g of potassium carbonate, 1.07 g of 1,10-phenathroline, and 200 mL of anhydrous N,N-dimethylformamide. The reaction mixture was heated to reflux under nitrogen for 18 hours. After cooling to room temperature the reaction was filtered. The solids were slurried in a water and isopropanol mixture. This mixture was then filtered and washed with isopropanol to yield 10 grams of a white solid. The desired product was confirmed by $^1$H NMR.

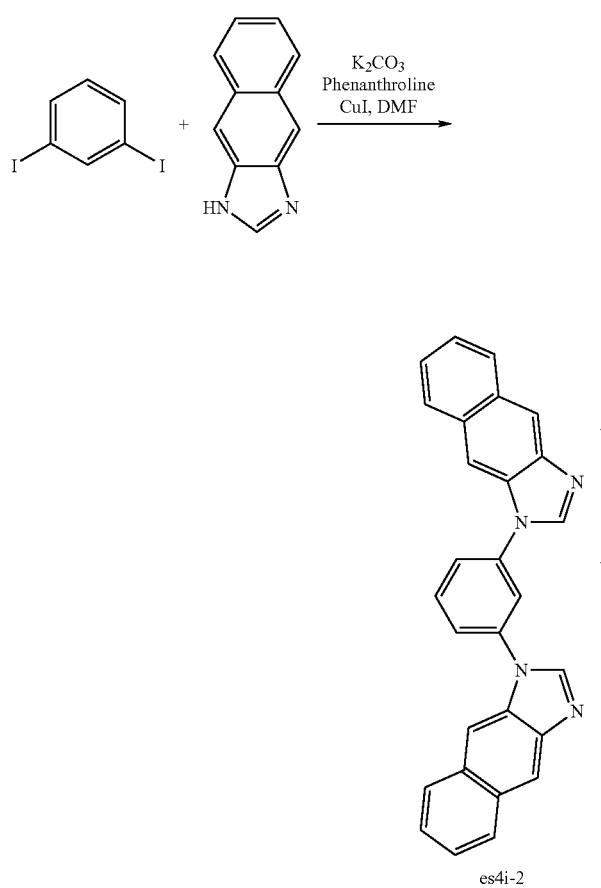

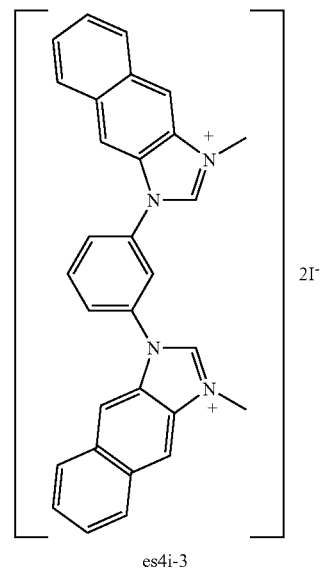

The product was then dissolved in 500 ml of NMP. About 30 g of iodomethane was added and the reaction was heated to about 80° C. for 36 h. The mixture was cooled and the solids were filtered and then washed with ethyl acetate to yield 13 g white solid.

A 1 L three neck round bottom flask was charged with 2.0 g of ammonium hexachloroosmate, 8.4 grams of triphenylphosphine, 120 mL of water, and 300 mL of tert-butylalcohol. The mixture was heated to reflux under nitrogen for 24 h. After cooling to room temperature, the reaction mixture was filtered and the solids were washed with water then ethanol. The green solids were air dried to yield 4.8 g OsCl$_2$(PPh$_3$)$_3$.

A 500 ml three neck round bottom flask was charged with 5 grams of silver oxide, 5.0 grams of es4i-3, and about 250 ml of anhydrous N,N-dimethylformamide. The mixture was heated to 60° C. for 1.5 hours under nitrogen. After cooling to room temperature, 3.75 g of OsCl$_2$(PPh$_3$)$_3$ was added to the flask. The mixture was heated to 100° C. for 18 hours and then heated at 120° C. for 6 h. Methylene chloride was added and the solids were filtered. Water was added to the filtrate and the water layer was extracted three times with methylene chloride. The combined organic fractions were dried over magnesium sulfate, filtered and concentrated under reduced pressure. The material was purified by silica gel column chromatography with 30% hexane/methylene chloride as the eluent. The desired fractions were combined and solvent removed to afford es-4, which was then crystallized from dichloromethane/hexanes.

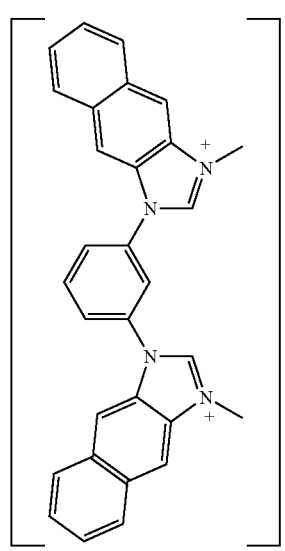

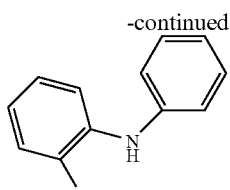

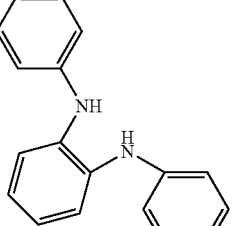

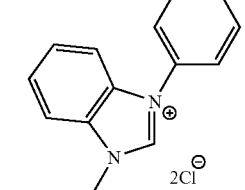

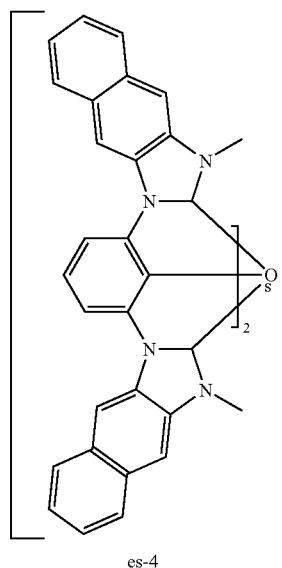

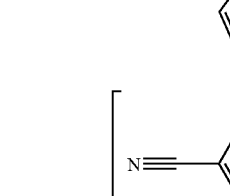

Example 4

Preparation of es-7

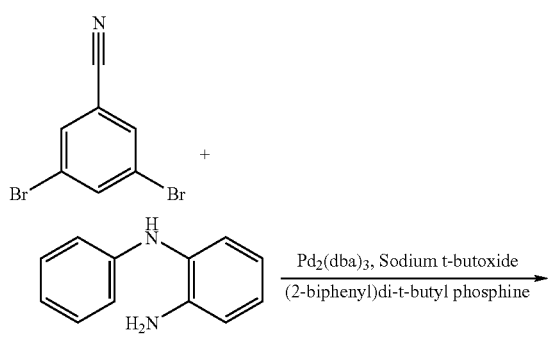

Step 1

A three neck flask was charged with 3,5-dibromobenzonitrile (1 g, 3.86 mmol), $N^1$-phenylbenzene-1,2-diamine (1.42 g, 7.72 mmol), $Pd_2(dba)_3$ (530 mg, 0.58 mmol), (2-biphenyl) di-t-butylphosphine, (345.5 mg, 1.158 mmol), sodium t-butoxide (1 g, 10.81 mmol) and anhydrous toluene (70 mL). The reaction mixture was stirred under nitrogen for 24 hrs in room temperature. The reaction mixture was cooled to 0 C by ice bath and a solution of 1M HCl (10.81 mL) in ether was added into reaction mixture. The reaction mixture was filtered and the precipitation was collected and used for next step without further purification.

Step 2

A 250 mL round bottom flask was charged with product from step 1 (1.8 g, 3.86 mmol), triethyl orthoformate (125 mL), conc. HCl (1 mL) and formic acid (several drops). The reaction was heated at 80 C for 16 h. The reaction mixture was concentrated under vacuum and the residue subjected to column chromatography (100% methylene chloride to 13% methanol in methylene chloride) to obtain the desired ligand salt (1.082 g, 50%).

Step 3

A 100 mL round bottom flask was charged with ligand (1.12 g, 2 mmol), silver oxide (1.39 g, 6 mmol), (PPh$_3$)$_3$OsCl$_2$ (1.048 g, 1 mmol) and anhydrous DMF (50 mL). The reaction was heated to 150 C under nitrogen for 1.5 h. The reaction mixture was filtered and the precipitation was washed with ethyl acetate. The filtrated was concentrated and subjected to column chromatography. (SiO$_2$, pretreated with triethylamine, 5% CH$_2$Cl$_2$ in hexanes to 50% CH$_2$Cl$_2$ in hexanes) to obtain es-7 (72 mg, 6%).

Example 5

Synthesis of es-8

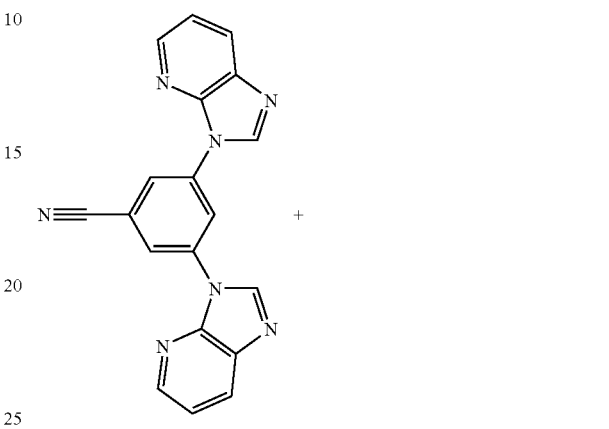

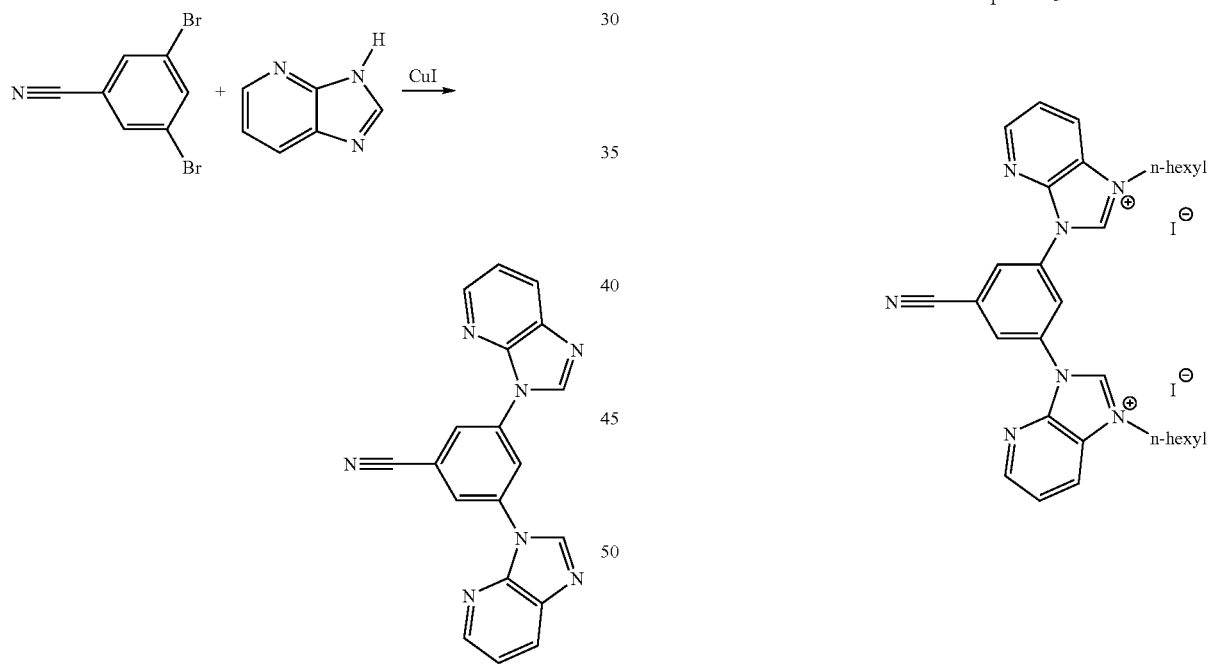

Into a 500 mL round bottom flask was placed 3,5-dibromobenzonitrile (10.0 grams, 38.3 mmol), 4-azabenzimidazole (10.96 grams, 92.0 mmol), copper (I) iodide (1.46 grams, 7.7 mmol), 1,10 phenanthroline (1.39 grams, 7.7 mmol) and potassium carbonate (11.1 grams, 80.4 mmol) and anhydrous dimethylformamide (100 mL). This was stirred at 125° C. for 20 h. The mixture was then cooled to ambient temperature and filtered. The solids were washed with 19:1 dichloromethane-methanol (50 mL). The filtrate was concentrated in vacuo and the crude product was chromatographed (silica gel) using a mobile phase of 19:1:0.1 dichloromethane-methanol-ammonium hydroxide to give 2.00 grams (15.5%) of the target compound as a pale pink solid. $^1$H nmr (DMSO-d6) δ 9.10 (s, 2H), 9.09 (t, 1H), 8.64 (s, 2H), 8.47 (d, 2H), 8.25 (d, 2H), 7.44 (dd, 2H). MS (EI+) 337.

A 250 mL round bottom flask was charged with 3,5-di(3H-imidazo[4,5-b]pyridine-3-yl)benzonitrile (2.35 grams, 6.97 mmol), anhydrous dimethylformamide (80 mL) and n-hexyl iodide (15.3 mL, 104.6 mmol). This was stirred at 150° C. for 20 h before being concentrated in vacuo. Ethyl acetate (100 mL) was added and the solid was filtered and recrystallized from methanol to give 3.83 grams (72%) of the ligand salt as a pale yellow powder. $^1$H nmr (DMF-d7) δ 11.0 (s, 2H), 9.50 (t, 1H), 9.03 (m, 3H), 8.92 (m, 2H), 4.93 (t, 4H), 2.20 (m, 4H), 1.56 (m, 4H), 0.88 (t, 6H). The ligand salt was converted to es-8 following a procedure similar to that used to prepare es-7.

Example 6

Synthesis of es-9

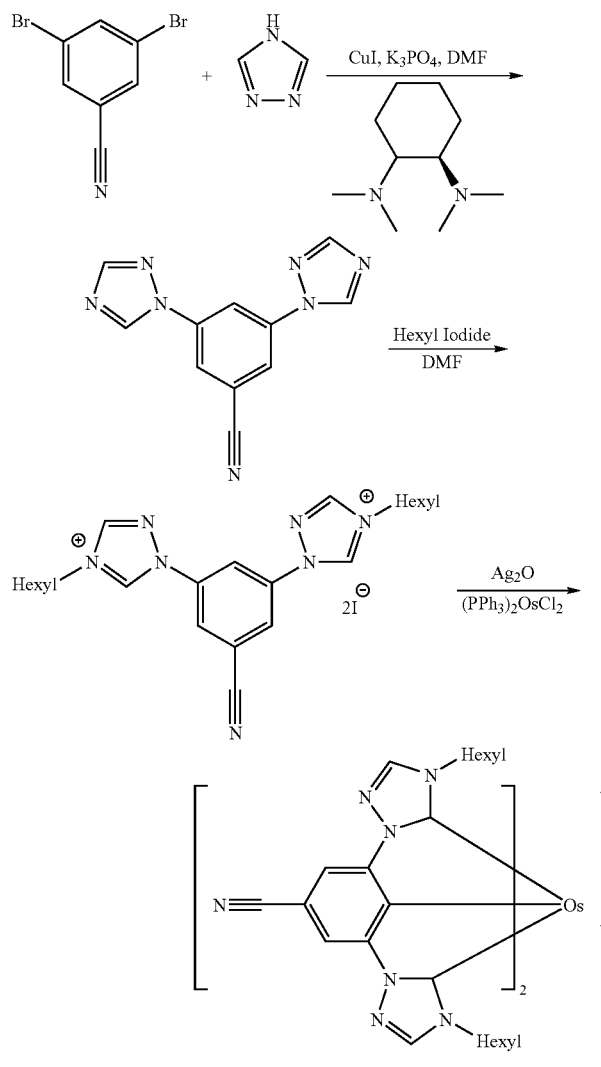

Step 1

A three neck flask was charged with 3,5-Dibromobenzonitrile (50 g, 0.19 mole), 1,2,4-Triazole (26.5 g, 0.38 mole), copper iodide (3.62 g, 0.019 mole), trans-N,N'-dimethylcyclohexane-1,2-diamine (5.4 g, 0.038 mole), potassium phosphate (anhydrous, 161.3 g, 0.76 mole), and anhydrous DMF (600 mL). The reaction mixture was stirred under nitrogen and heated at 110 C for 24 hours and then allowed to cool to room temperature. The solid was filtered and washed with DMF. The combined filtrate and washings were concentrated under vacuum. The residual solid was washed with ethyl acetate and purified by sublimation to give desired product.

Step 2

A 1 liter round bottom flask was charged with product from step 1 (16.2 g, 0.068 mole), 1-Iodohexane (144.2 g, 0.68 mole), and dry DMF (350 mL). The reaction mixture was heated in an oil bath at 150 C (bath temperature) for 18 hours. This was allowed to cool and concentrated under vacuum. The residual solid was re-crystallized from methanol to yield ligand (27.6 g, 62%).

Step 3

A 500 mL round bottom flask was charged with ligand (11.18 g, 16.89 mmole), silver oxide (7.83 g, 33.78 mmole), $(PPh_3)_3OsCl_2$ (8.85 g, 8.44 mmole) and anhydrous DMF (300 mL). The reaction was heated to 150 C under nitrogen for 1 h. The reaction mixture was filtered and the precipitation was washed with methylene chloride. The filtrated was concentrated and subjected to column chromatography. ($SiO_2$, pre-treated with triethylamine, 25% $CH_2Cl_2$ in hexanes to 50% $CH_2Cl_2$ in hexanes) to afford es-9 (910 mg, 22%).

Compounds es-1, es-2, es-3, es-5, and es-6 were prepared by procedures analogous to those given above for compounds es-4, es-7, es-8 and es-9.

Example 7

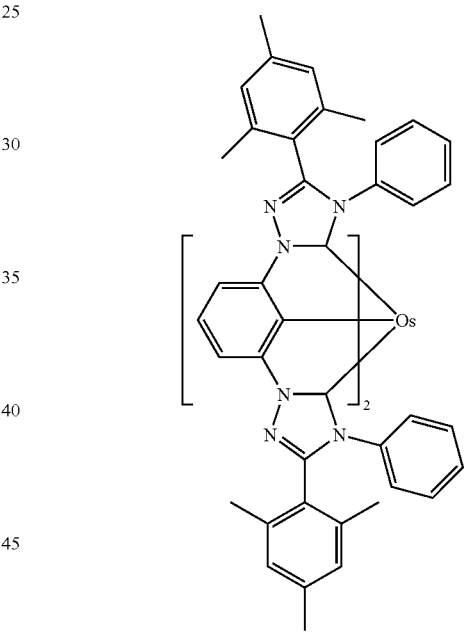

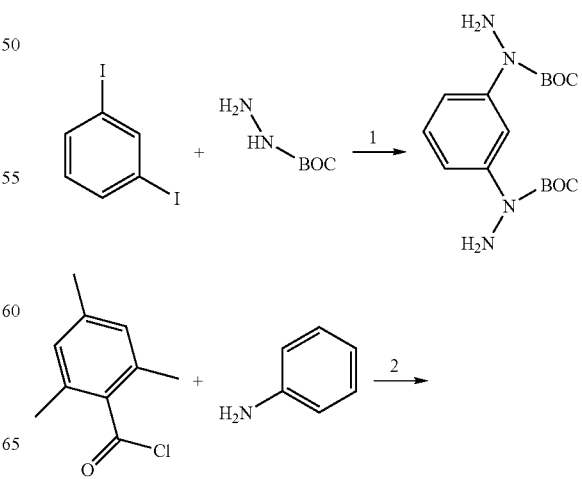

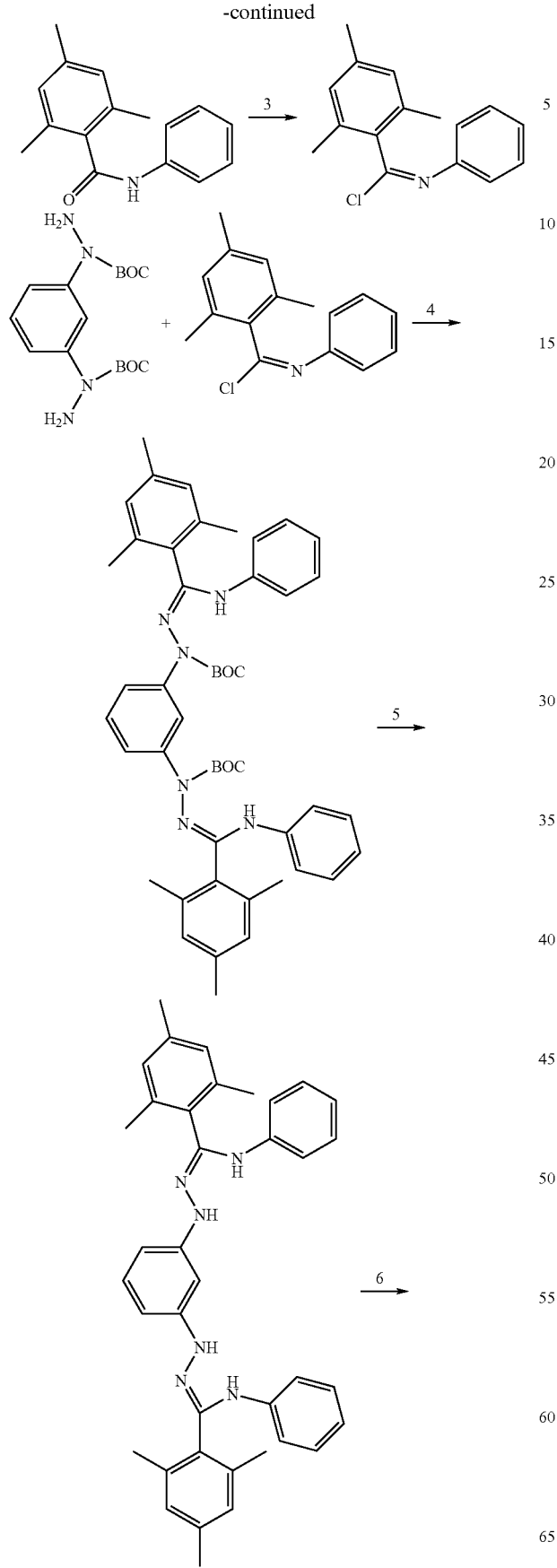
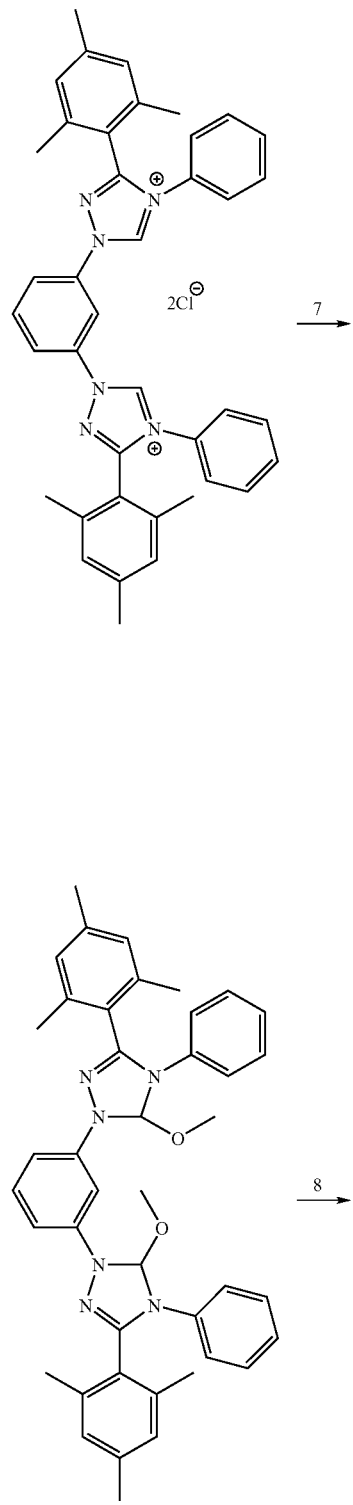

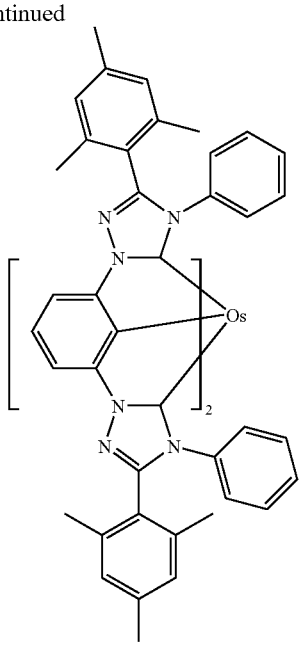

Step 1: A 500 ml three neck round bottom flask was charged with 1,3-diodobenzene (10 g, 0.03 mole), tert-butyl-carbazate (9.5 g, 0.072 mole), copper iodide (0.57 g, 0.003 mole), 1,10-phenanthroline (2.16 g, 0.012 mole), cesium carbonate (27.36 g, 0.084 mole) and 400 ml anhydrous DMF. The reaction mixture was heated to 80° C. for 21 hours. The reaction mixture was diluted with 400 ml of water and extracted with methylene chloride. The organic layer was concentrated to dryness and purified by column chromatography to yield the desired compound (11.3 g).

Step 2: A 500 ml three neck round bottom flask was charged with aniline (25.4 g, 0.27 mole), triethylamine (27.69 g, 0.27 mole) and 370 ml of THF. 50 g of 2,4,6-trimethyl benzoyl chloride was added dropwise at 0° C. The reaction mixture was stirred over night and yielded 60 g of the desired product.

Step 3: 2 g of the amide from Step 2 was dissolved in 7 ml of thionyl chloride and was heated at 78° C. for 1 hr. The reaction mixture was concentrated to dryness and used for the next step.

Step 4: The imidoyl chloride from Step 3 was dissolved in 5 ml of THF. A solution of the Boc-protected hydrazine (1.41 g, 4.179 mmole) and triethylamine (1.16 ml, 8.36 mmole) was added dropwise at −10° C. The reaction was then stirred at room temperature over night. The reaction mixture was diluted with methylene chloride and washed with 0.1N HCl and saturated sodium carbonate. The organic layer was concentrated to dryness and subjected to column chromatography to yield the desired compound (1.74 g).

Step 5: 1.74 g of the intermediate from Step 4 was dissolved in 4N HCl in dioxane; the mixture was stirred at room temperature for 2.5 hours. The reaction mixture was then evaporated to dryness and used for the next step.

Step 6: The intermediate from Step 5 was mixed with triethyl orthoformate (40 ml), HCl (2 ml) and a few drops of formic acid. The reaction mixture was heated to 80° C. over night. The reaction mixture was concentrated to ⅓ volume to induce precipitation. The reaction mixture was filtered to yield the desired product (1.1 g).

Step 7: 1 g of the intermediate from Step 6 was dissolved in anhydrous methanol (40 ml) and 0.5N sodium methoxide solution (6.53 ml, 3.26 mmole) was added and the product was filtered off (950 mg).

Step 8: A 500 ml three neck round bottom flask was charged with the ligand from Step 7 (6.64 g, 9.98 mmole), $Cl_2Os(PPh_3)_3$ (2.6 g, 2.49 mmole) and m-xylene (150 ml). The reaction mixture was fully degassed and heated to reflux over night. The reaction mixture was filtered and the filtrate was concentrated to dryness. The residue was subjected to column chromatography to yield 1.31 g of the Os complex.

Example 8

OLEDs comprising a phosphorescent emissive material according to the present invention may be fabricated according to procedures described by Lin et al. in U.S. patent application Ser. No. 11/241,981 and by Tung et al. in U.S. patent application Ser. No. 11/242,025.

The starting substrates were glass substrates coated with indium tin oxide (ITO) of 80 nm thickness and sheet resistance <25 ohms/square, purchased from Colorado Concept Coatings LLC. All subsequent thin films were deposited by thermal evaporation at a pressure of <$10^{-6}$ Torr. The cathode consisted of 10 Å of LiF followed by 1,000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package.

Prior to device fabrication, the substrates were cleaned by sonication in soap solution, rinsed with deionized water, and boiled in isopropanol. After the cleaning procedure, the substrates were dried under an $N_2$ flow followed by $O_2$ plasma and UV ozone treatments. Organic layers of the OLEDs were sequentially deposited by thermal evaporation from resistively heated alumina crucibles onto the substrates, at room temperature, at a base pressure of <$10^{-6}$ Torr. The rate of a single-component layer was controlled with one Inficon thickness monitor located close to the substrate. The specific rates for each material are given in Table 1 below. For the two-component emissive layer the rate of the dopant was controlled with an additional crystal monitor located close to the dopant evaporation source. The additional monitor was not exposed to the major flow of the host.

mCBP and HPT have the following structures, respectively:

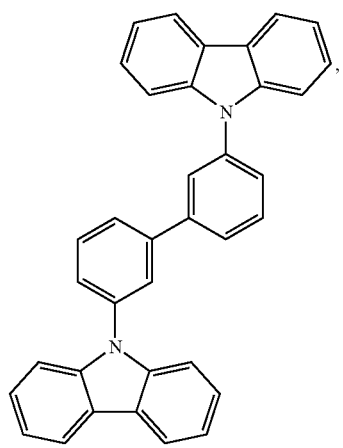

-continued

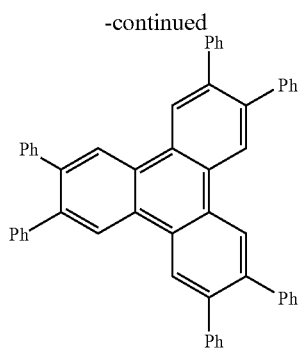

Devices were prepared having the following device structures set forth in Table 2. The dopant concentrations are in wt %.

Figure 5:
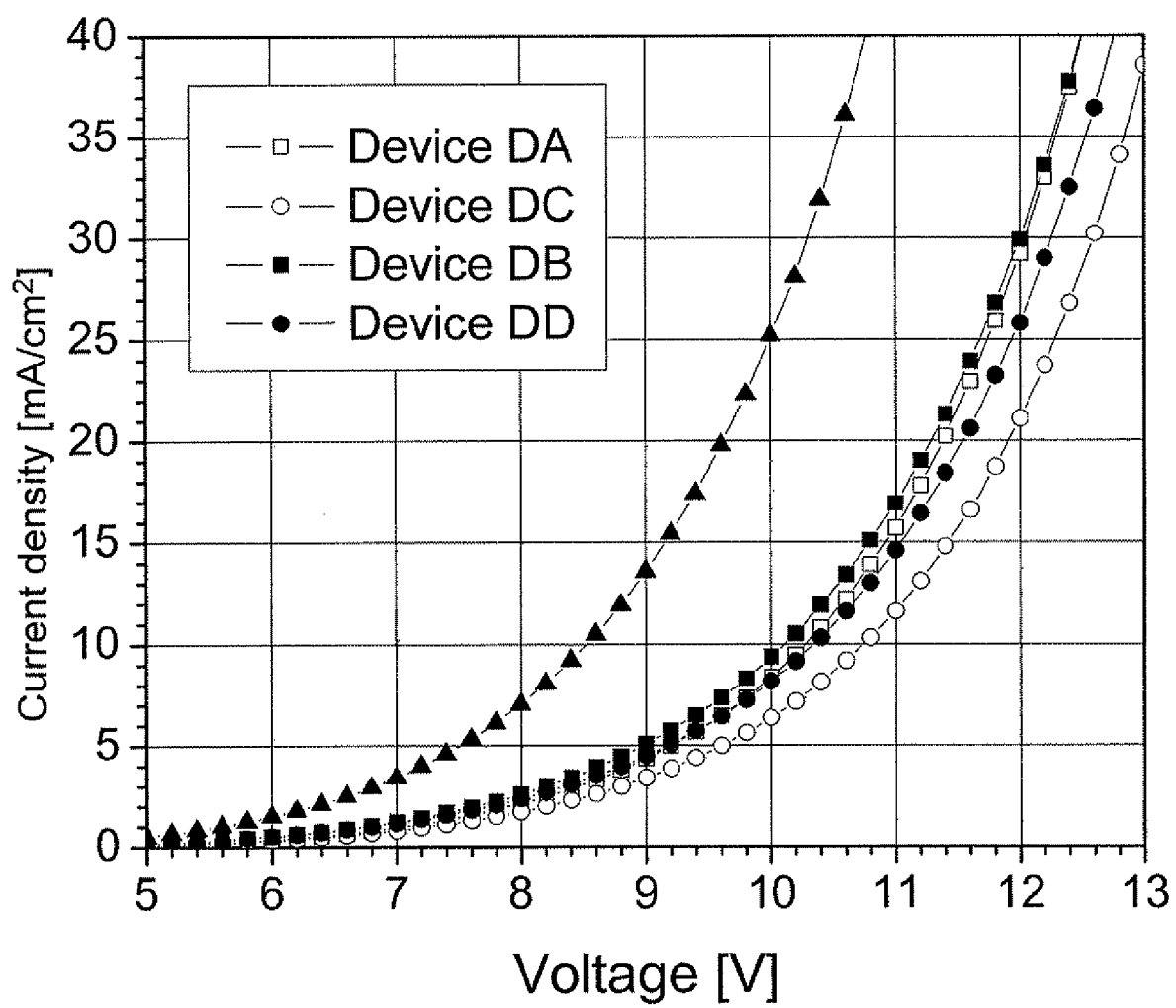
FIG. 5 shows the plot of current density vs. voltage for devices DA, DB, DC and DD.
Figure 6:
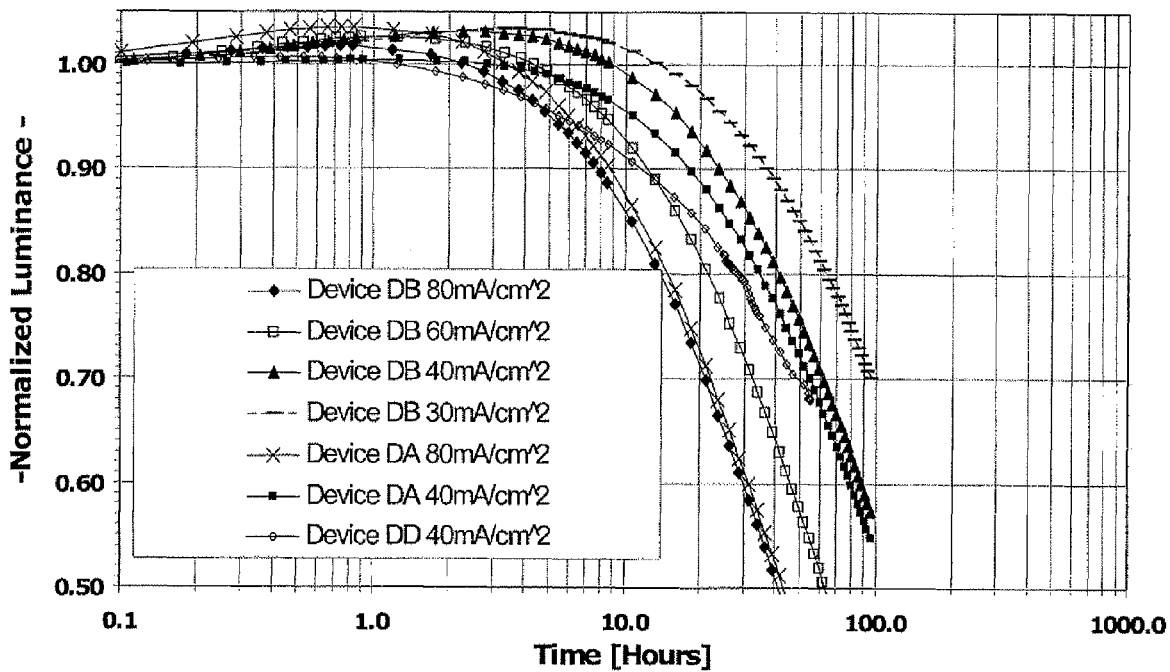
FIG. 6 shows the plot of normalized luminance vs. time for devices DA, DB, and DD.
Figure 7:
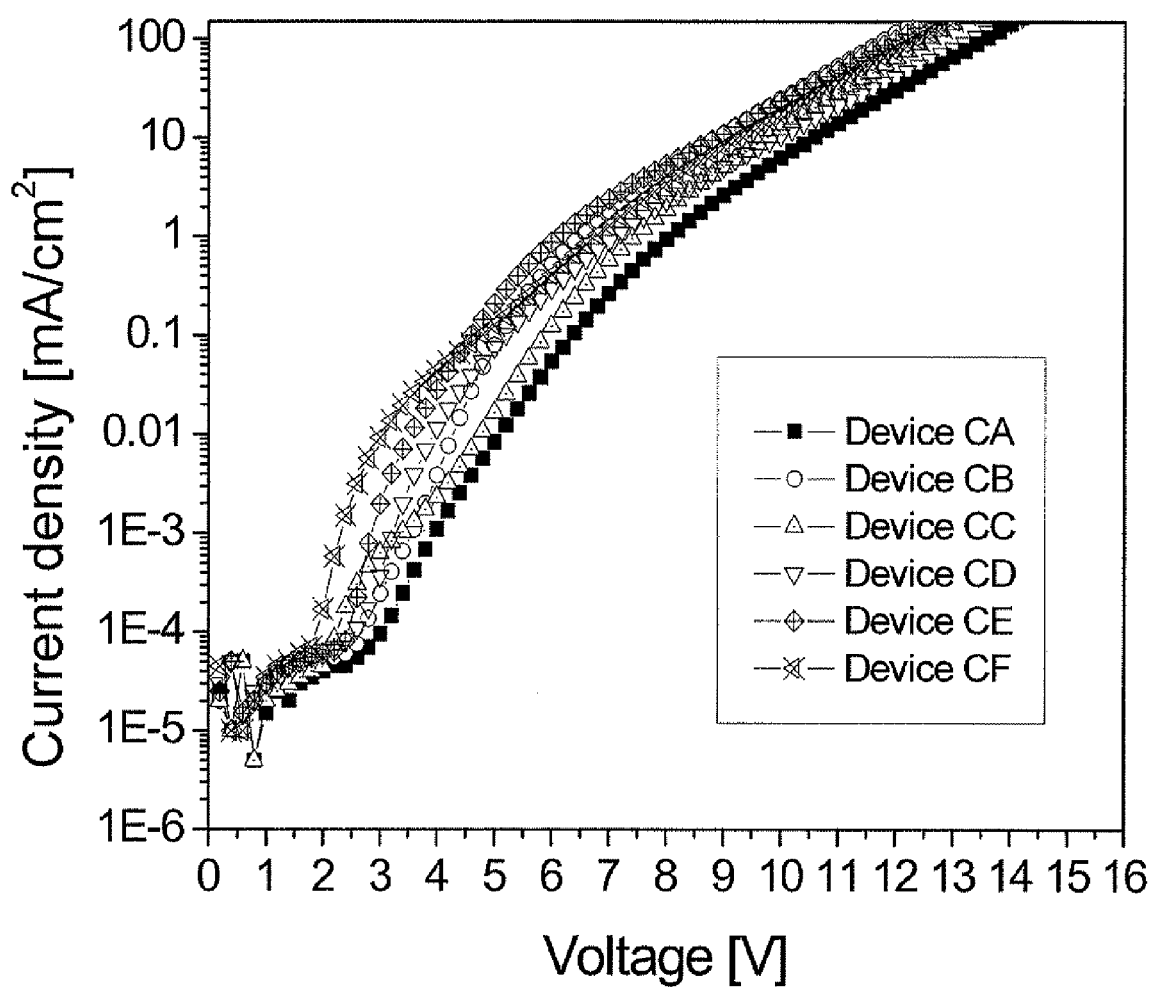
FIG. 7 shows the plot of current density vs. voltage for devices CA, CB, CC, CD, CE and CF.
Figure 8:
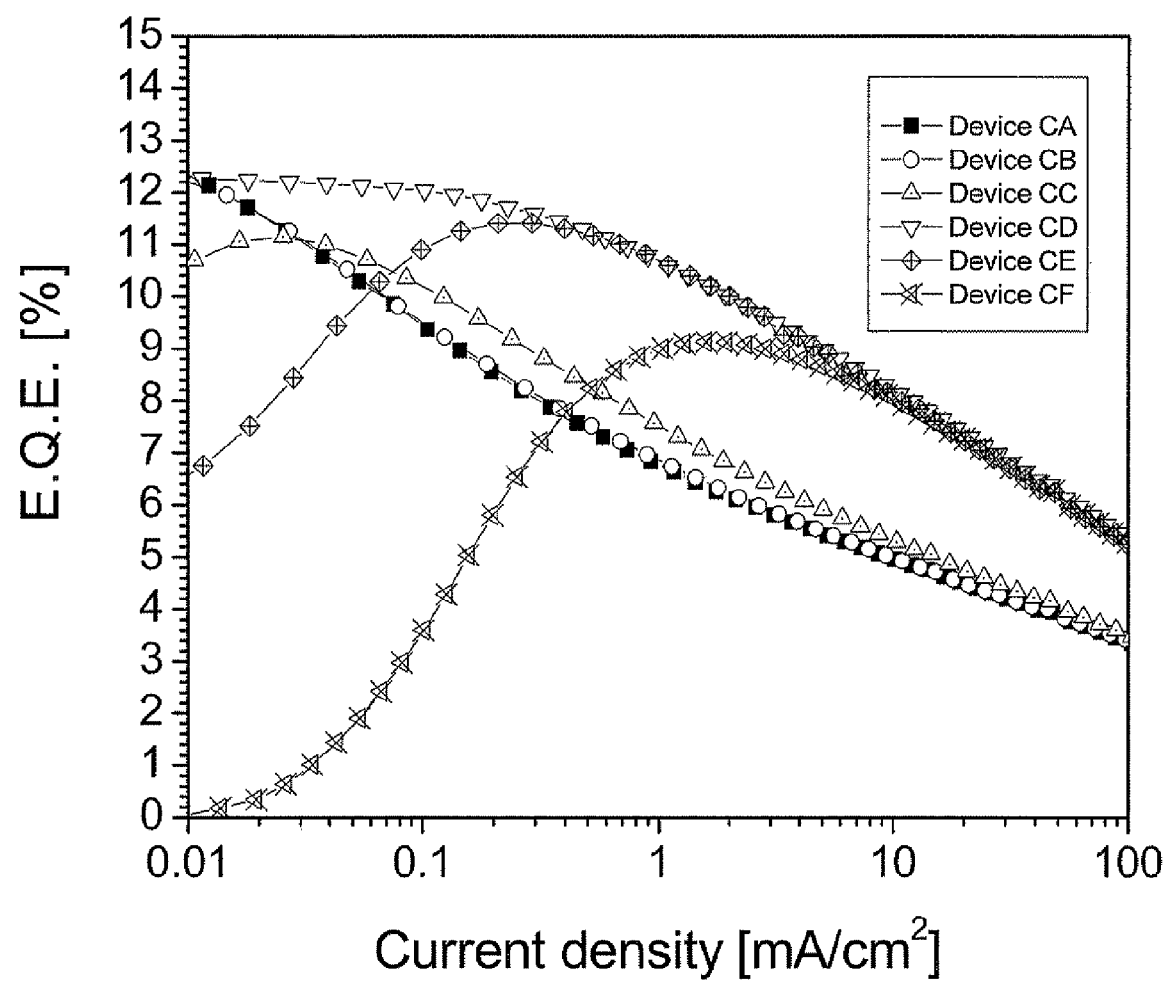
FIG. 8 shows the plots of external quantum efficiency vs. current density for devices CA, CB, CC, CD, CE and CF.
Figure 9:
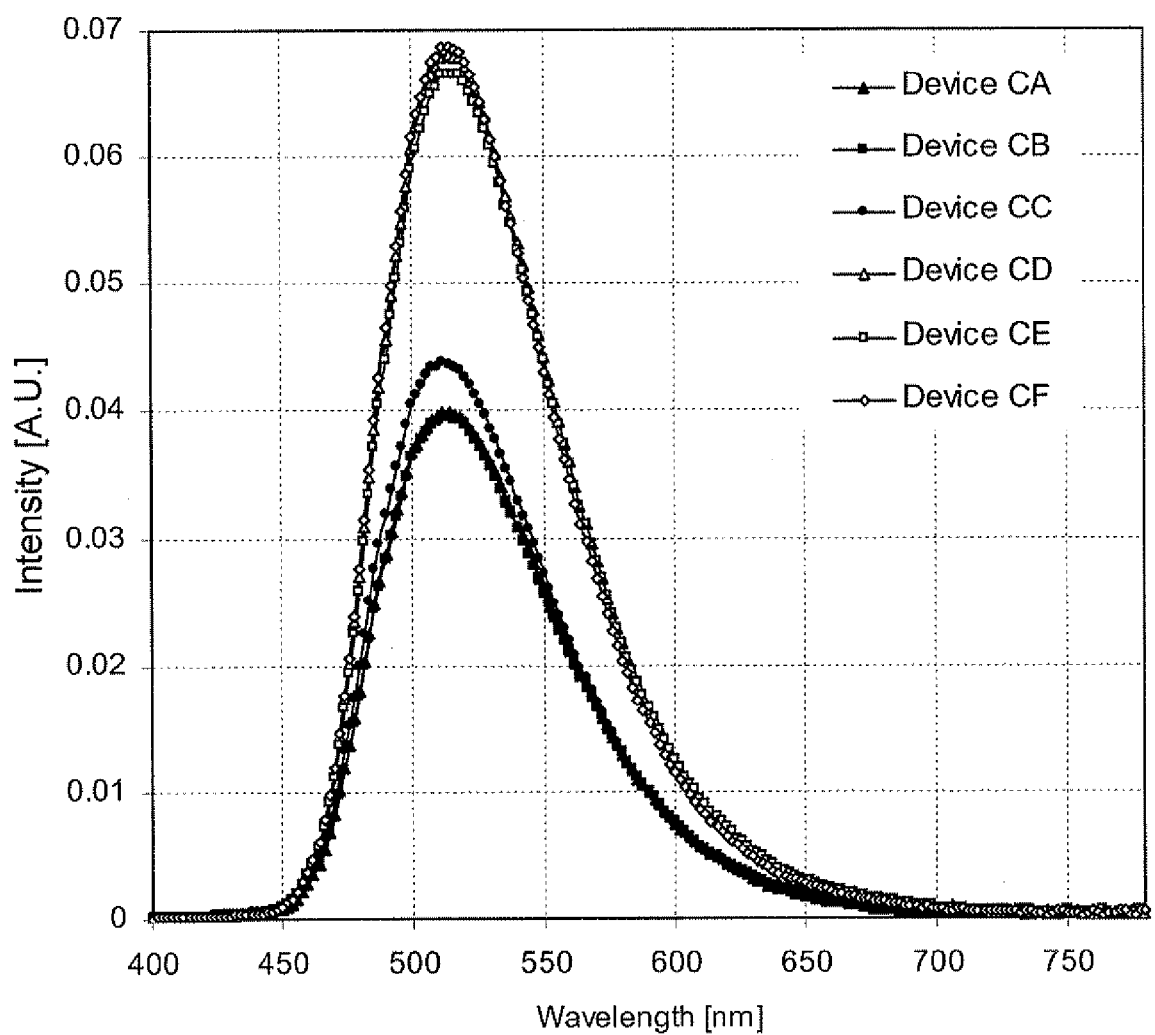
FIG. 9 shows electroluminescent spectra for devices CA, CB, CC, CD, CE and CF.
Figure 10:
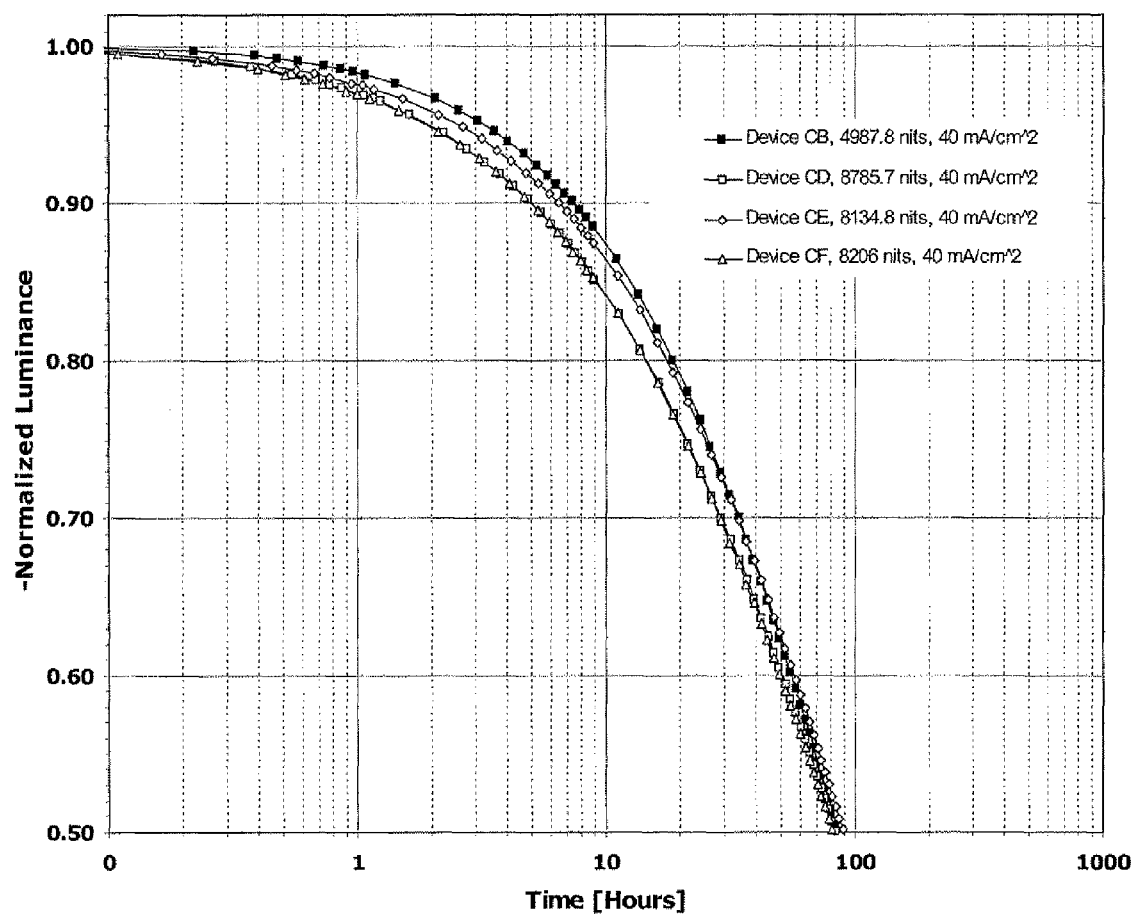
FIG. 10 shows normalized luminance vs. time for devices CB, CD, CE and CF.
Figure 11:
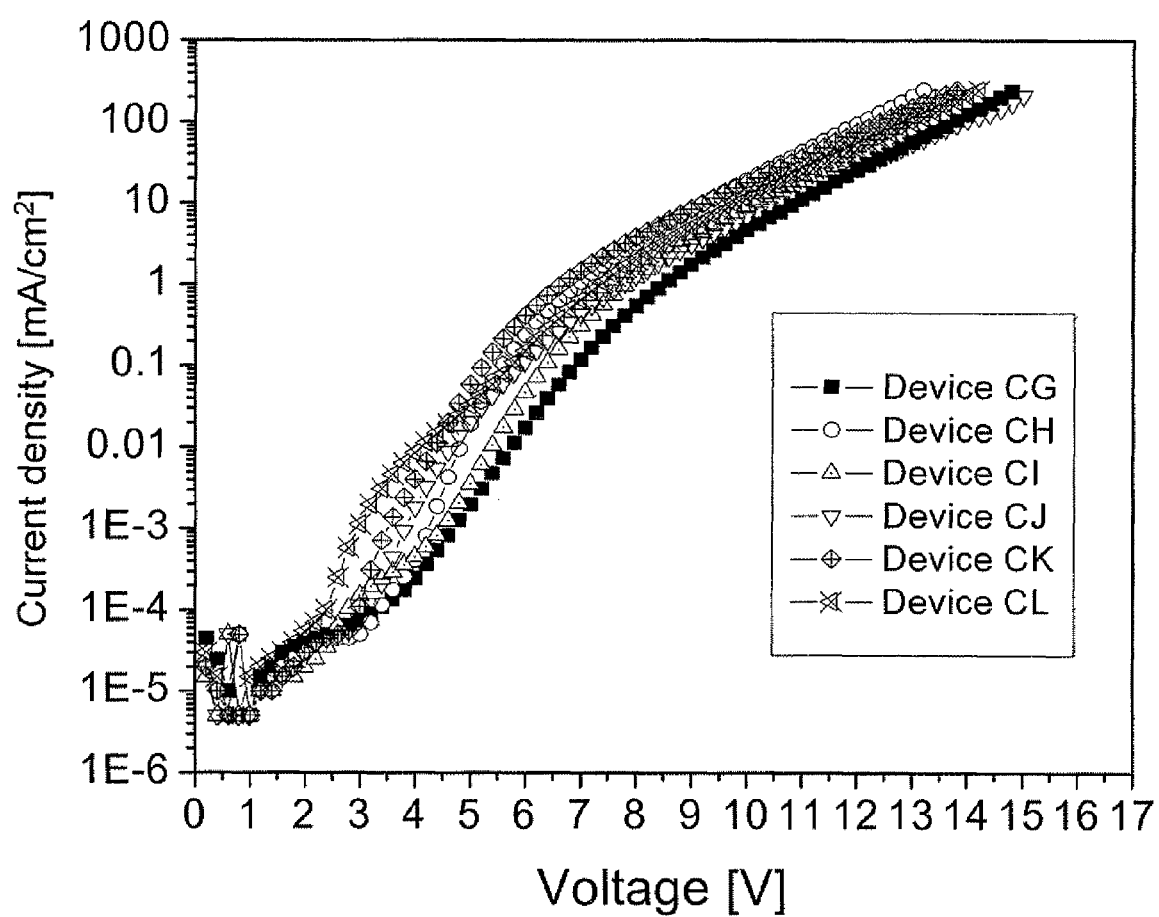
FIG. 11 shows plots of current density vs. voltage for devices CG, CH, CI, CJ, CK, and CL.
Figure 12:
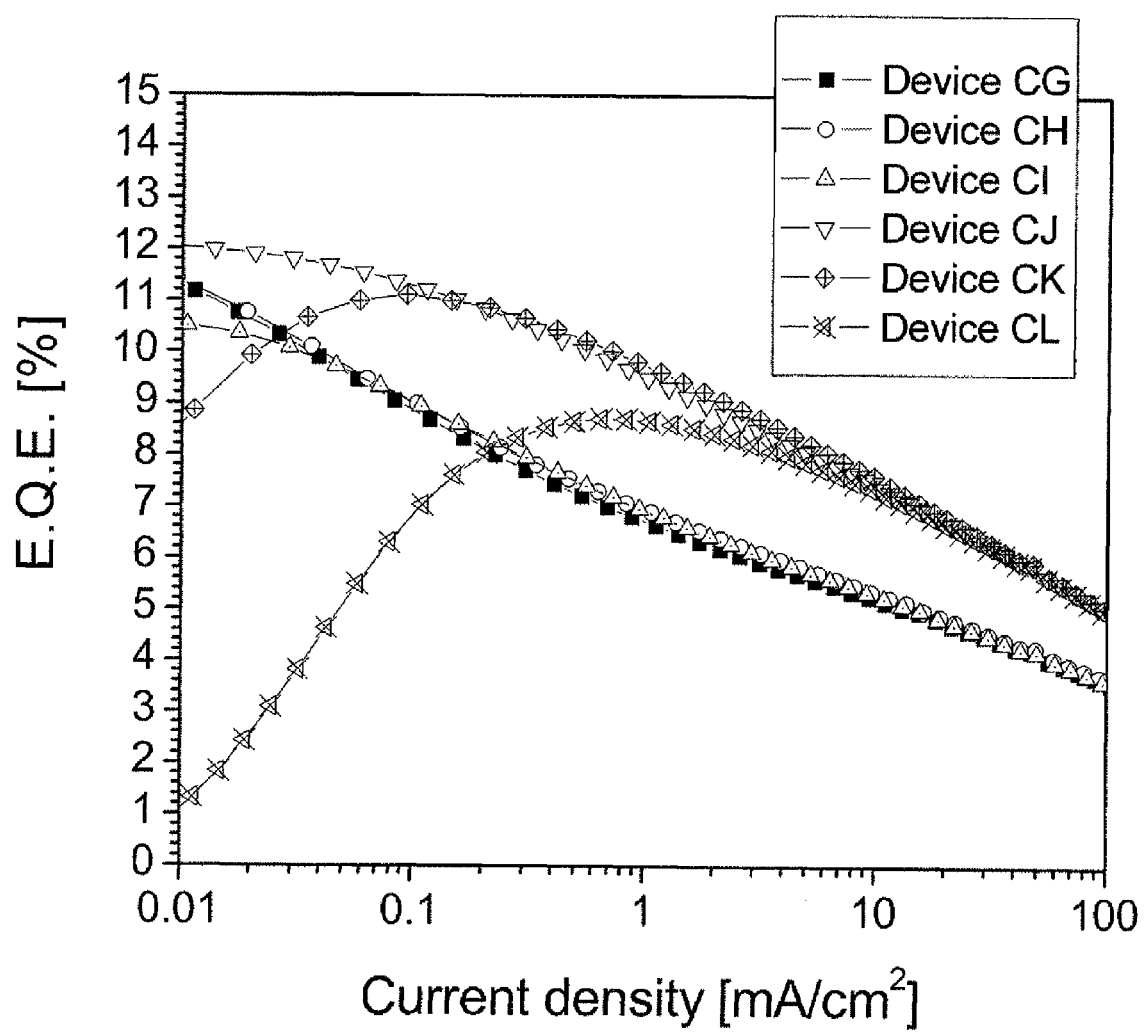
FIG. 12 shows the plots of external quantum efficiency vs. current density for devices CG, CH, CI, CJ, CK, and CL.
Figure 13:
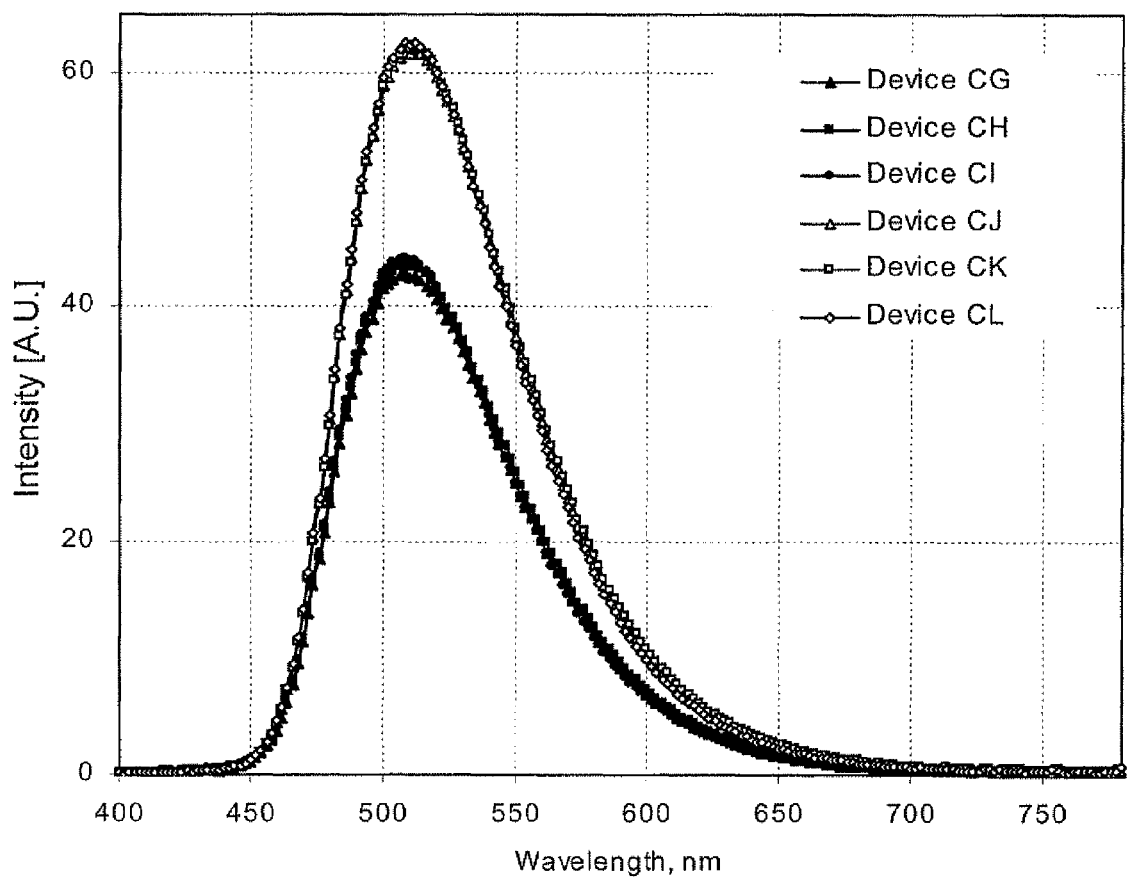
FIG. 13 shows electroluminescent spectra for devices CG, CH, CI, CJ, CK, and CL.
Figure 14:
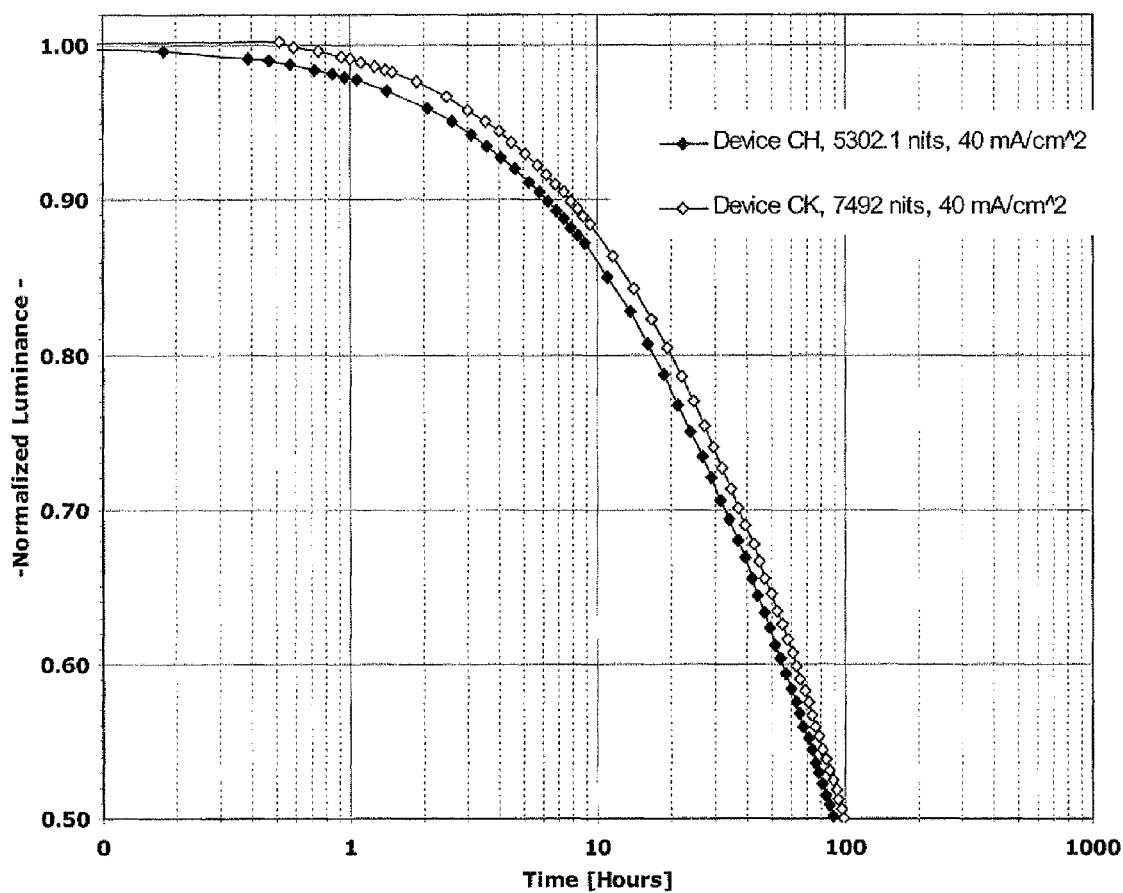
FIG. 14 shows plots of normalized luminance vs. time for devices CH and CK.
Figure 15:
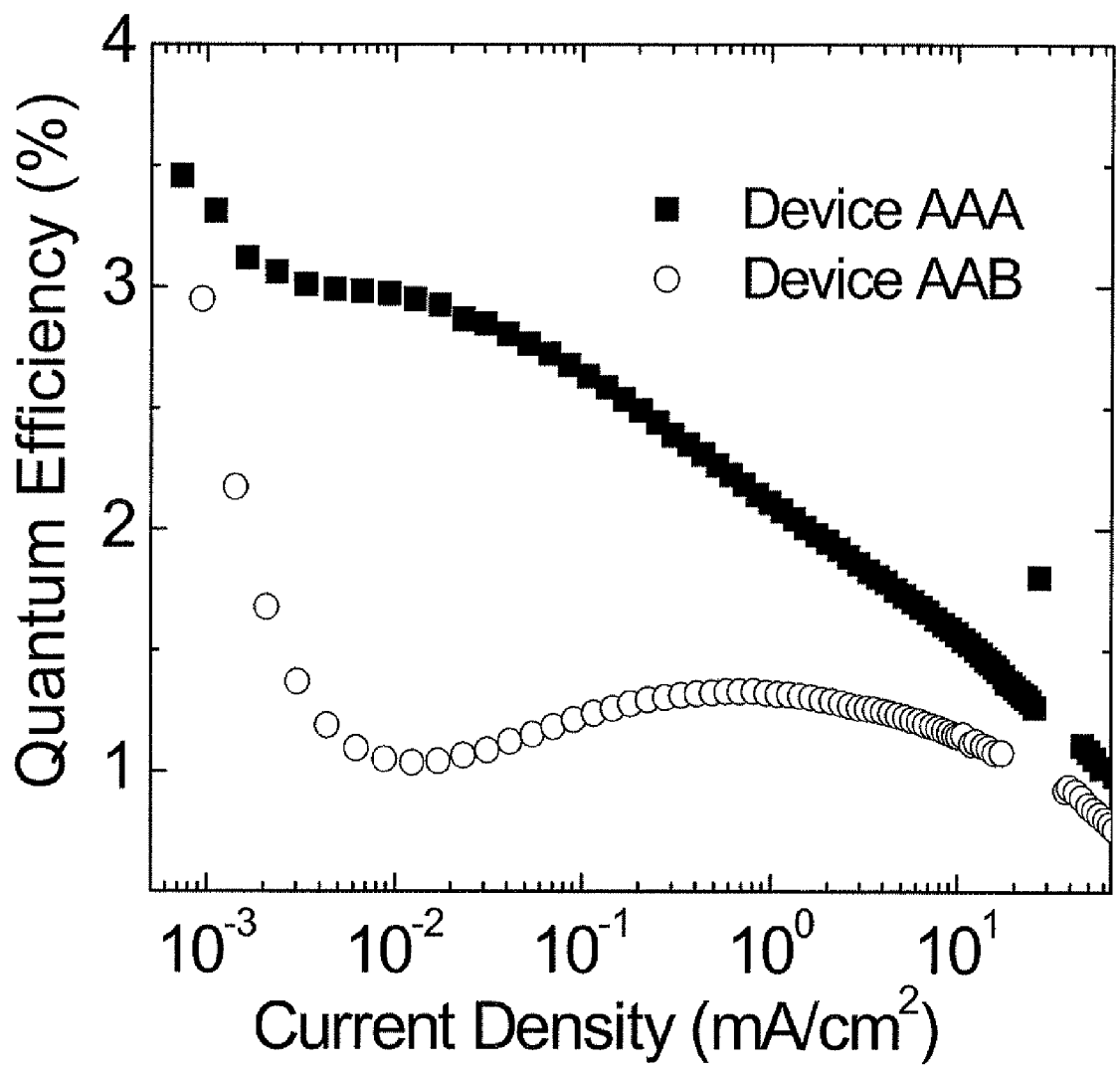
FIG. 15 shows plots of external quantum efficiency vs. current density for devices AAA and AAB.
Figure 16:
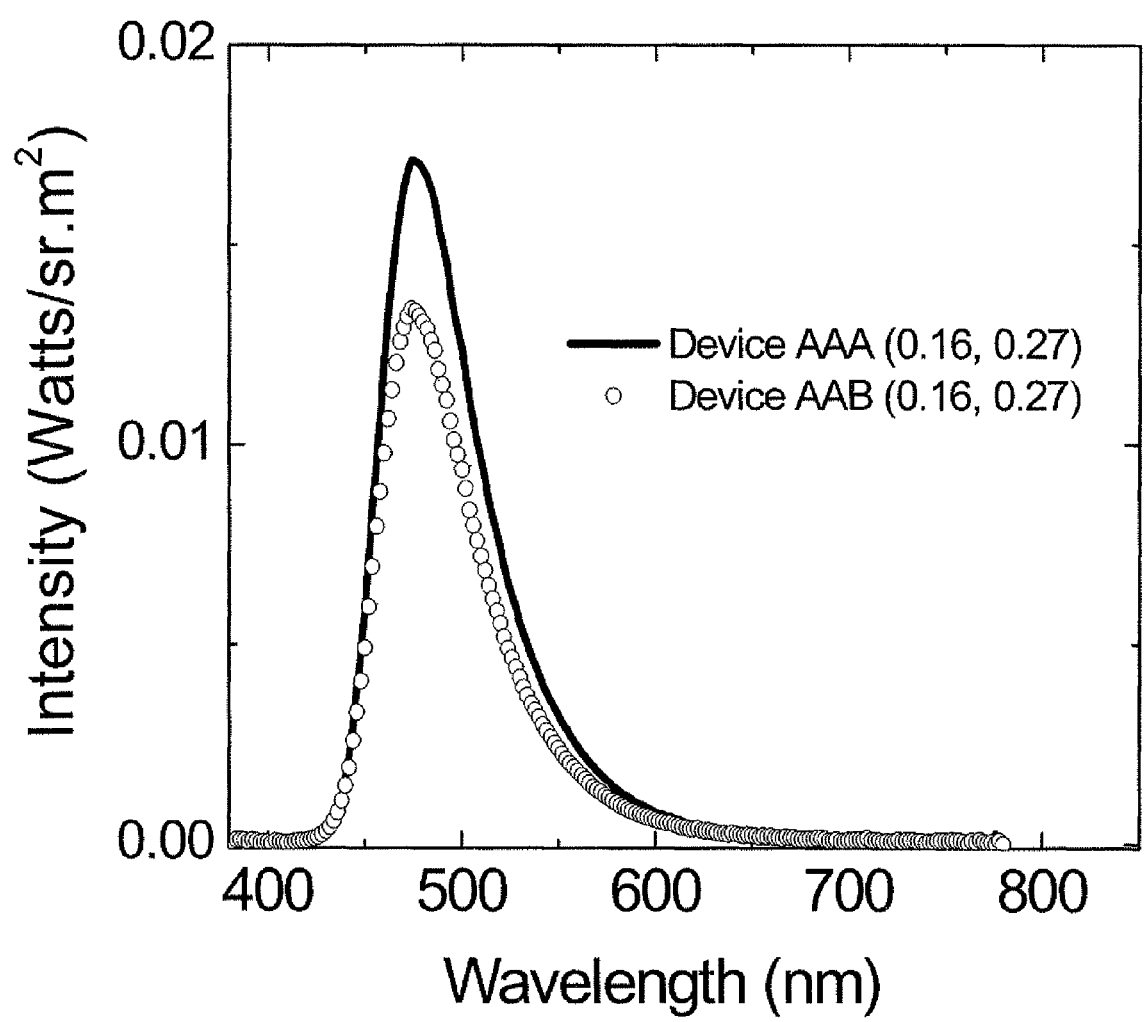
FIG. 16 shows electroluminescent spectra for devices AAA and AAB.
Figure 17:
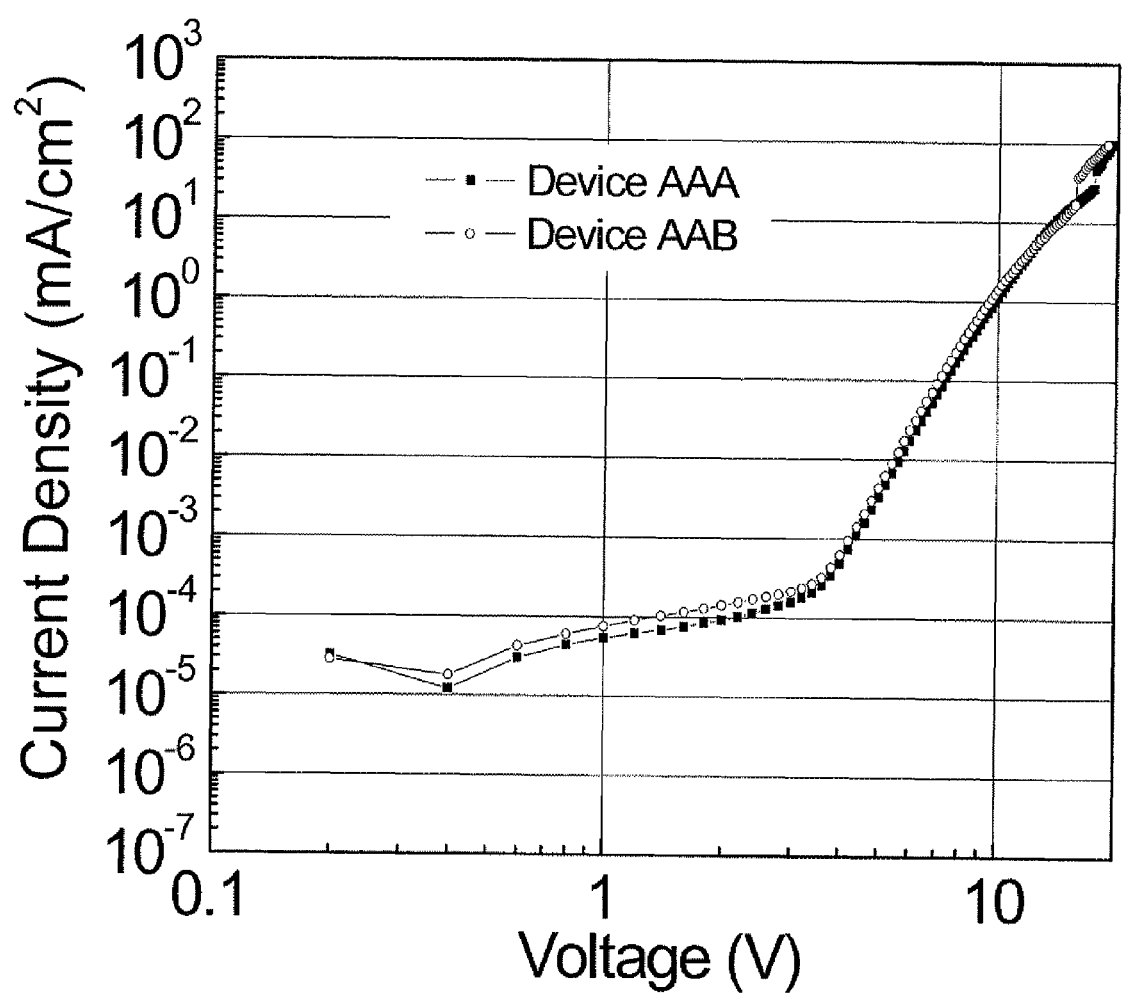
FIG. 17 shows plots of current density vs. voltage for devices AAA and AAB.
Figure 18:
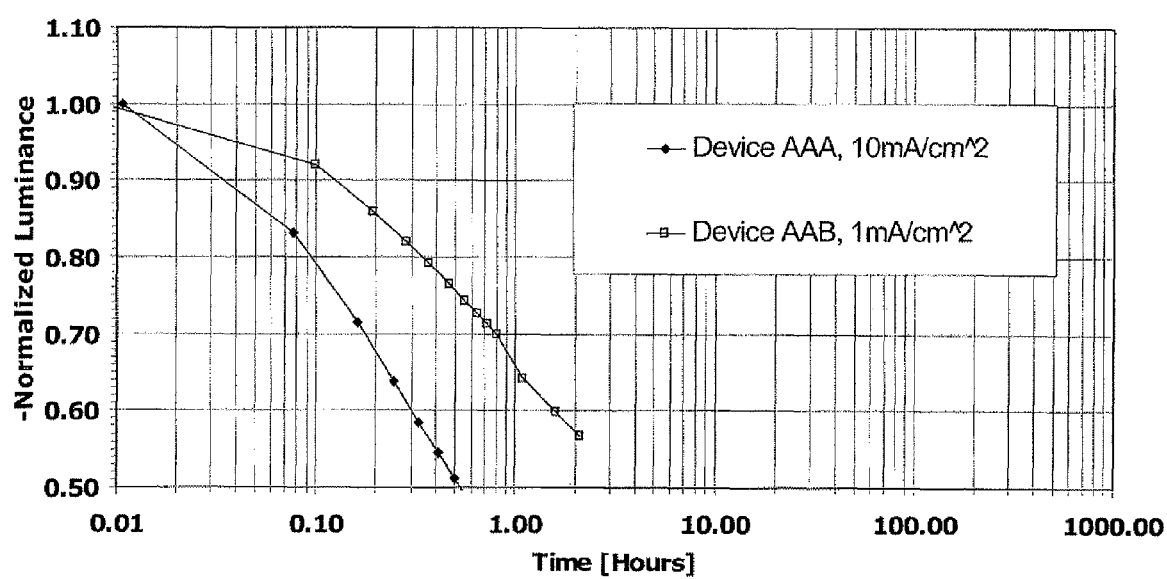
FIG. 18 shows plots of normalized luminance vs. time for devices AAA and AAB.
Figure 19:
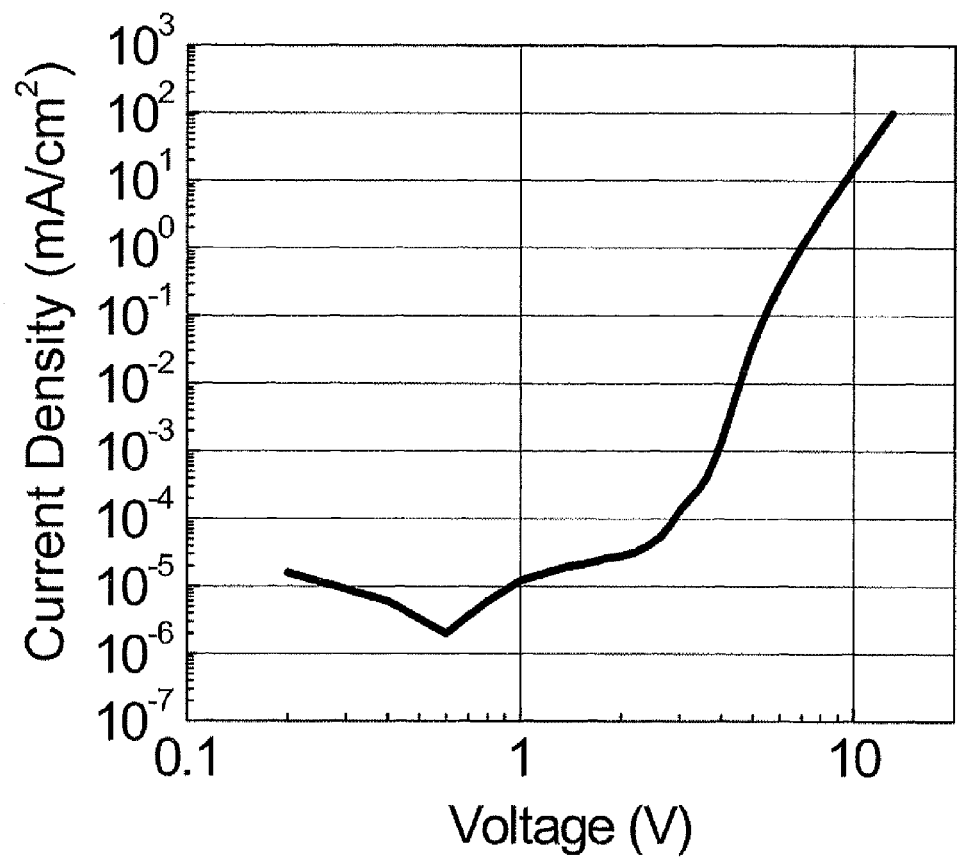
FIG. 19 shows the plot of current density vs. voltage for the device: HIL4 [10 nm]/NPD [30 nm]/CBP:es-5, 6% [30 nm]/ 2,3,6,7,10,11-hexaphenyltriphenylene [5 nm]/Alq [45 nm]/ LiF [0.5 nm]/Al [10 nm].
Figure 20:
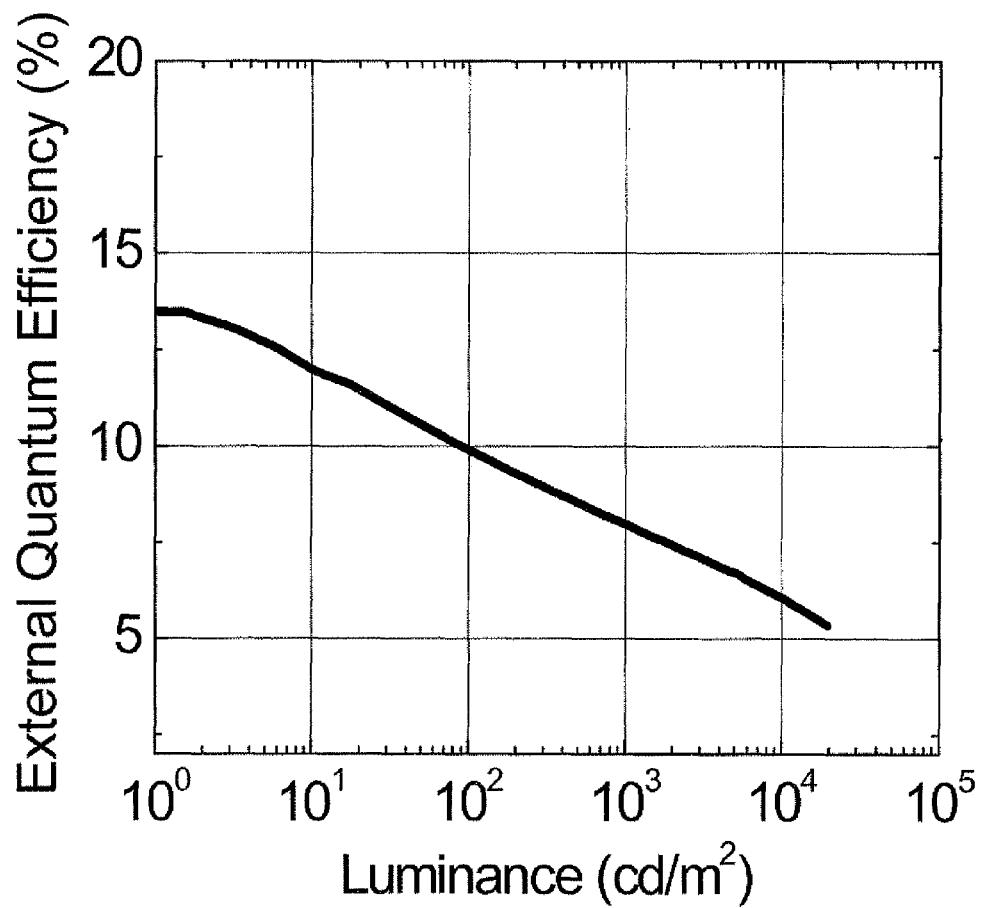
FIG. 20 shows the plot of external quantum efficiency vs. luminance for the device: HIL4 [10 nm]/NPD [30 nm]/CBP: es-5, 6% [30 nm]/2,3,6,7,10,11-hexaphenyltriphenylene [5 nm]/Alq [45 nm]/LiF [0.5 nm]/Al [100 nm].
Figure 21:
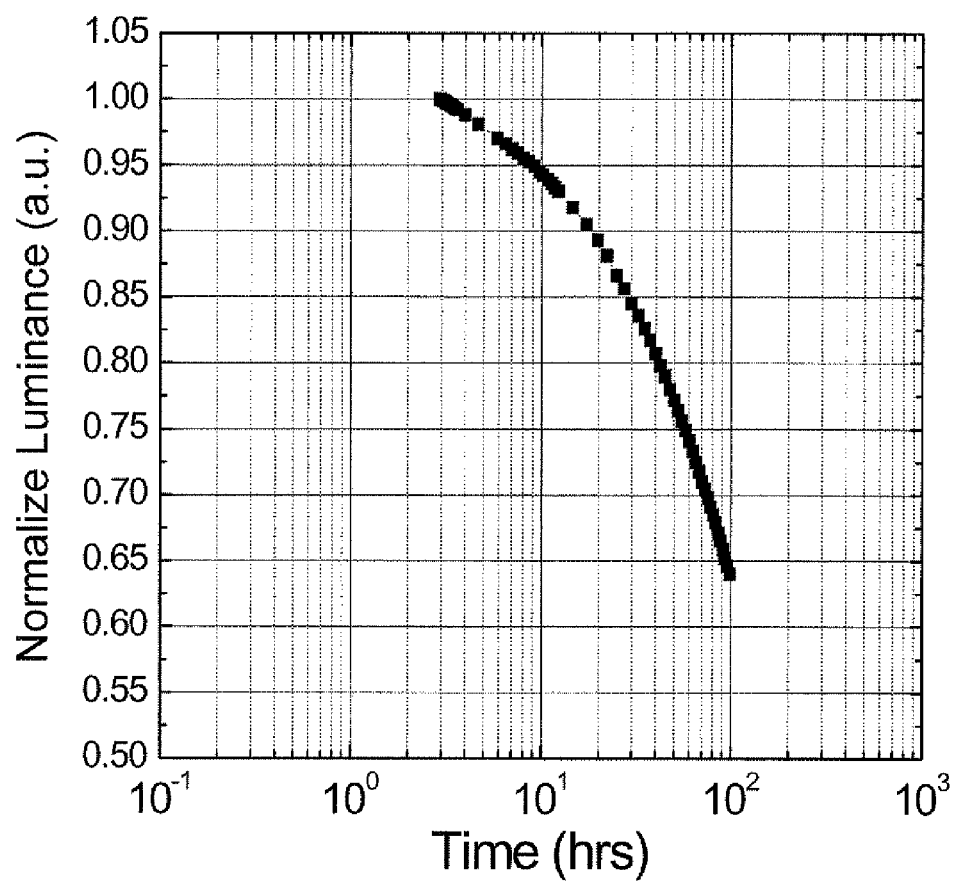
FIG. 21 shows the plot of normalized luminance vs. time for the device: HIL4 [10 nm]/NPD [30 nm]/CBP:es-5, 6% [30 nm]/2,3,6,7,10,11-hexaphenyltriphenylene [5 nm]/Alq [45 nm]/LiF [0.5 nm]/Al [100 nm].
Figure 22:
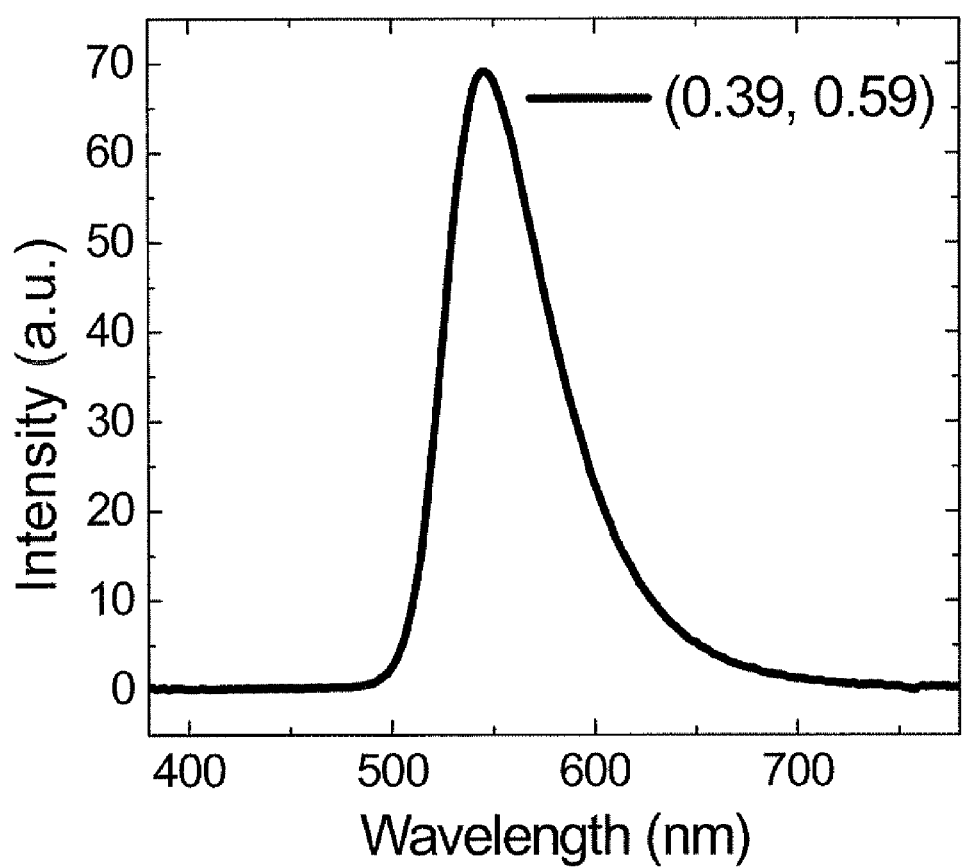
FIG. 22 shows the electroluminescent spectrum of the device: HIL4 [10 nm]/NPD [30 nm]/CBP:es-5, 6% [30 nm]/ 2,3,6,7,10,11-hexaphenyltriphenylene [5 nm]/Alq [45 nm]/ LiF [0.5 nm]/Al [100 nm].
Figure 23:
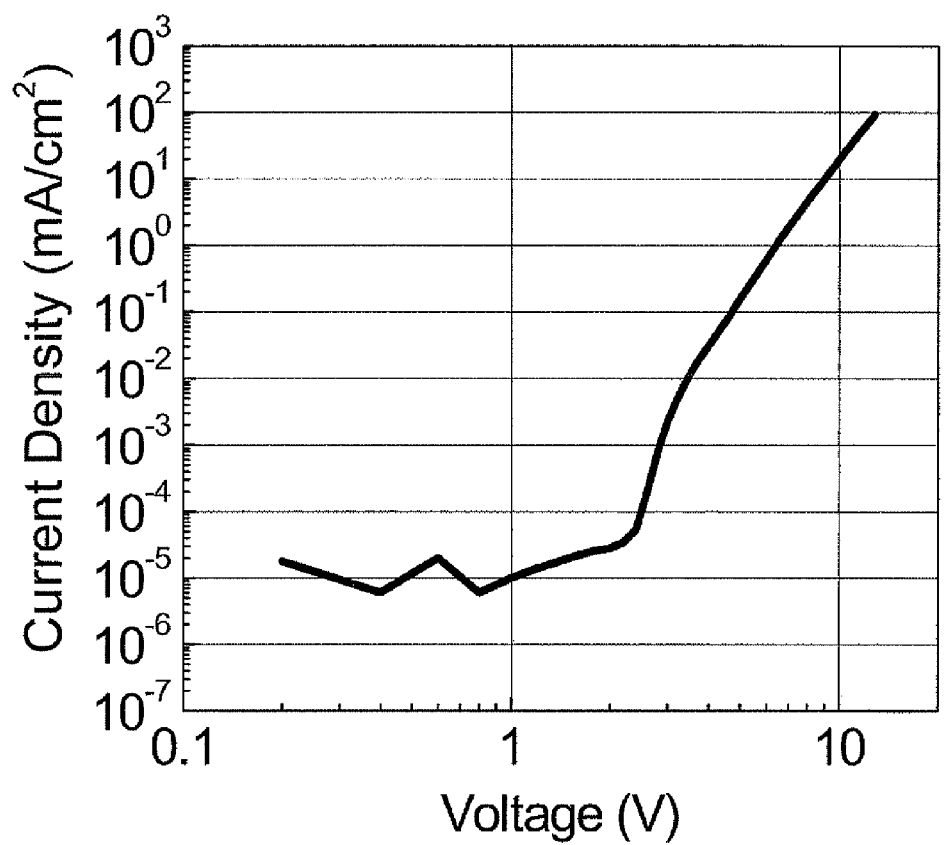
FIG. 23 shows the plot of current density vs. voltage for the device: HIL4 [10 nm]/NPD [30 nm]/CBP:es-5, 10% [30 nm]/ 2,3,6,7,10,11-hexaphenyltriphenylene [5 nm]/Alq [45 nm]/ LiF [0.5 nm]/Al [100 nm].
Figure 24:
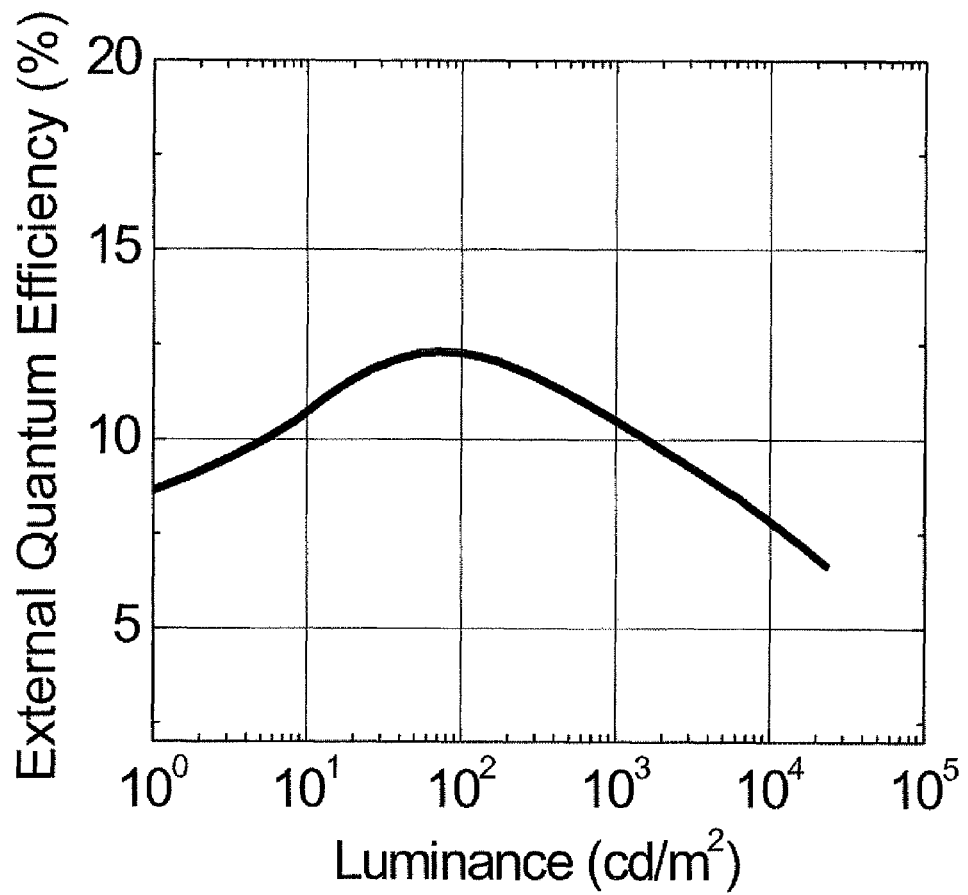
FIG. 24 shows the plot of external quantum efficiency vs. luminance for the device: HIL4 [10 nm]/NPD [30 nm]/CBP: es-5, 10% [30 nm]/2,3,6,7,10,11-hexaphenyltriphenylene [5 nm]/Alq [45 nm]/LiF [0.5 nm]/Al [100 nm].
Figure 25:
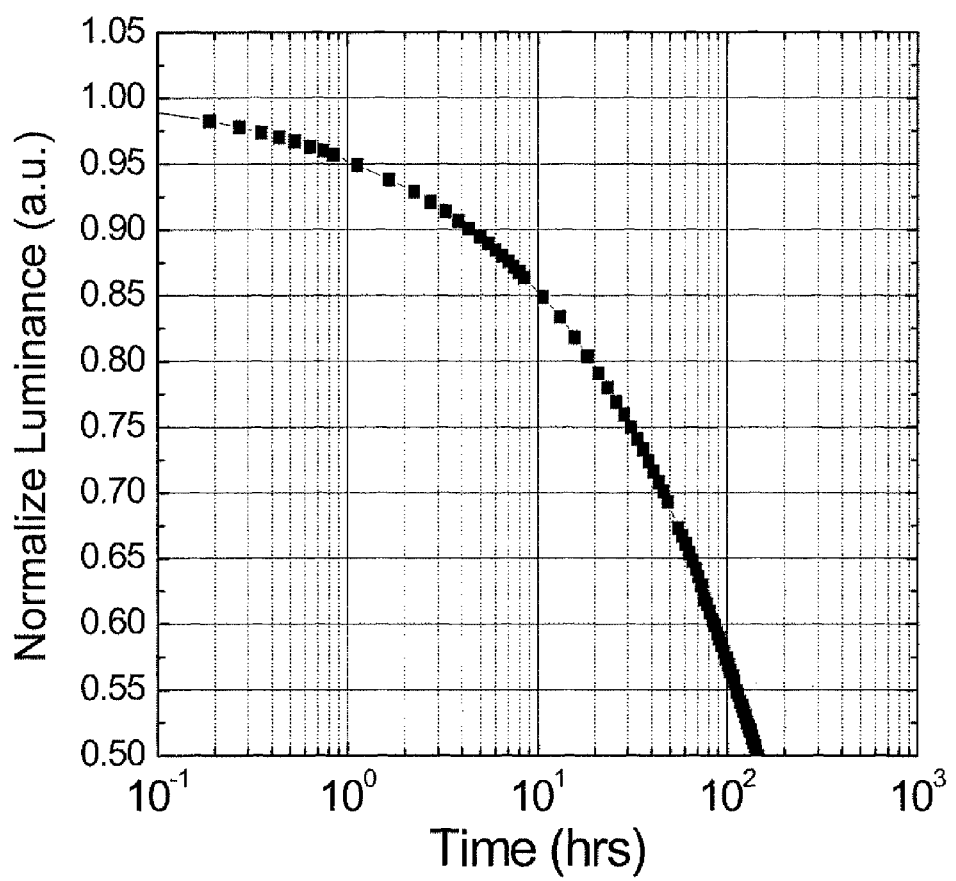
FIG. 25 shows the plot of normalized luminance vs. time for the device: HIL4 [10 nm]/NPD [30 nm]/CBP:es-5, 10% [30 nm]/2,3,6,7,10,11-hexaphenyltriphenylene [5 nm]/Alq [45 nm]/LiF [0.5 nm]/Al [100 nm].
Figure 26:
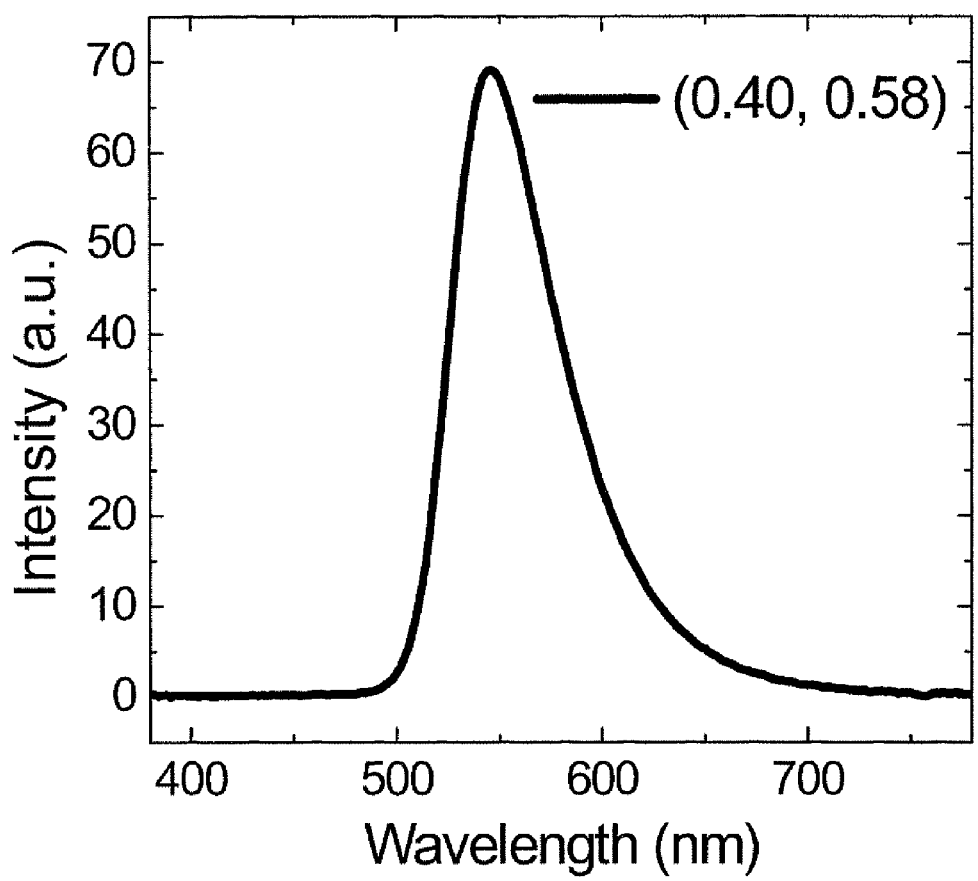
FIG. 26 shows the electroluminescent spectrum of the device: HIL4 [10 nm]/NPD [30 nm]/CBP:es-5, 10% [30 nm]/ 2,3,6,7,10,11-hexaphenyltriphenylene [5 nm]/Alq [45 nm]/ LiF [0.5 nm]/Al [10 nm].
Figure 27:
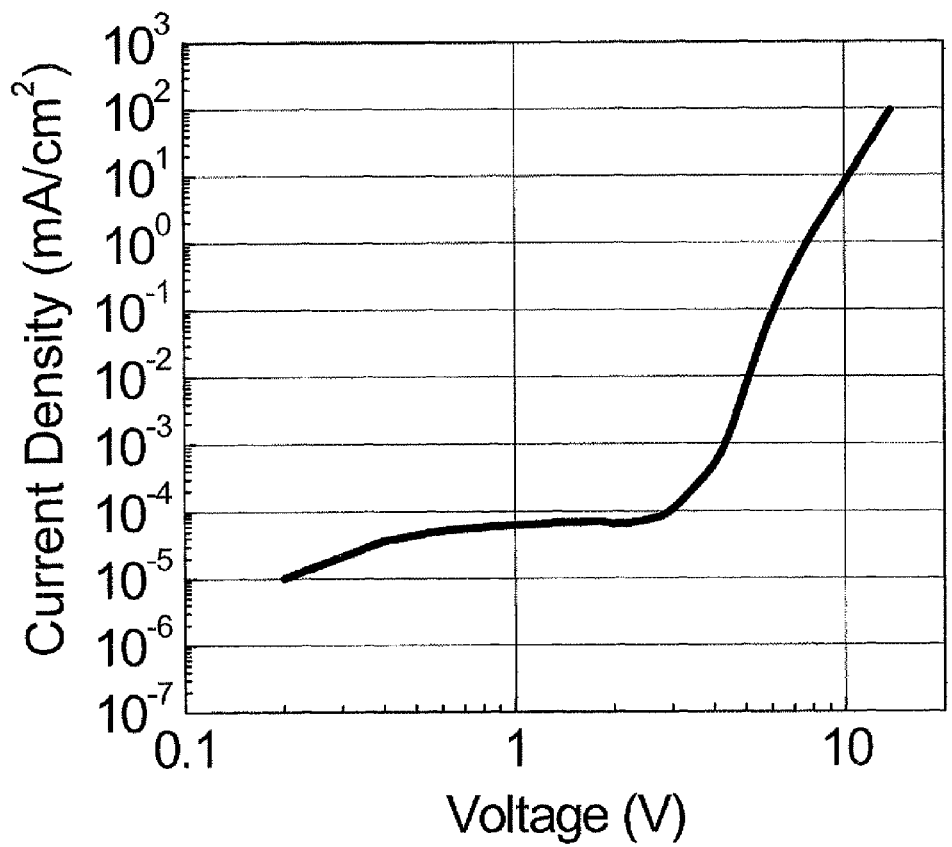
FIG. 27 shows the plot of current density vs. voltage for the device: CuPc [10 nm]/NPD [30 nm]/CBP:es-5, 6% [30 nm]/ 2,3,6,7,10,11-hexaphenyltriphenylene [5 nm]/Alq [45 nm]/ LiF [0.5 nm]/Al [100 nm].
Figure 28:
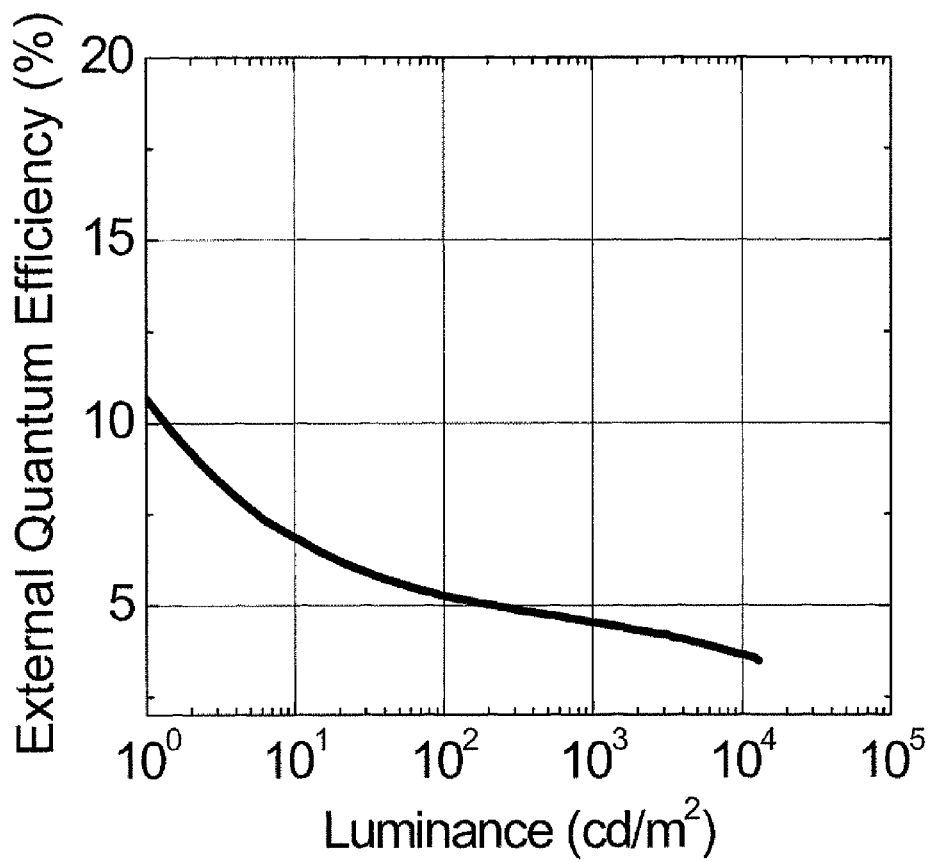
FIG. 28 shows the plot of external quantum efficiency vs. luminance for the device: CuPc [10 nm]/NPD [30 nm]/CBP: es-5, 6% [30 nm]/2,3,6,7,10,11-hexaphenyltriphenylene [5 nm]/Alq [45 nm]/LiF [0.5 nm]/Al [100 nm].
Figure 29:
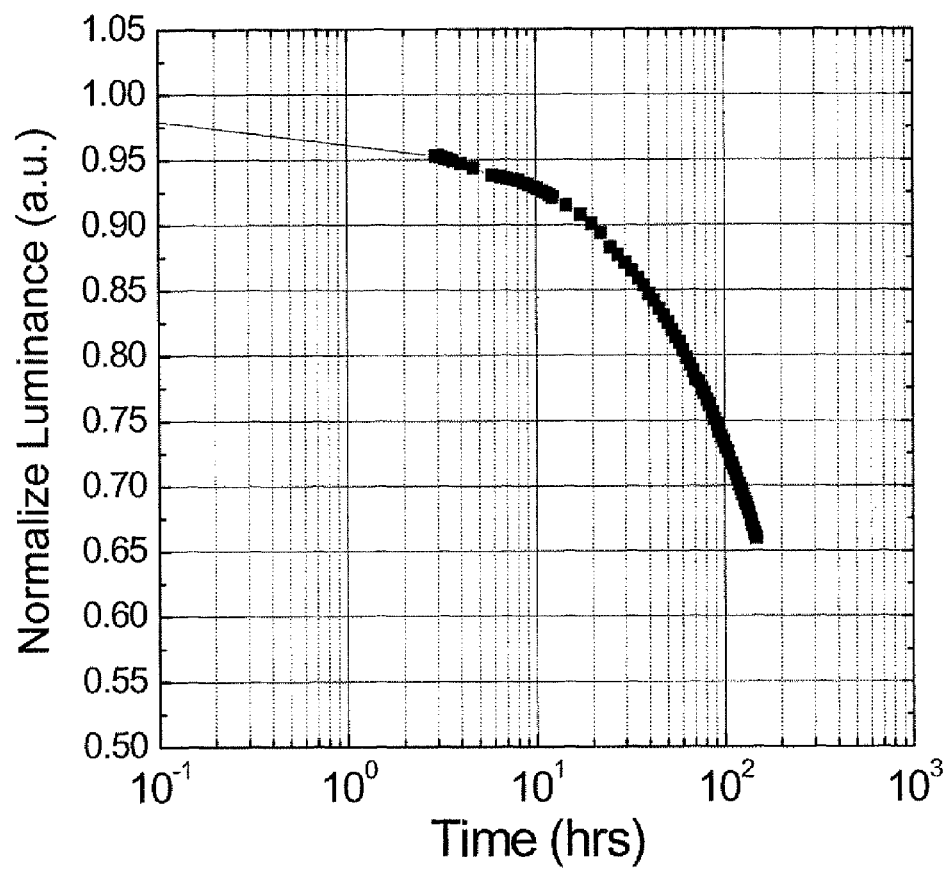
FIG. 29 shows the plot of normalized luminance vs. time for the device: CuPc [10 nm]/NPD [30 nm]/CBP:es-5, 6% [30 nm]/2,3,6,7,10,11-hexaphenyltriphenylene [5 nm]/Alq [45 nm]/LiF [0.5 nm]/Al [100 nm].
Figure 30:
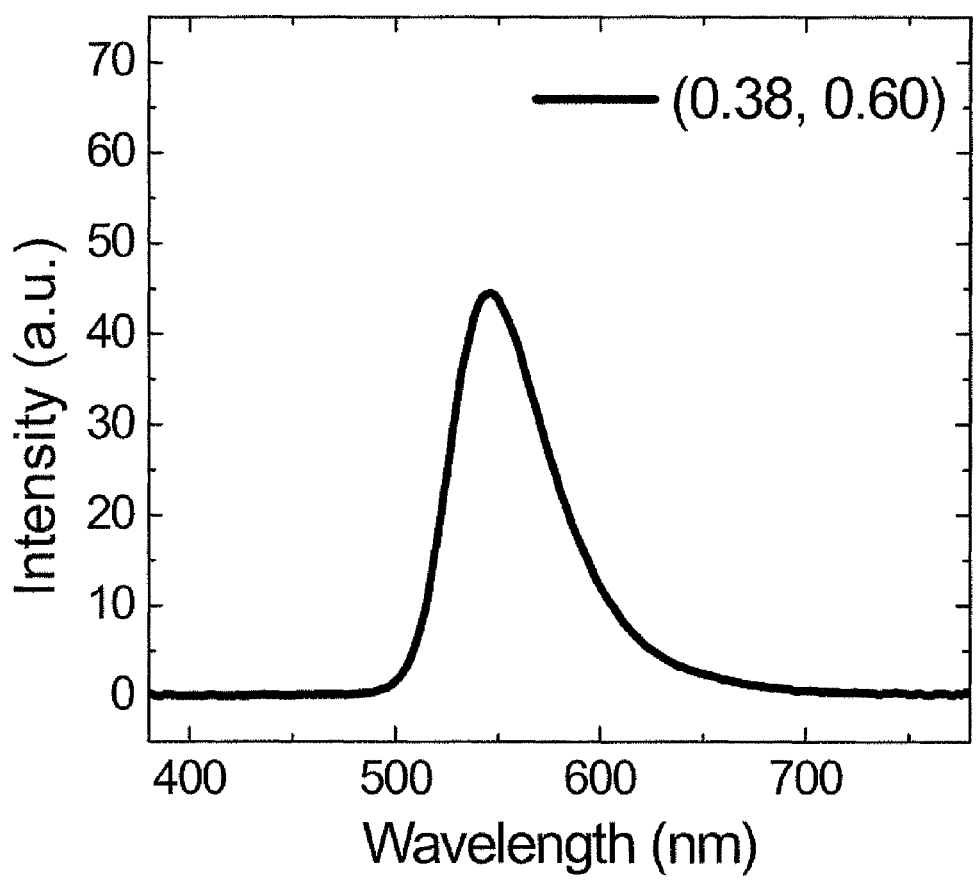
FIG. 30 shows the electroluminescent spectrum of the device: CuPc [10 nm]/NPD [30 nm]/CBP:es-5, 6% [30 nm]/ 2,3,6,7,10,11-hexaphenyltriphenylene [5 nm]/Alq [45 nm]/ LiF [0.5 nm]/Al [100 nm].
Figure 31:
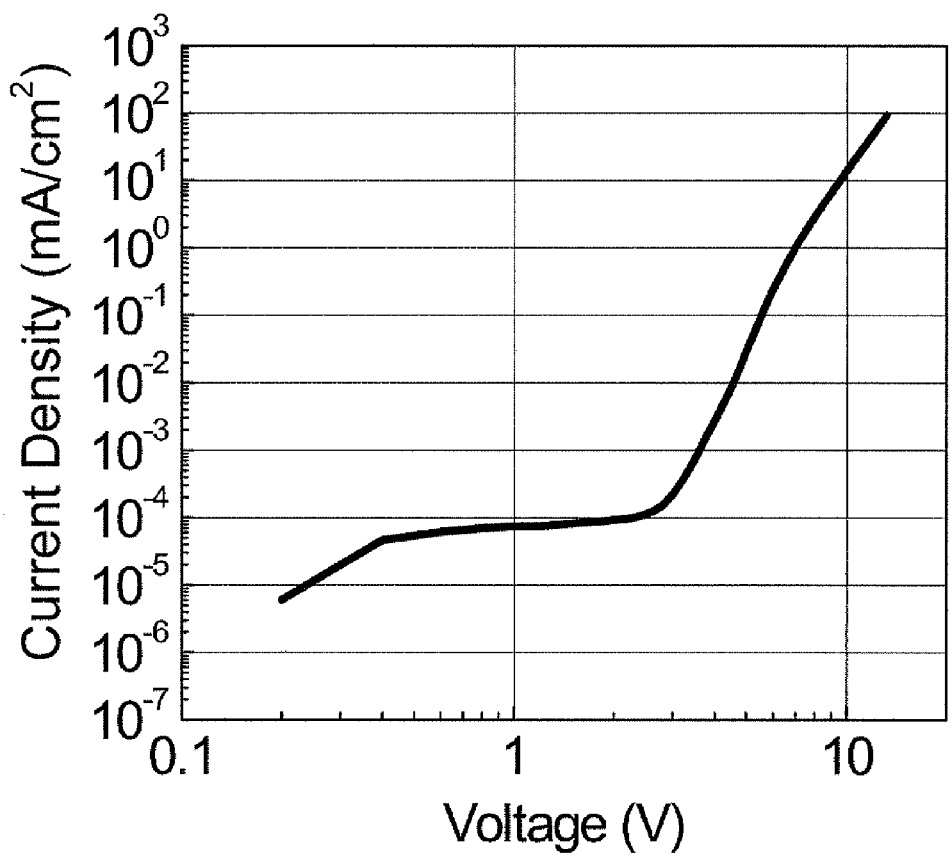
FIG. 31 shows the plot of current density vs. voltage for the device: CuPc [10 nm]/NPD [30 nm]/CBP:es-5, 10% [30 nm]/ 2,3,6,7,10,11-hexaphenyltriphenylene [5 nm]/Alq [45 nm]/ LiF [0.5 nm]/Al [100 nm].
Figure 32:
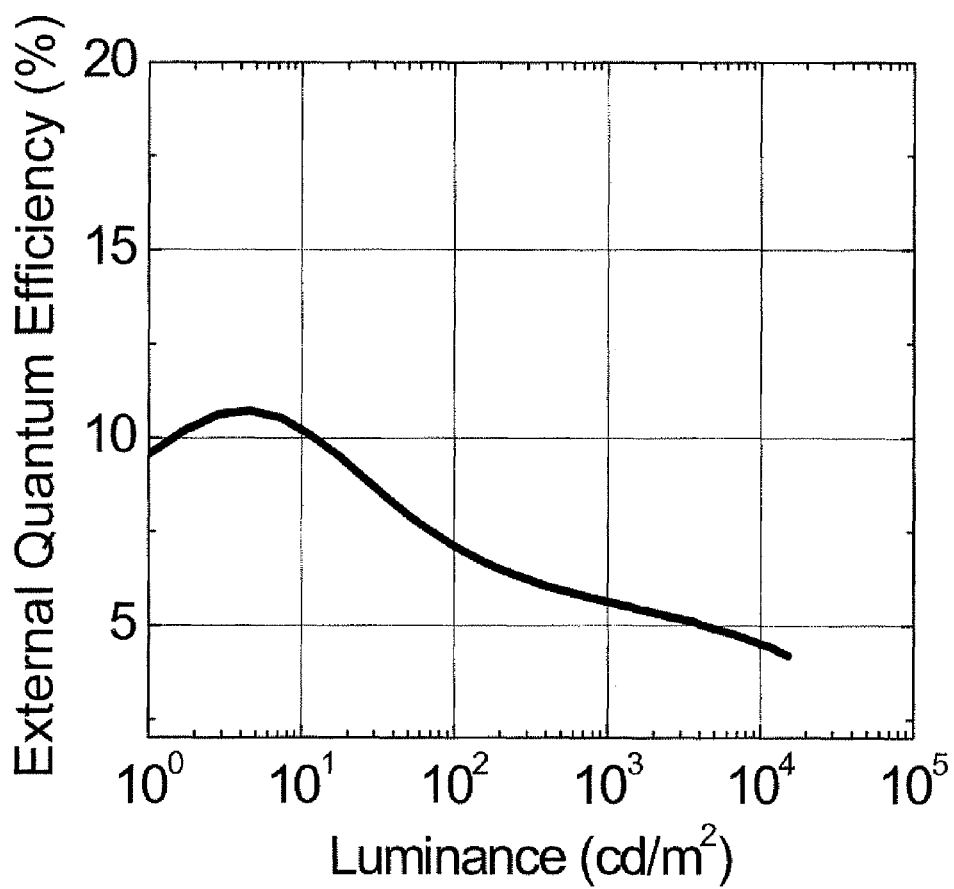
FIG. 32 shows the plot of external quantum efficiency vs. luminance for the device: CuPc [10 nm]/NPD [30 nm]/CBP: es-5, 10% [30 nm]/2,3,6,7,10,11-hexaphenyltriphenylene [10 nm]/Alq [45 nm]/LiF [0.5 nm]/Al [100 nm].
Figure 33:
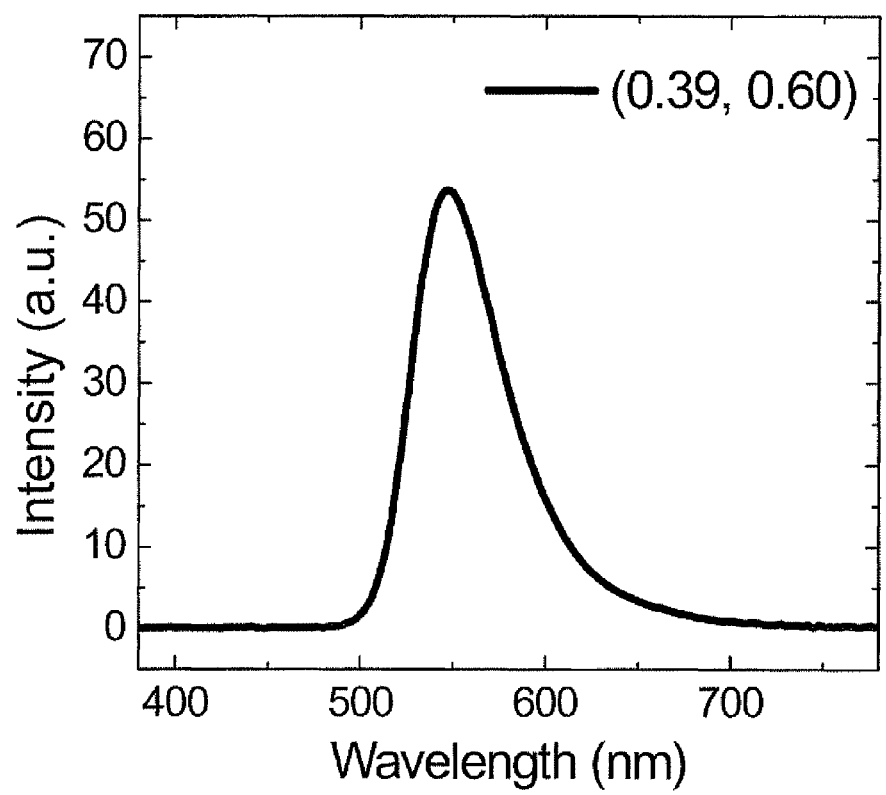
FIG. 33 shows the electroluminescent spectrum of the device: CuPc [10 nm]/NPD [30 nm]/CBP:es-5, 10% [30 nm]/ 2,3,6,7,10,11-hexaphenyltriphenylene [5 nm]/Alq [45 nm]/ LiF [0.5 nm]/Al [100 nm].
Figure 34:
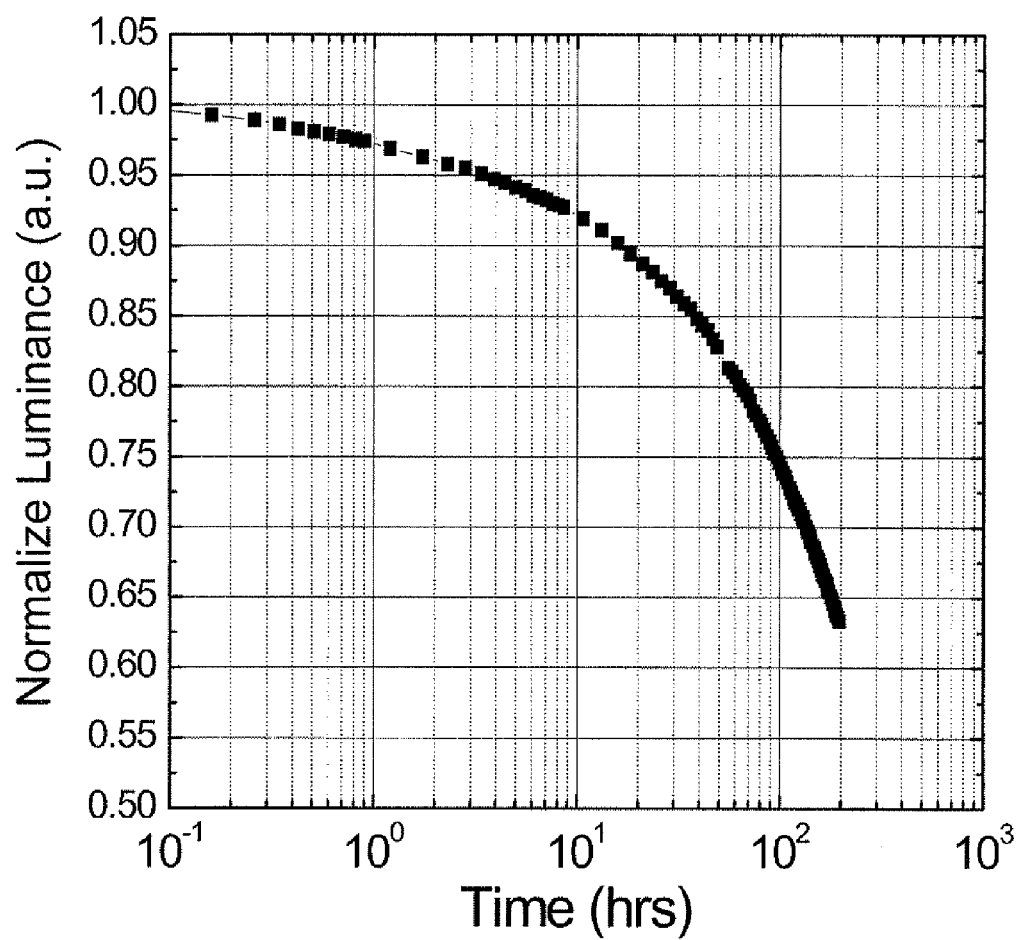
FIG. 34 shows the plot of normalized luminance vs. time for the device: CuPc [10 nm]/NPD [30 nm]/CBP:es-5, 10% [30 nm]/2,3,6,7,10,11-hexaphenyltriphenylene [5 nm]/Alq [45 nm]/LiF [0.5 nm]/Al [100 nm].
Figure 35:
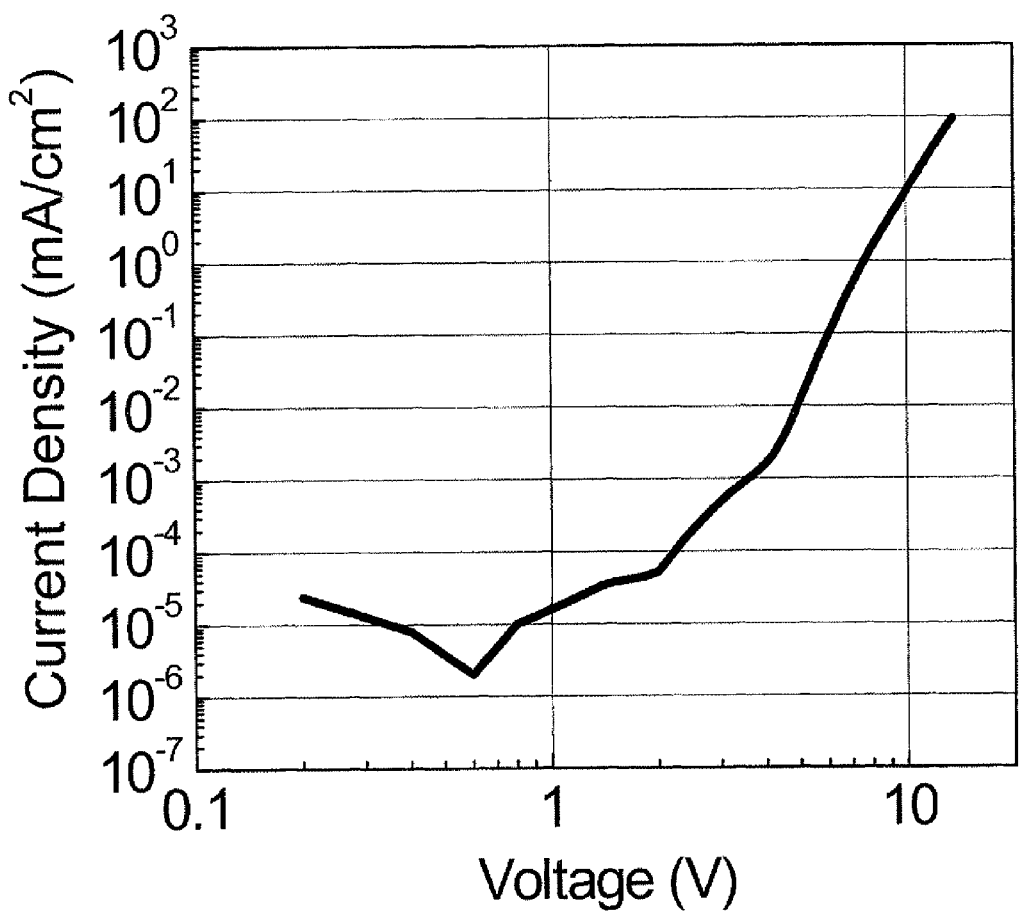
FIG. 35 shows the plot of current density vs. voltage for the device: HIL4 [10 nm]/NPD [30 nm]/CBP:es-5, 6% [30 nm]/ CBP [5 nm]/Alq [45 nm]/LiF [0.5 nm]/Al [100 nm].
Figure 36:
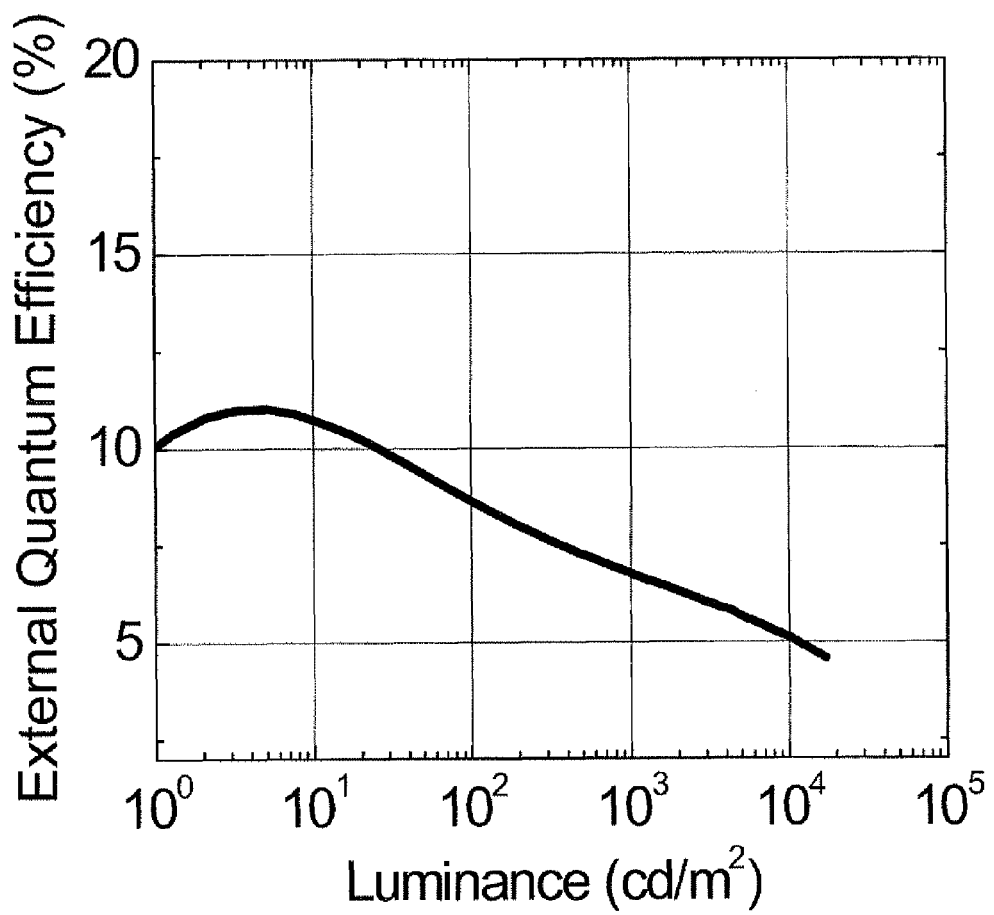
FIG. 36 shows the plot of external quantum efficiency vs. luminance for the device: HIL4 [10 nm]/NPD [30 nm]/CBP: es-5, 6% [30 nm]/CBP [5 nm]/Alq [45 nm]/LiF [0.5 nm]/Al [100 nm].
Figure 37:
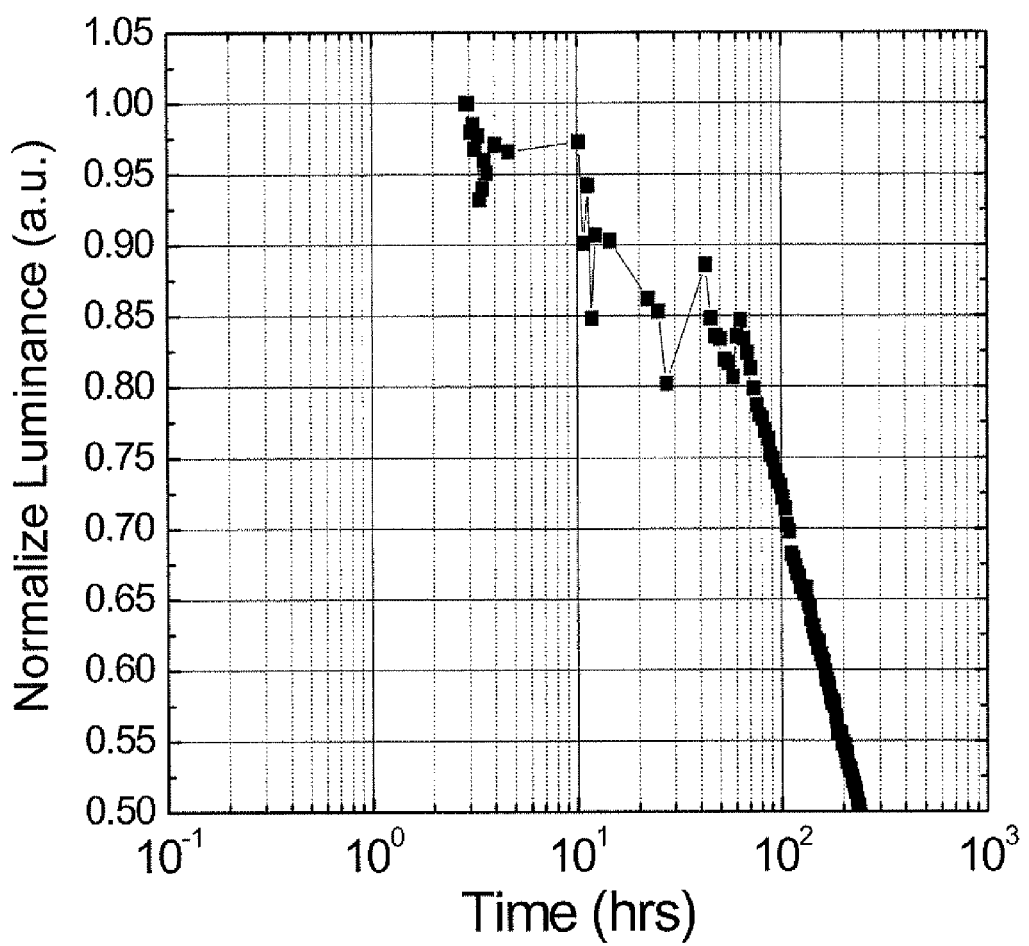
FIG. 37 shows the plot of normalized luminance vs. time for the device: HIL4 [10 nm]/NPD [30 nm]/CBP:es-5, 6% [30 nm]/CBP [5 nm]/Alq [45 nm]/LiF [0.5 nm]/Al [100 nm].
Figure 38:
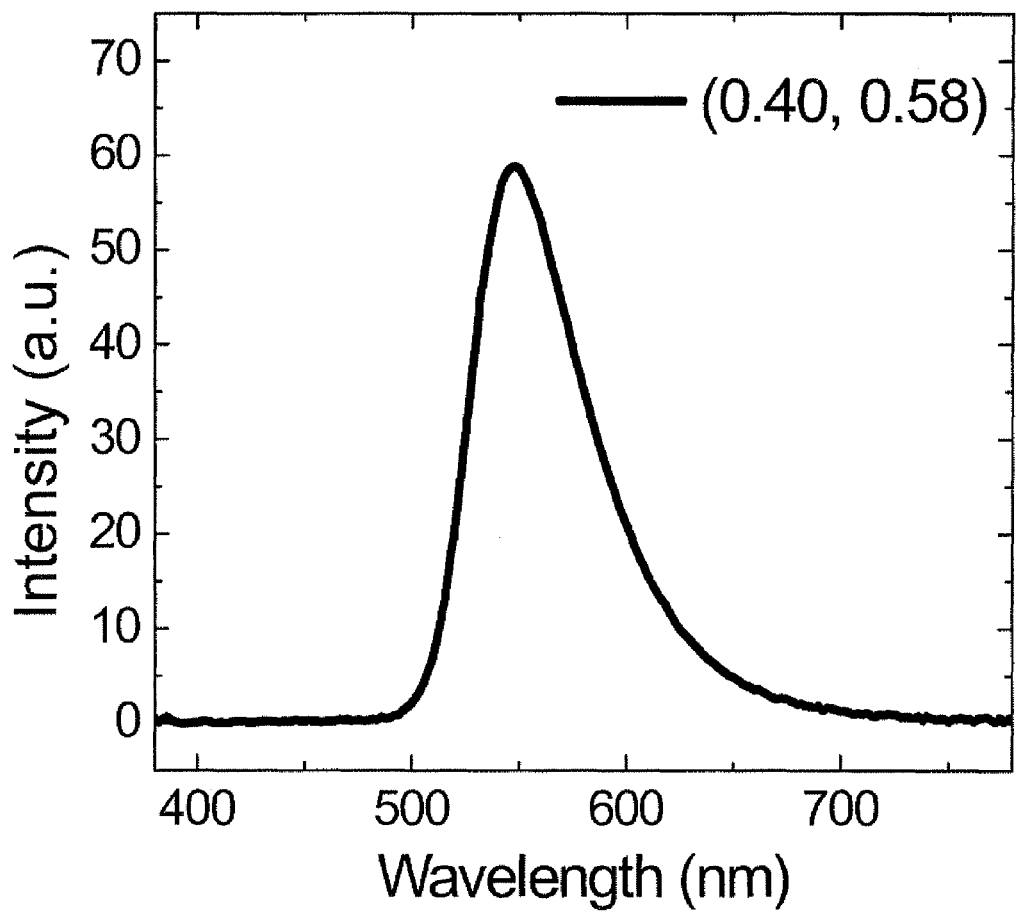
FIG. 38 shows the electroluminescent spectrum of the device: HIL4 [10 nm]/NPD [30 nm]/CBP:es-5, 6% [30 nm]/ CBP [5 nm]/Alq [45 nm]/LiF [0.5 nm]/Al [100 nm].
Figure 39:
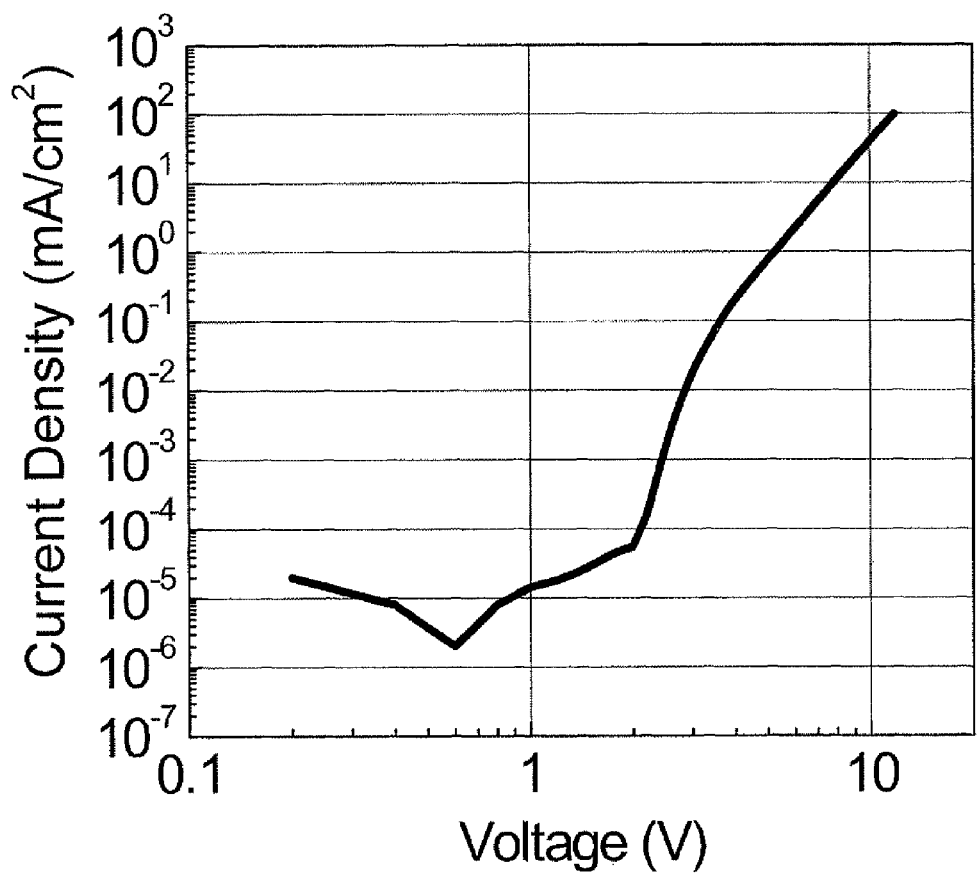
FIG. 39 shows the plot of current density vs. voltage for the device: HIL4 [10 nm]/NPD [30 nm]/CBP:es-5, 15% [30 nm]/ 2,3,6,7,10,11-hexaphenyltriphenylene[5 nm]/Alq [45 nm]/ LiF [0.5 nm]/Al [100 nm].
Figure 40:
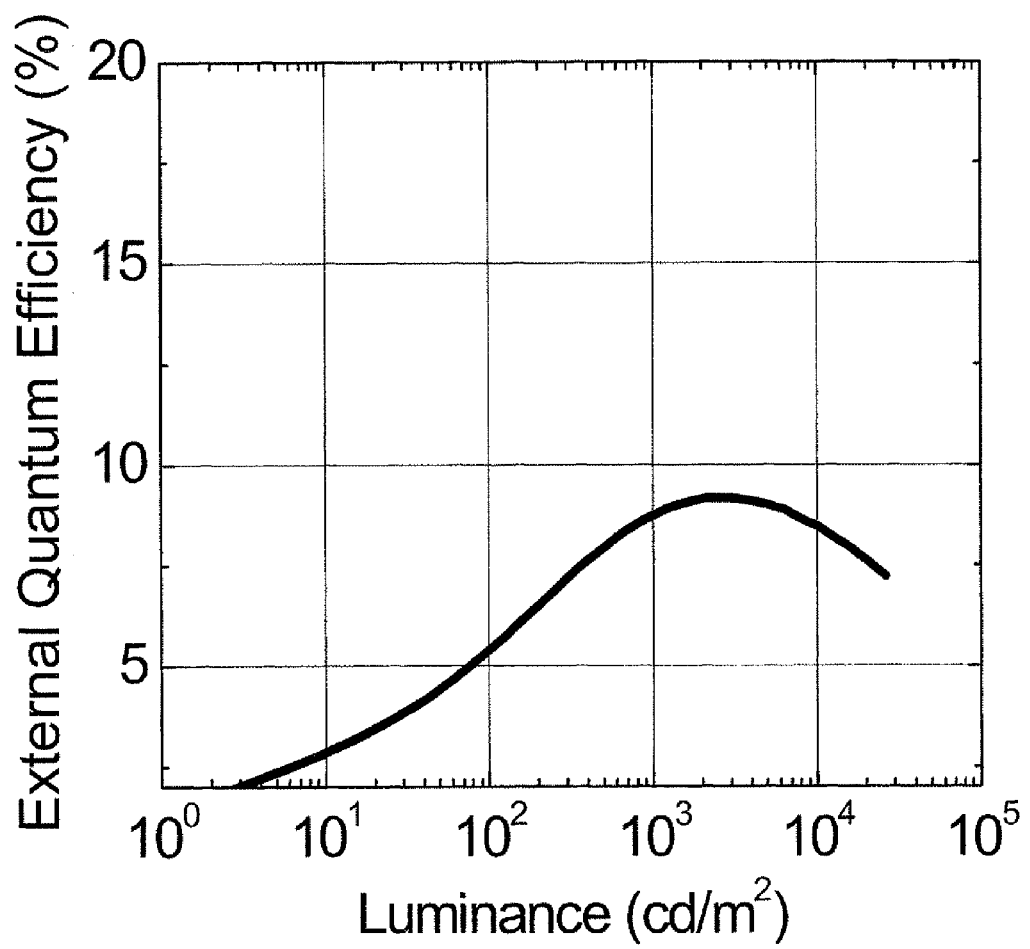
FIG. 40 shows the plot of external quantum efficiency vs. luminance for the device: HIL4 [10 nm]/NPD [30 nm]/CBP: es-5, 15% [30 nm]/2,3,6,7,10,11-hexaphenyltriphenylene[5 nm]/Alq [45 nm]/LiF [0.5 nm]/Al [100 nm].
Figure 41:
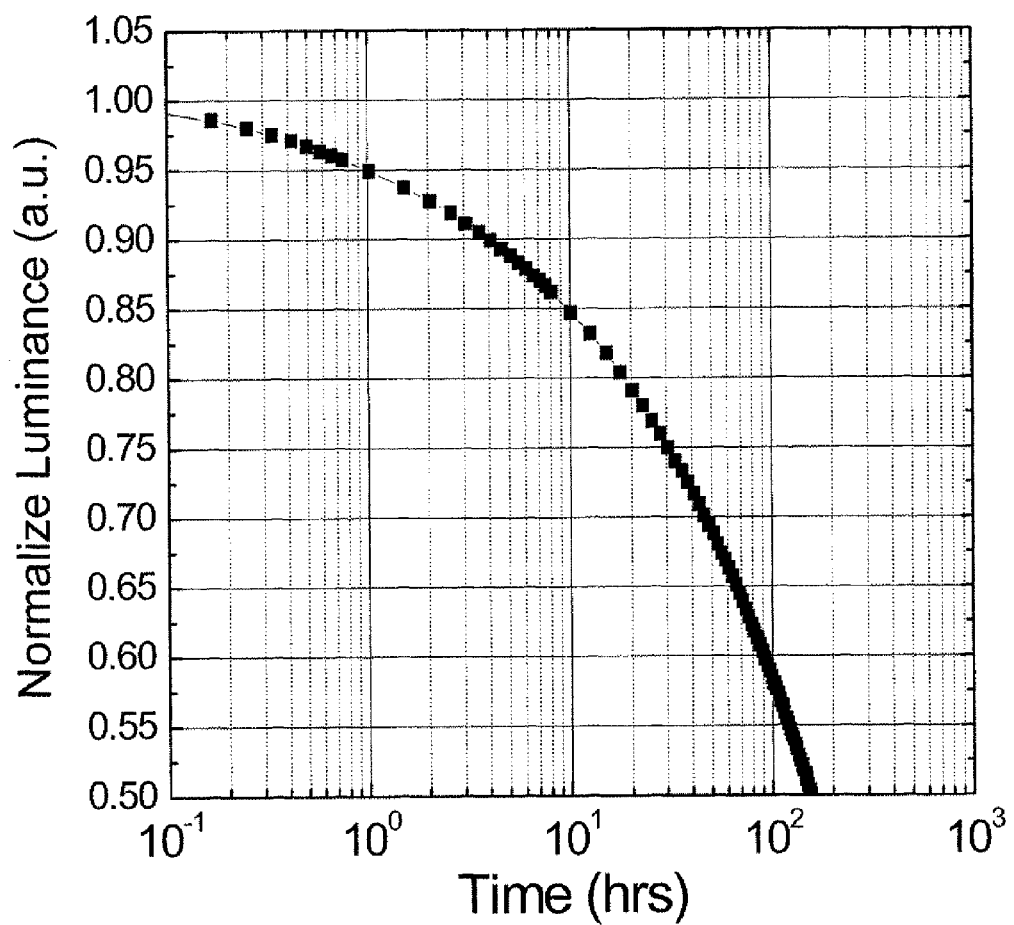
FIG. 41 shows the plot of normalized luminance vs. time for the device: HIL4 [10 nm]/NPD [30 nm]/CBP:es-5, 15% [30 nm]/2,3,6,7,10,11-hexaphenyltriphenylene[5 nm]/Alq [45 nm]/LiF [0.5 nm]/Al [100 nm].
Figure 42:
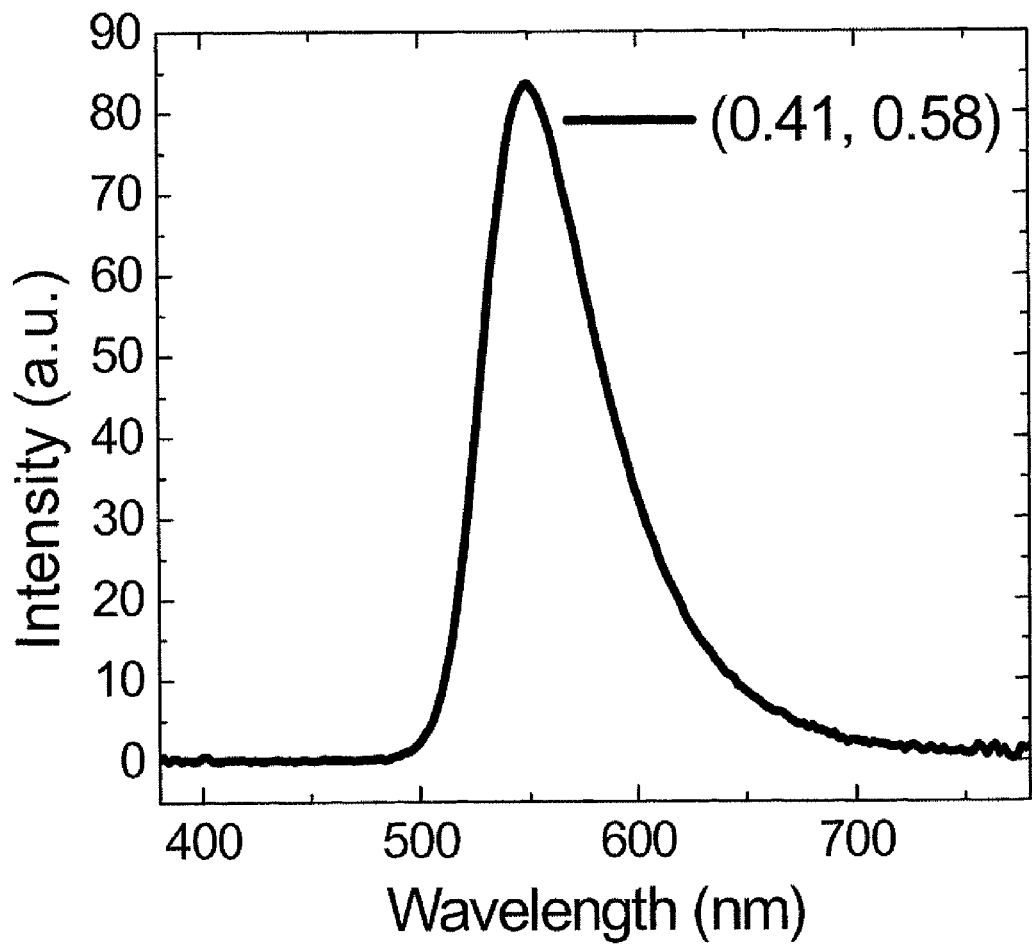
FIG. 42 shows the electroluminescent spectrum of the device: HIL4 [10 nm]/NPD [30 nm]/CBP:es-5, 15% [30 nm]/ 2,3,6,7,10,11-hexaphenyltriphenylene[5 nm]/Alq [45 nm]/ LiF [0.5 nm]/Al [100 nm].
Figure 43:
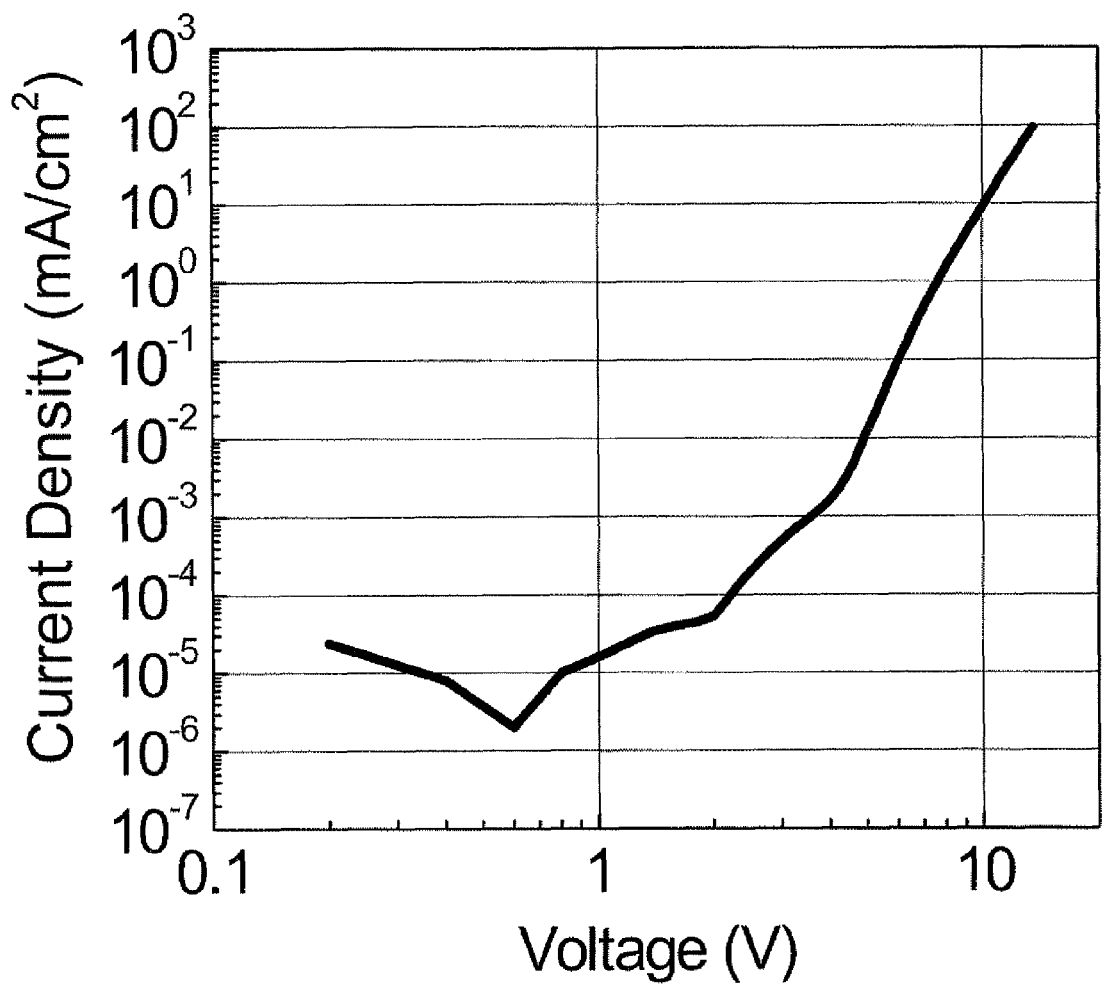
FIG. 43 shows the plot of current density vs. voltage for the device: HIL4 [10 nm]/NPD [30 nm]/CBP:es-5, 6% [30 nm]/ Alq [45 nm]/LiF [0.5 nm]/Al [100 nm].
Figure 44:
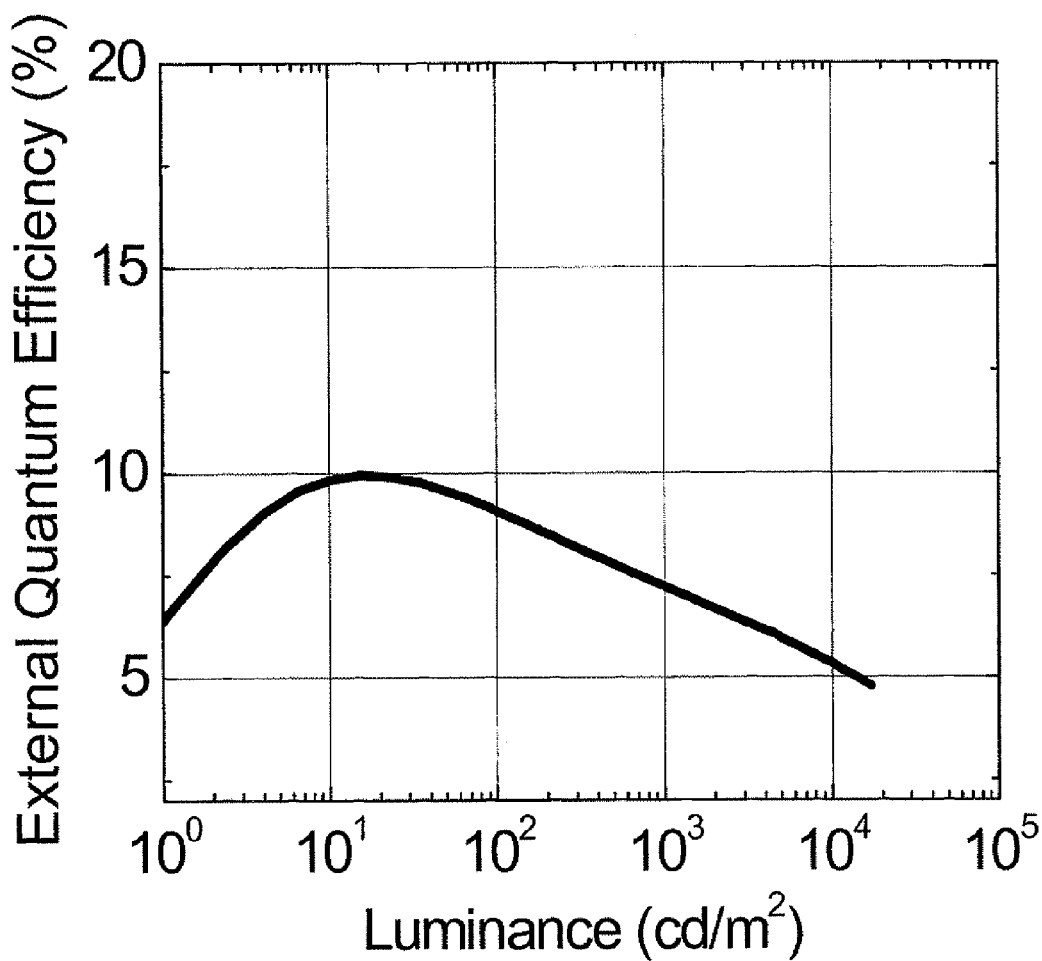
FIG. 44 shows the plot of external quantum efficiency vs. luminance for the device: HIL4 [10 nm]/NPD [30 nm]/CBP: es-5, 6% [30 nm]/Alq [45 nm]/LiF [0.5 nm]/Al [100 nm].
Figure 45:
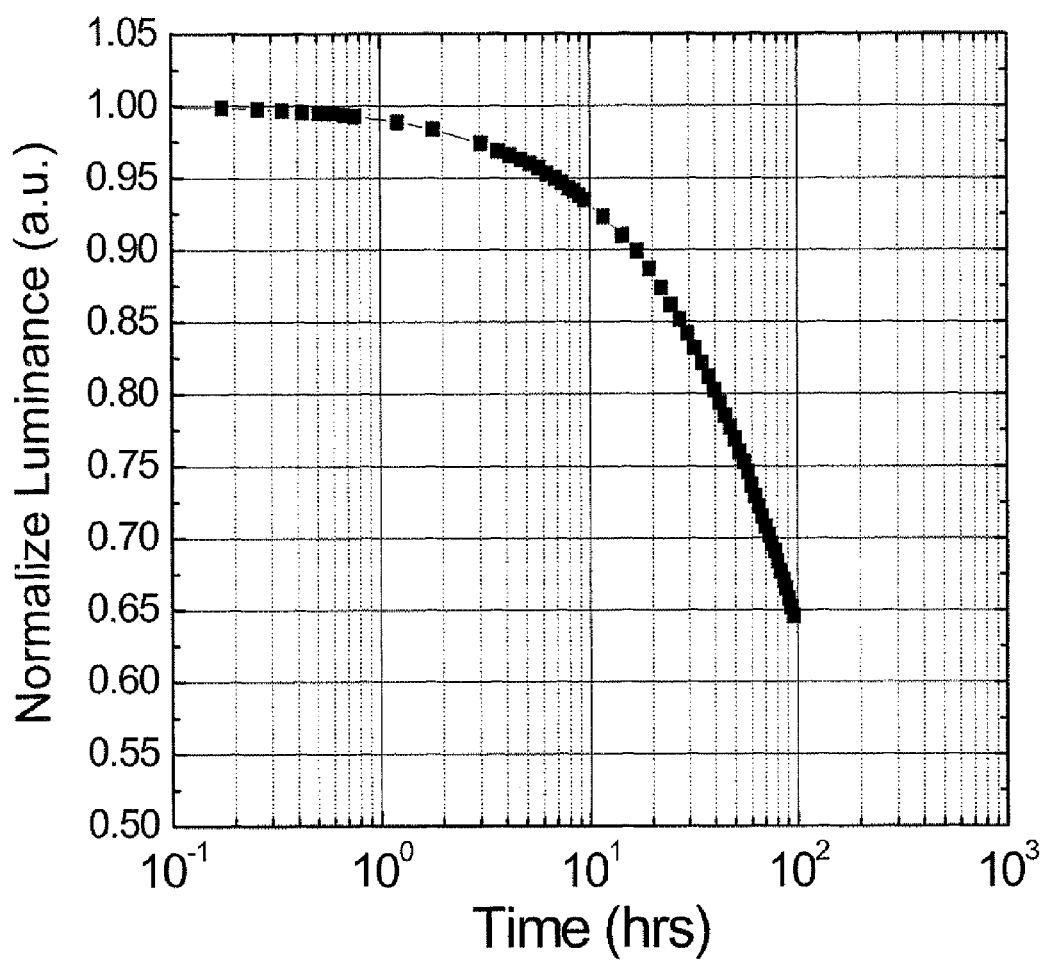
FIG. 45 shows the plot of normalized luminance vs. time for the device: HIL4 [10 nm]/NPD [30 nm]/CBP:es-5, 6% [30 nm]/Alq [45 nm]/LiF [0.5 nm]/Al [100 nm].
Figure 46:
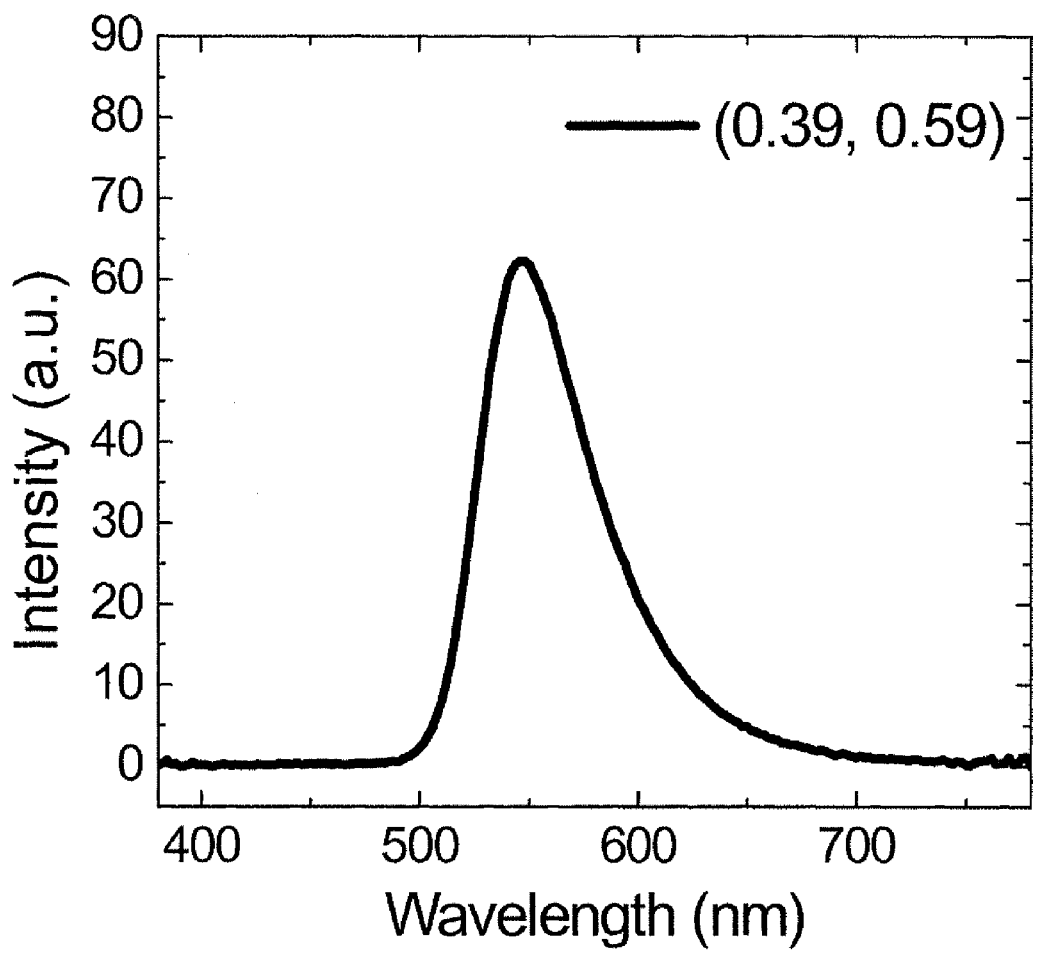
FIG. 46 shows the electroluminescent spectrum of the device: HIL4 [10 nm]/NPD [30 nm]/CBP:es-5, 6% [30 nm]/ Alq [45 nm]/LiF [0.5 nm]/Al [100 nm].
Figure 47:
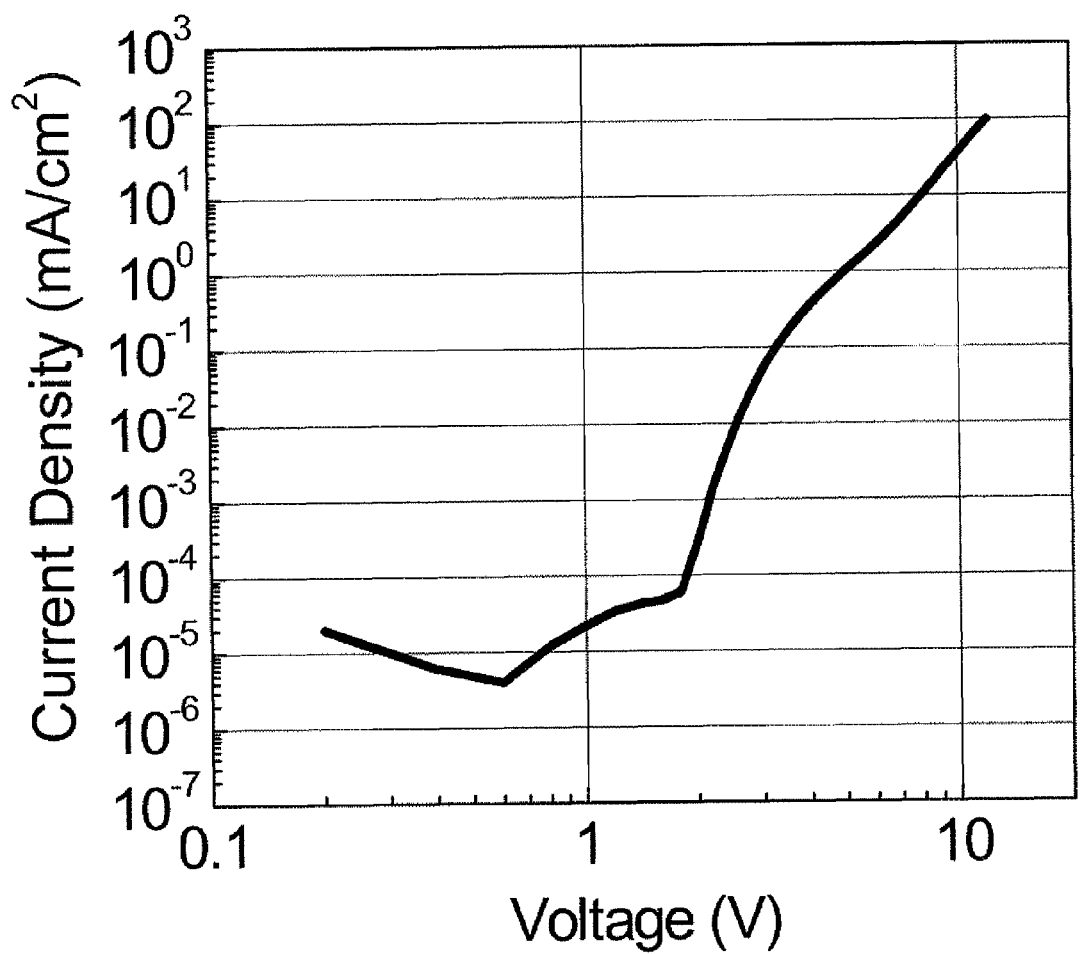
FIG. 47 shows the plot of current density vs. voltage for the device: HIL4 [10 nm]/NPD [30 nm]/CBP:es-5, 15% [30 nm]/ Alq [45 nm]/LiF [0.5 nm]/Al [100 nm].
Figure 48:
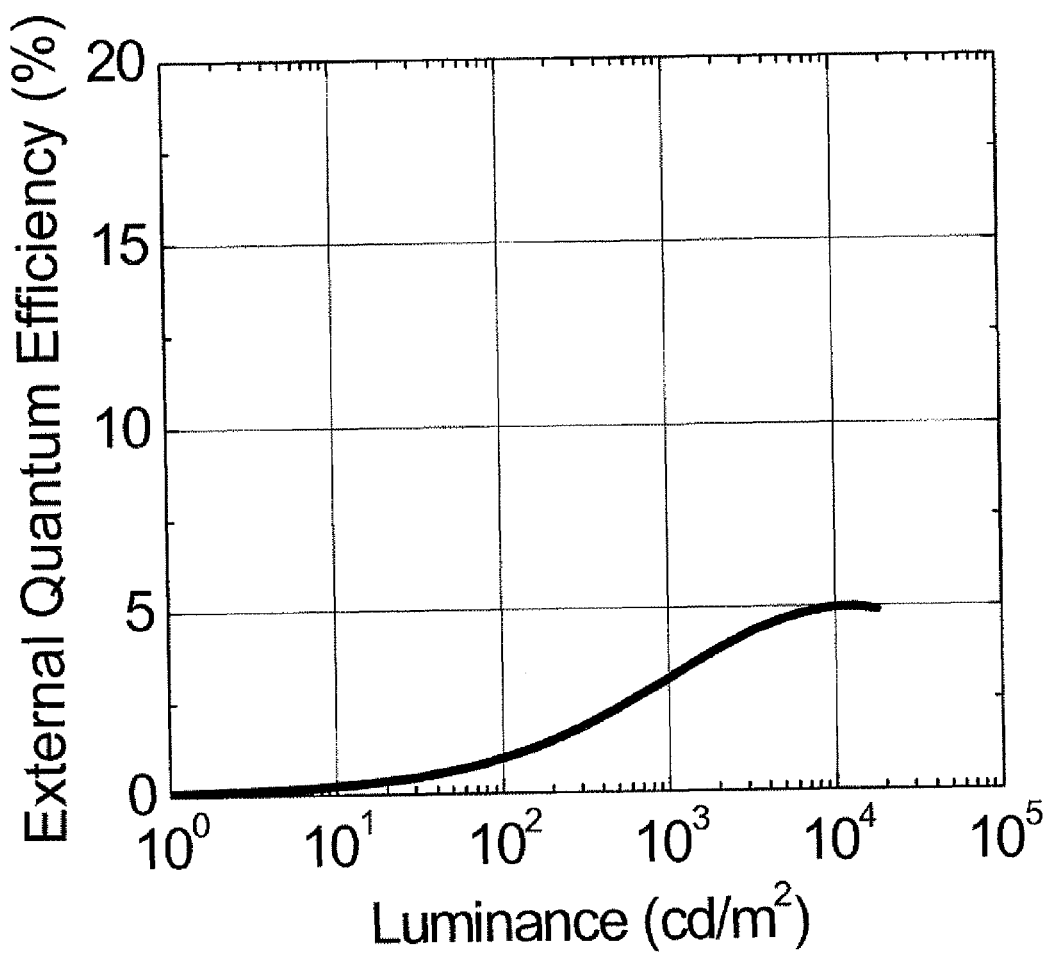
FIG. 48 shows the plot of external quantum efficiency vs. luminance for the device: HIL4 [10 nm]/NPD [30 nm]/CBP: es-5, 15% [30 nm]/Alq [45 nm]/LiF [0.5 nm]/Al [100 nm].
Figure 49:
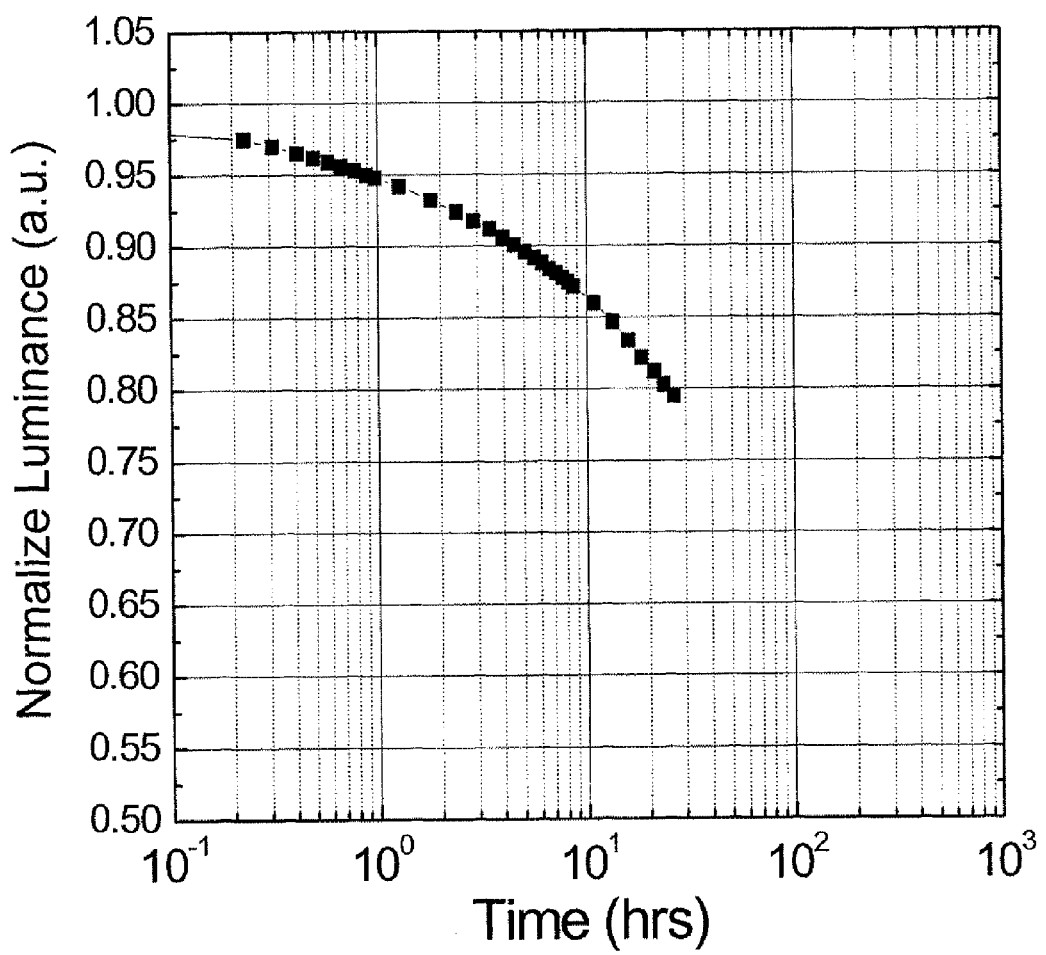
FIG. 49 shows the plot of normalized luminance vs. time for the device: HIL4 [10 nm]/NPD [30 nm]/CBP:es-5, 15% [30 nm]/Alq [45 nm]/LiF [0.5 nm]/Al [100 nm].
Figure 50:
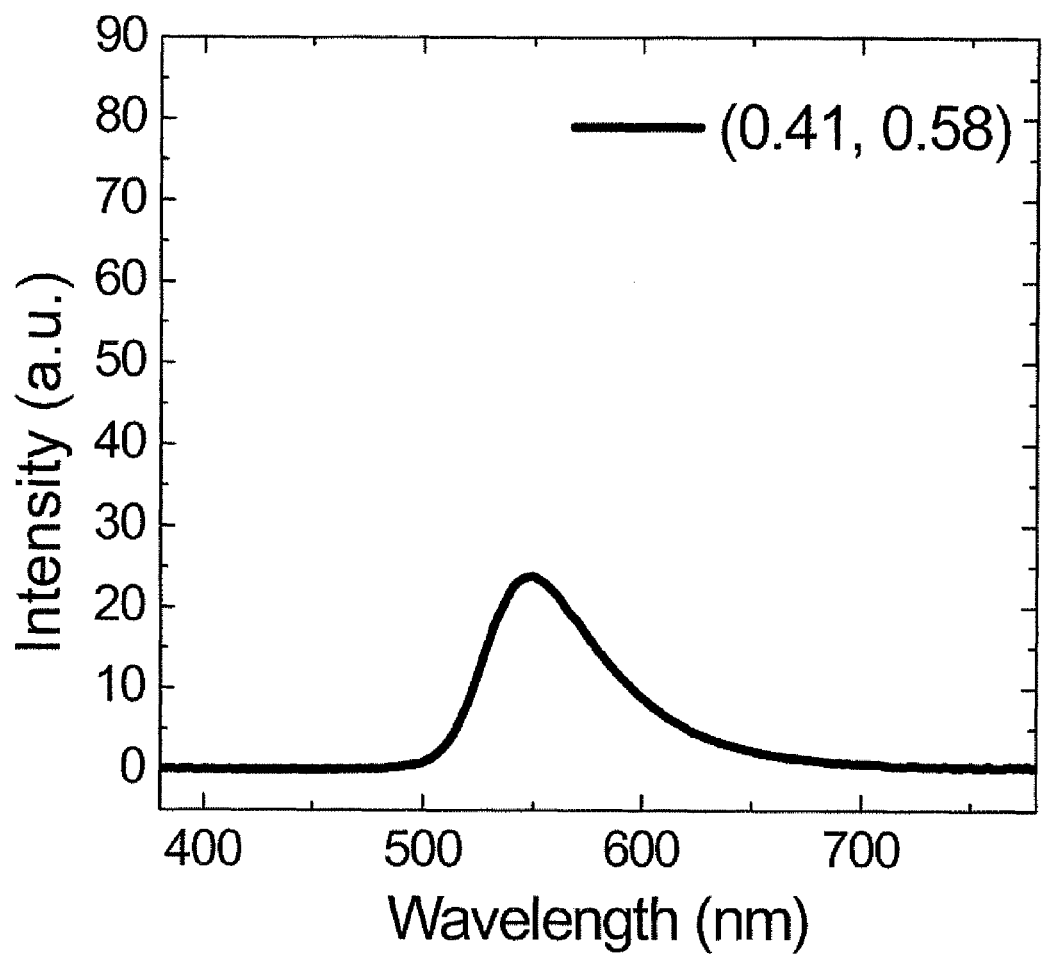
FIG. 50 shows the electroluminescent spectrum of the device: HIL4 [10 nm]/NPD [30 nm]/CBP:es-5, 15% [30 nm]/ Alq [45 nm]/LiF [0.5 nm]/Al [100 nm].
Figure 51:
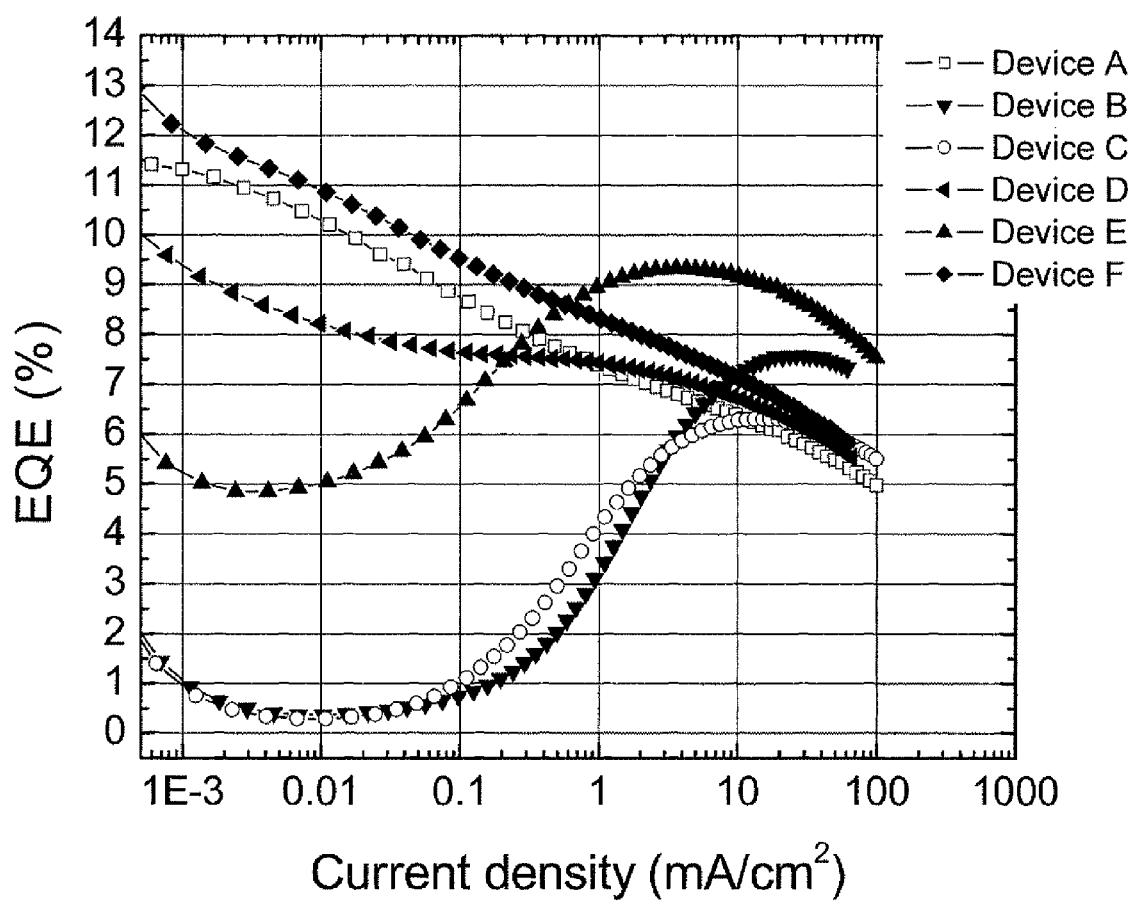
FIG. 51 shows the plot of external quantum efficiency vs. current density for the devices A, B, C, D, E and F.
Figure 52:
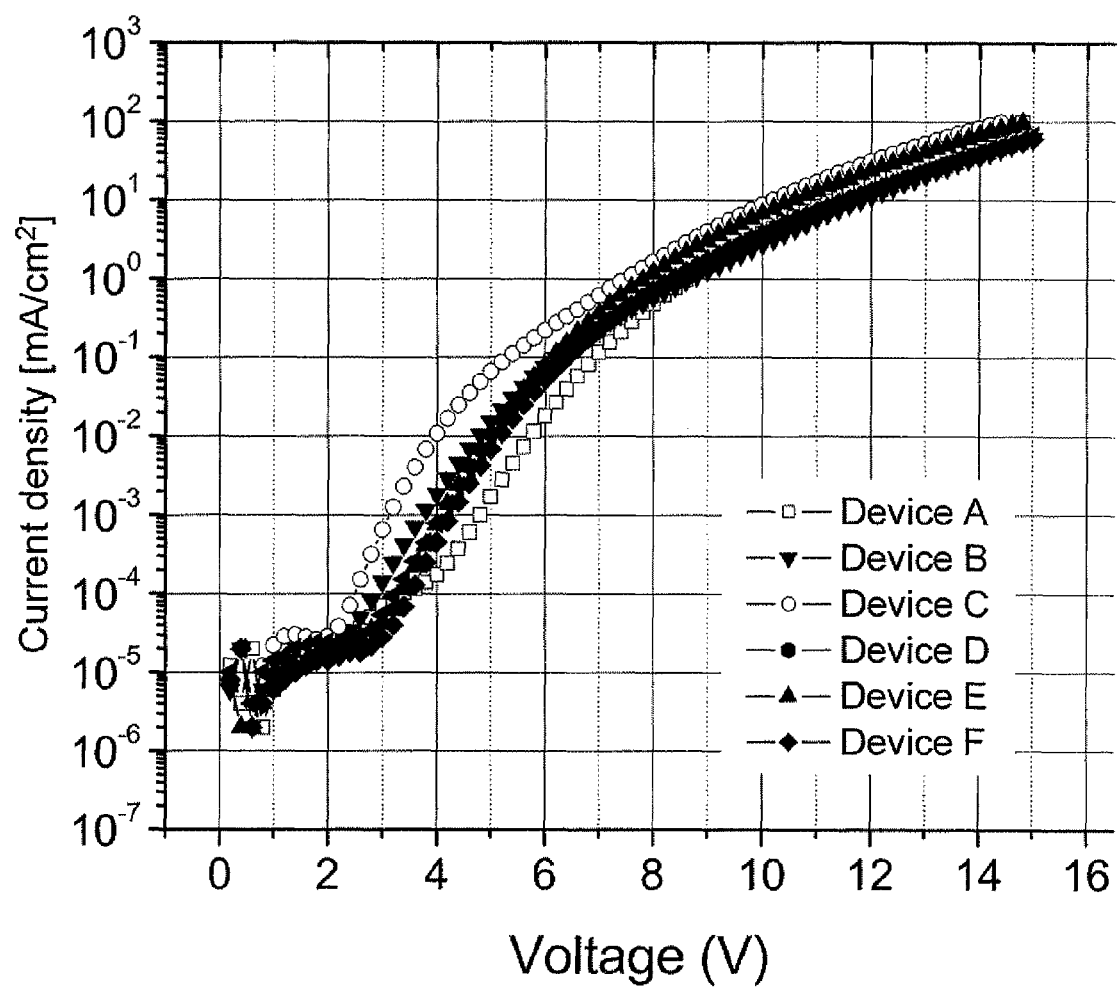
FIG. 52 shows the plot of current density vs. voltage for the devices A, B, C, D, E and F.
Figure 53:
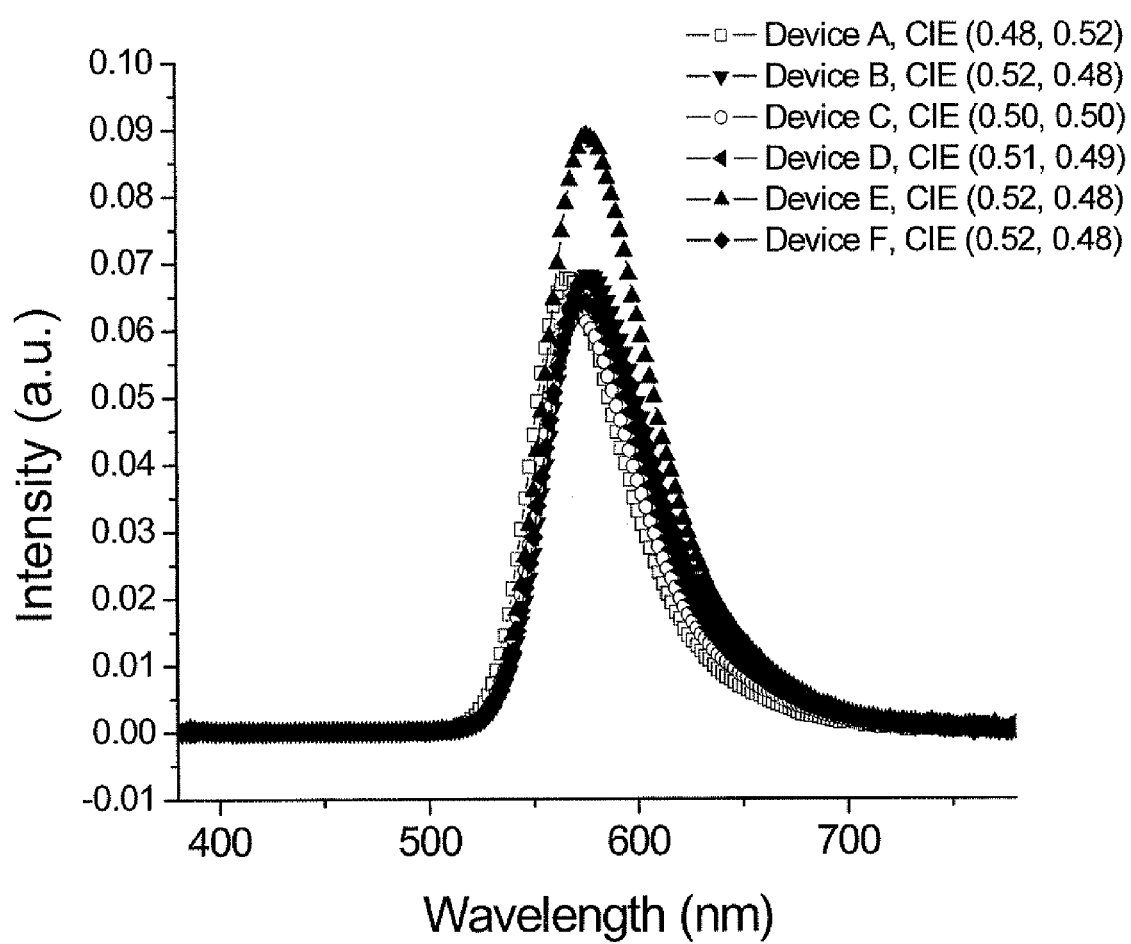
FIG. 53 shows the electroluminescent spectra of the devices A, B, C, D, E and F.
Figure 54:
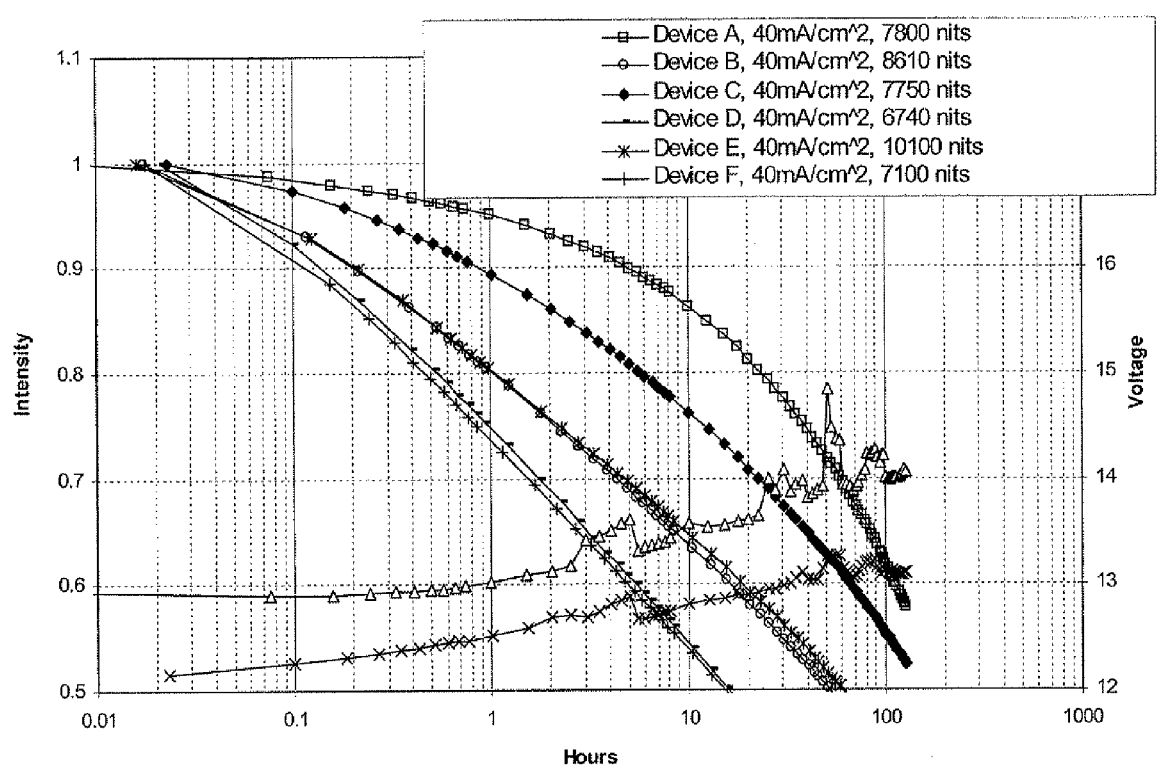
FIG. 54 shows plot of normalized luminance vs. time for the devices A, B, C, D, E and F.
Figure 55:
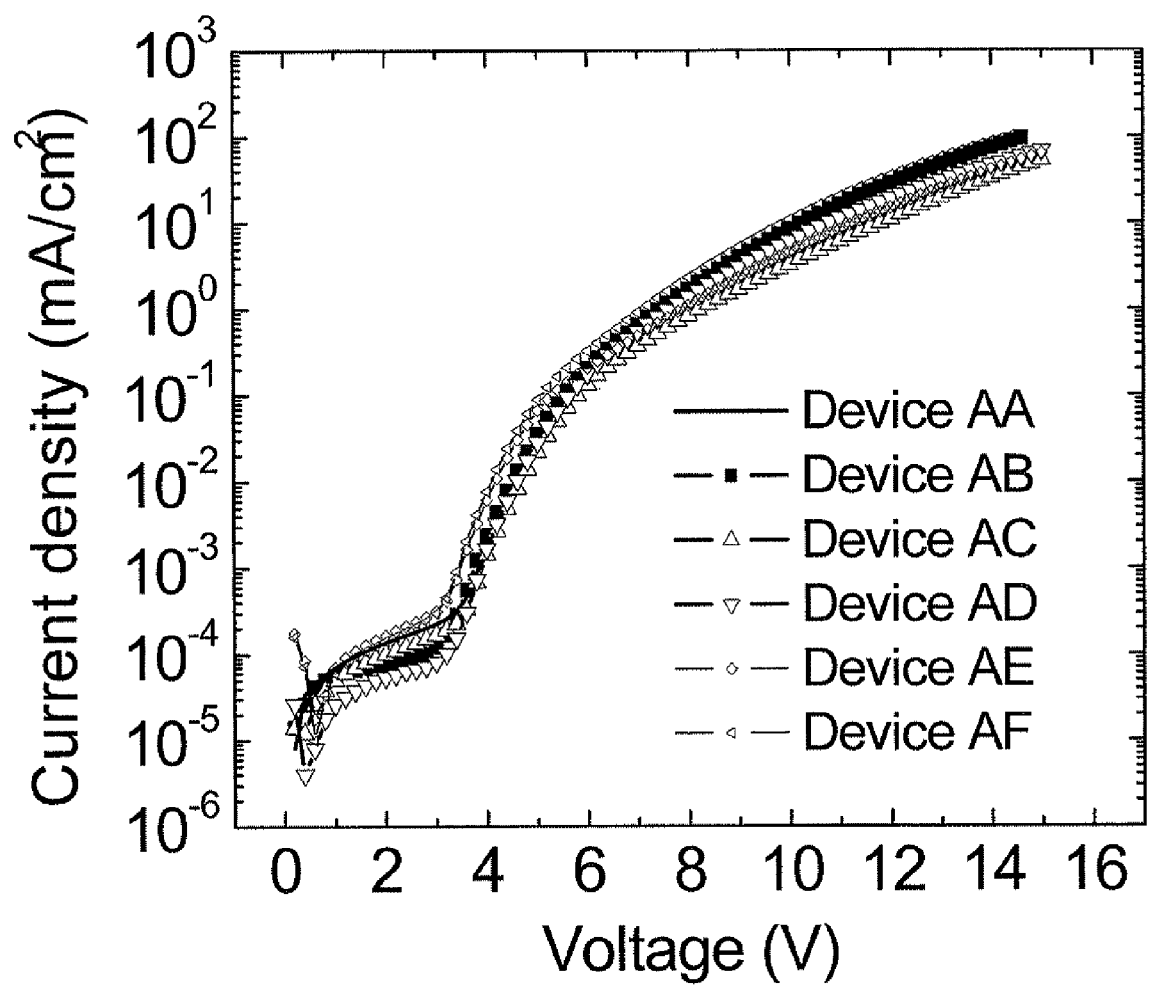
FIG. 55 shows the plot of current density vs. voltage for the devices AA, AB, AC, AD, AE and AF.
Figure 56:
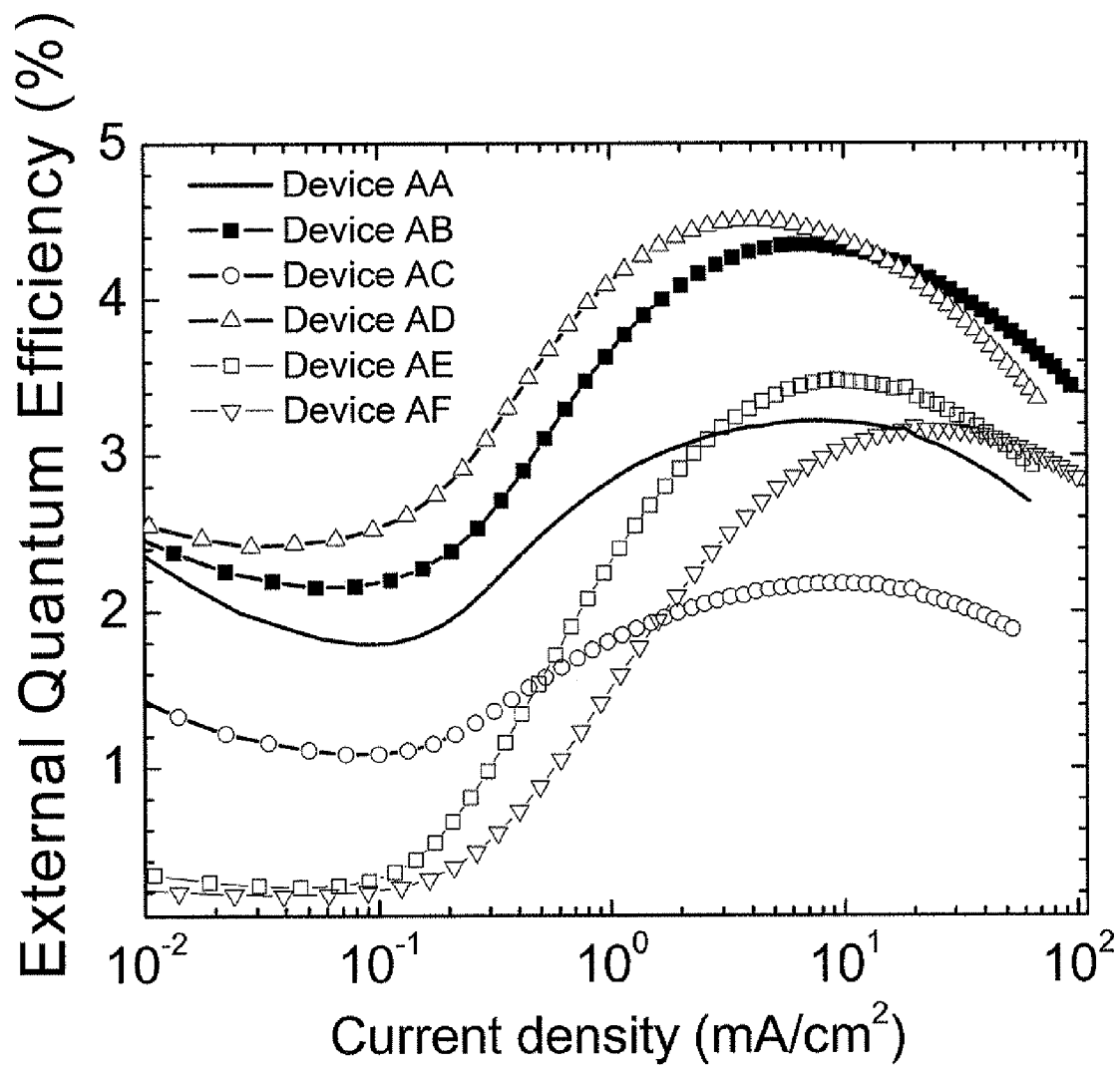
FIG. 56 shows the plot of external quantum efficiency vs. current density for the devices AA, AB, AC, AD, AE and AF.
Figure 57:
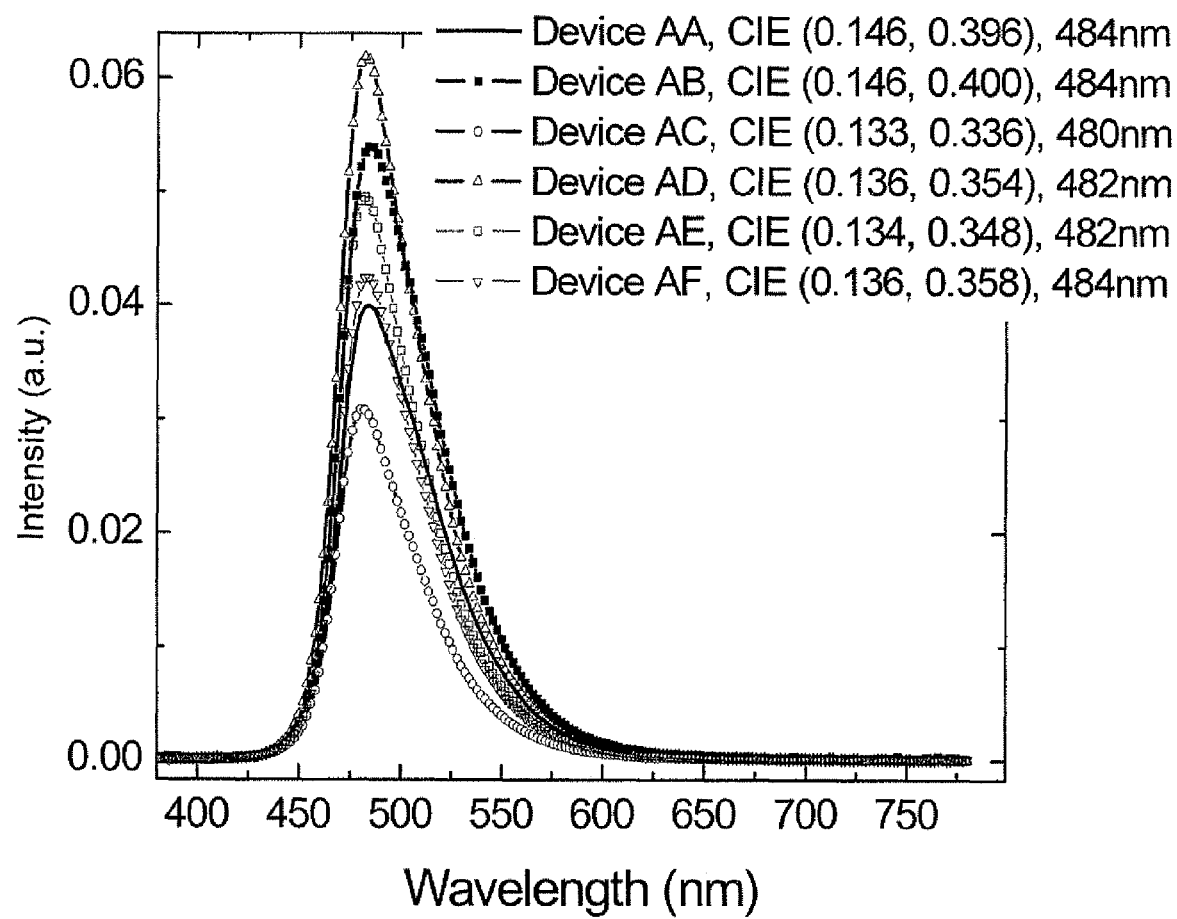
FIG. 57 shows the electroluminescent spectra of the devices AA, AB, AC, AD, AE and AF.
Figure 58:
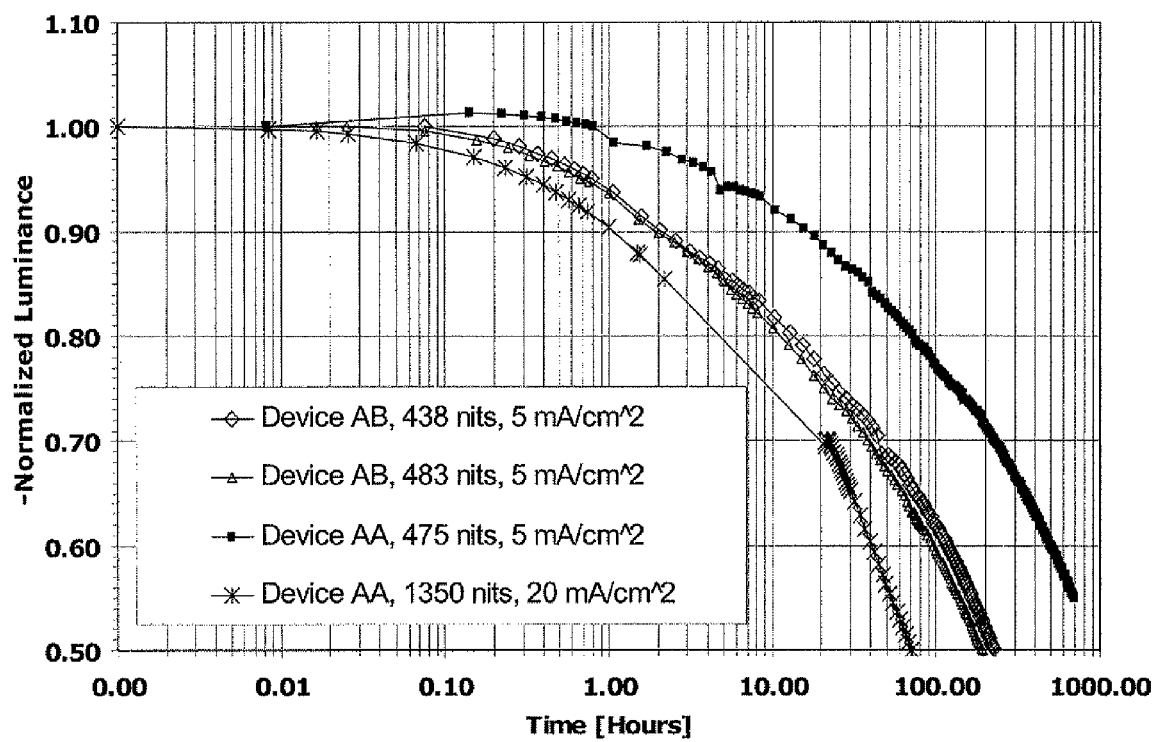
FIG. 58 shows the plot of normalized luminance vs. time for the devices AA and AB.
Figure 59:
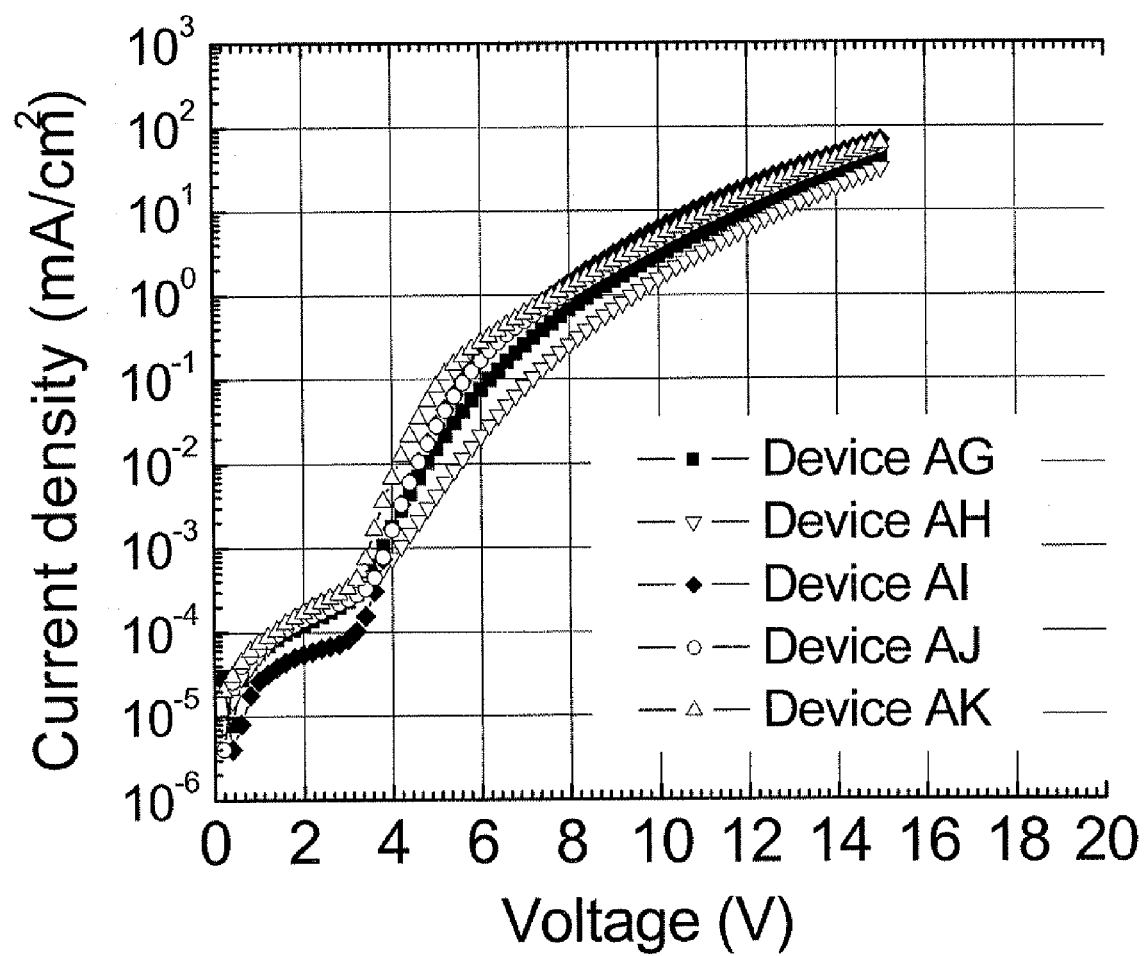
FIG. 59 shows the plot of current density vs. voltage for the devices AG, AH, AI, AJ and AK.
Figure 60:
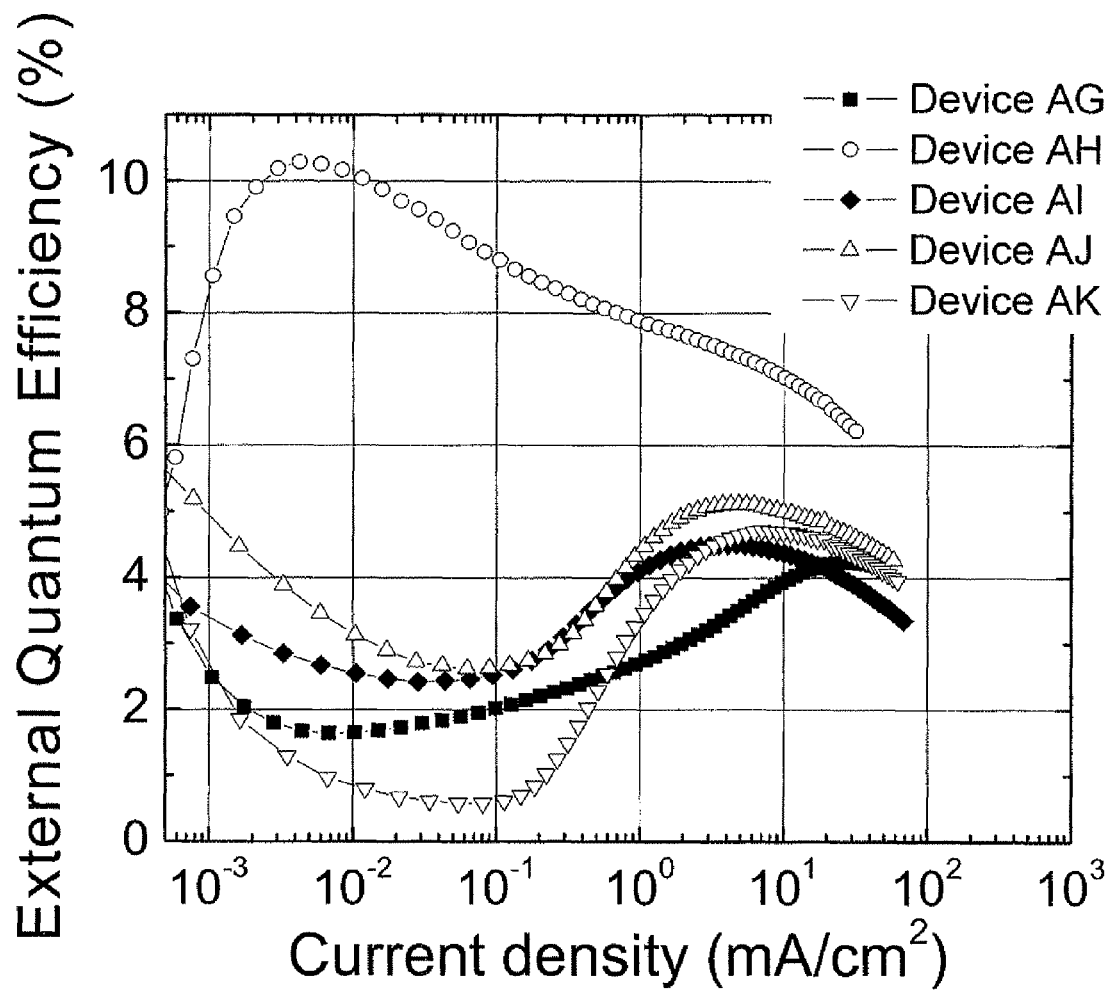
FIG. 60 shows the plot of external quantum efficiency vs. current density for the devices AG, AH, AI, AJ and AK.
Figure 61:
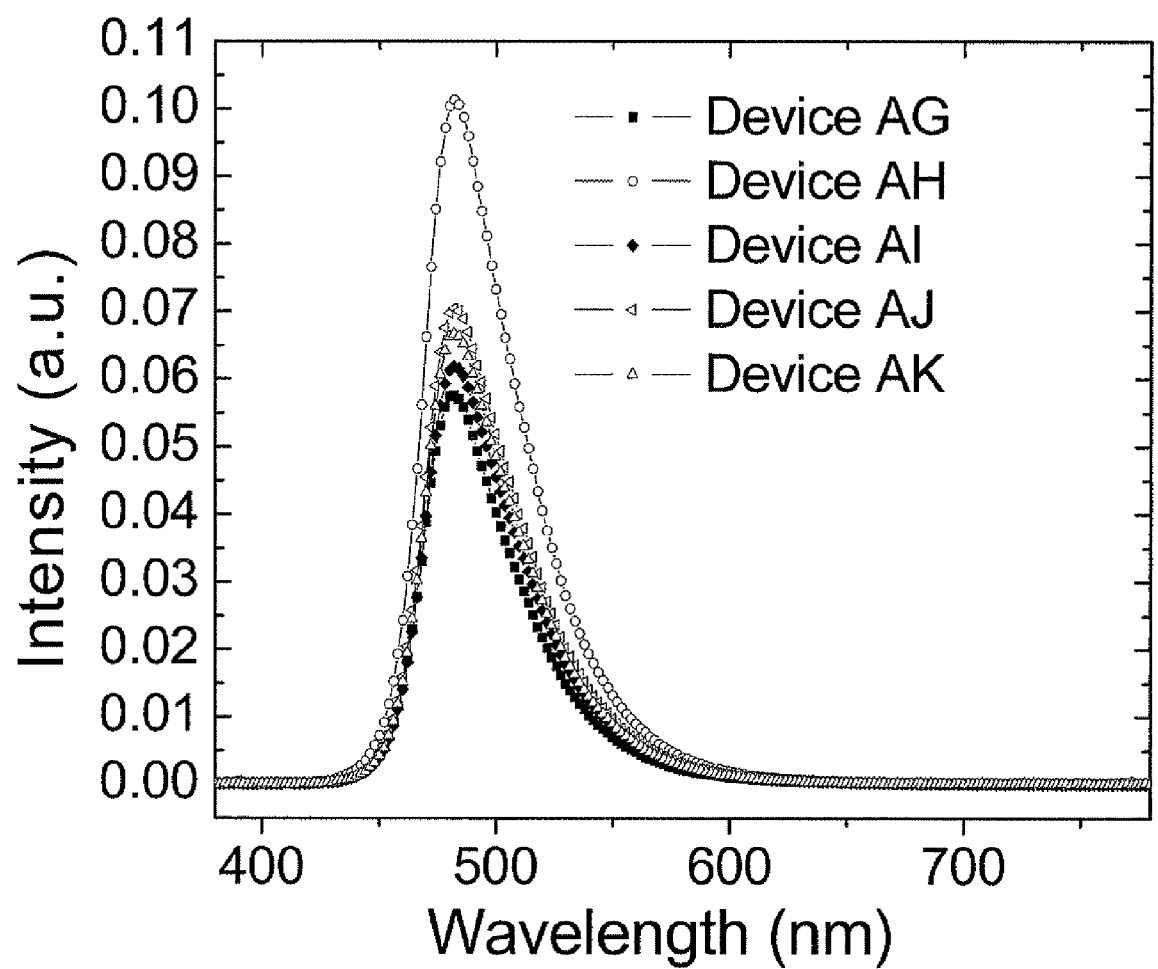
FIG. 61 shows the electroluminescent spectra of the devices AG, AH, AI, AJ and AK.
Figure 62:
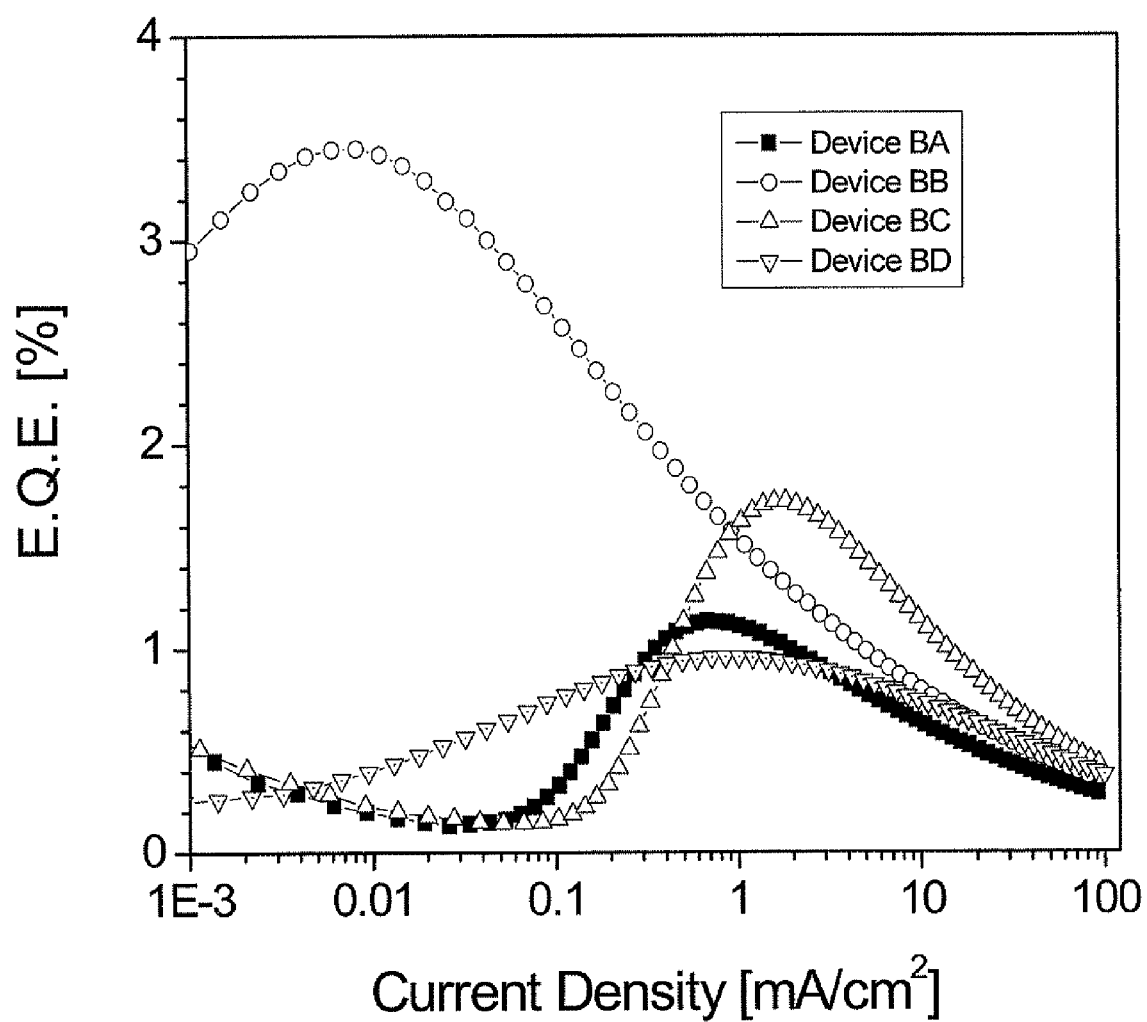
FIG. 62 shows the plot of external quantum efficiency vs. current density for the devices BA, BB, BC and BD.
Figure 63:
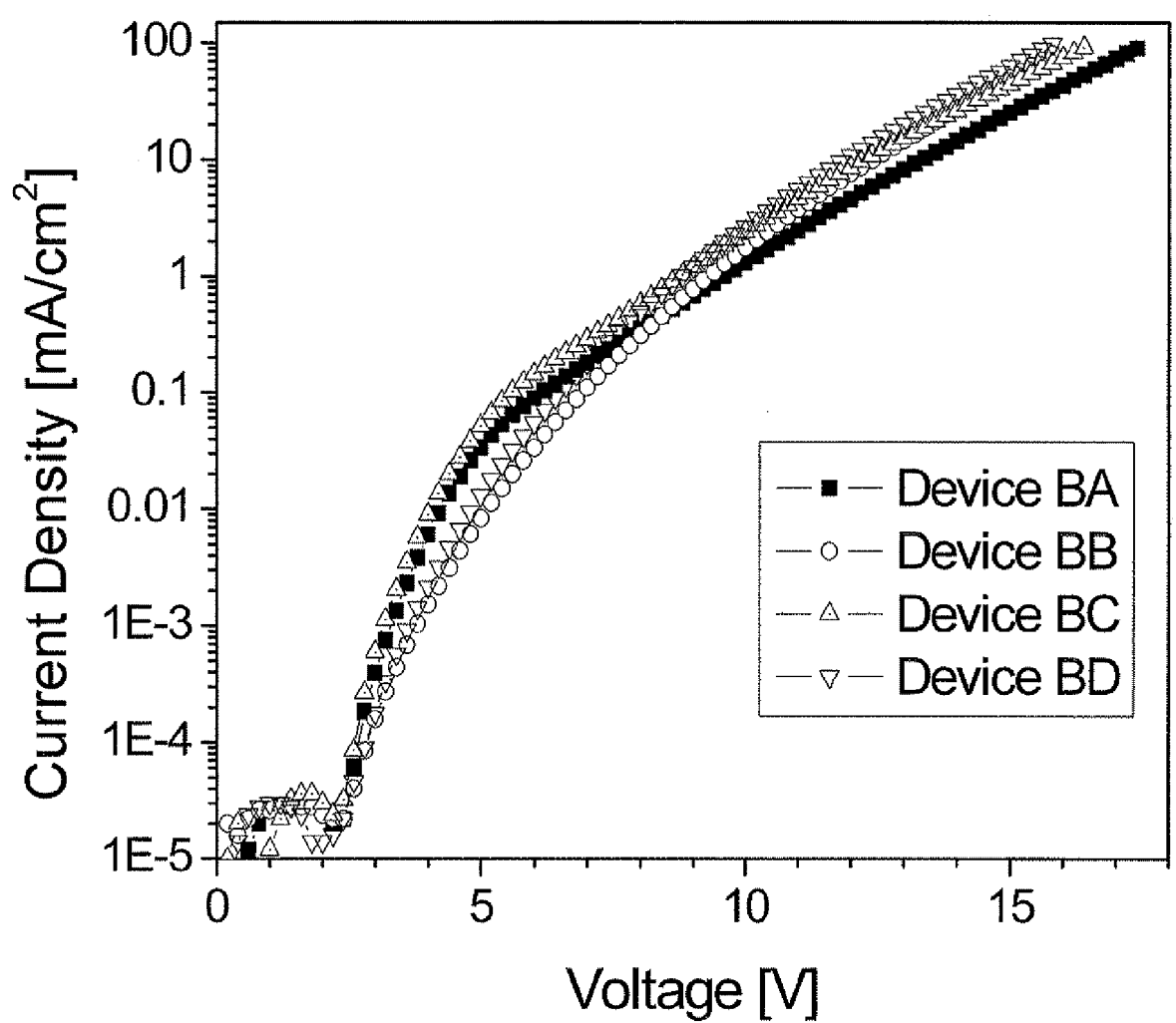
FIG. 63 shows the plot of current density vs. voltage for the devices BA, BB, BC, and BD.
Figure 64:
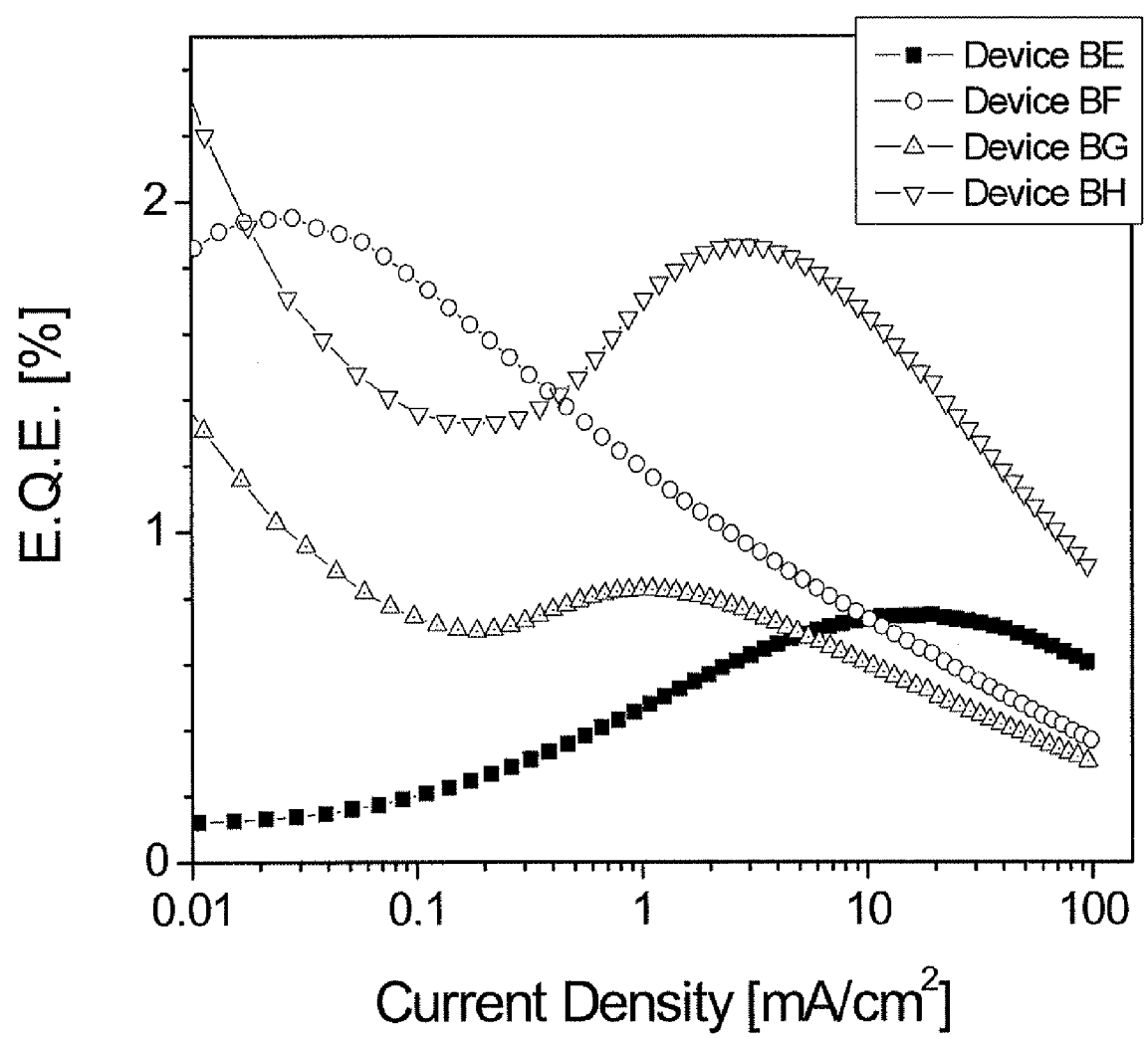
FIG. 64 shows the plot of external quantum efficiency vs. current density for the devices BE, BF, BG, and BH.
Figure 65:
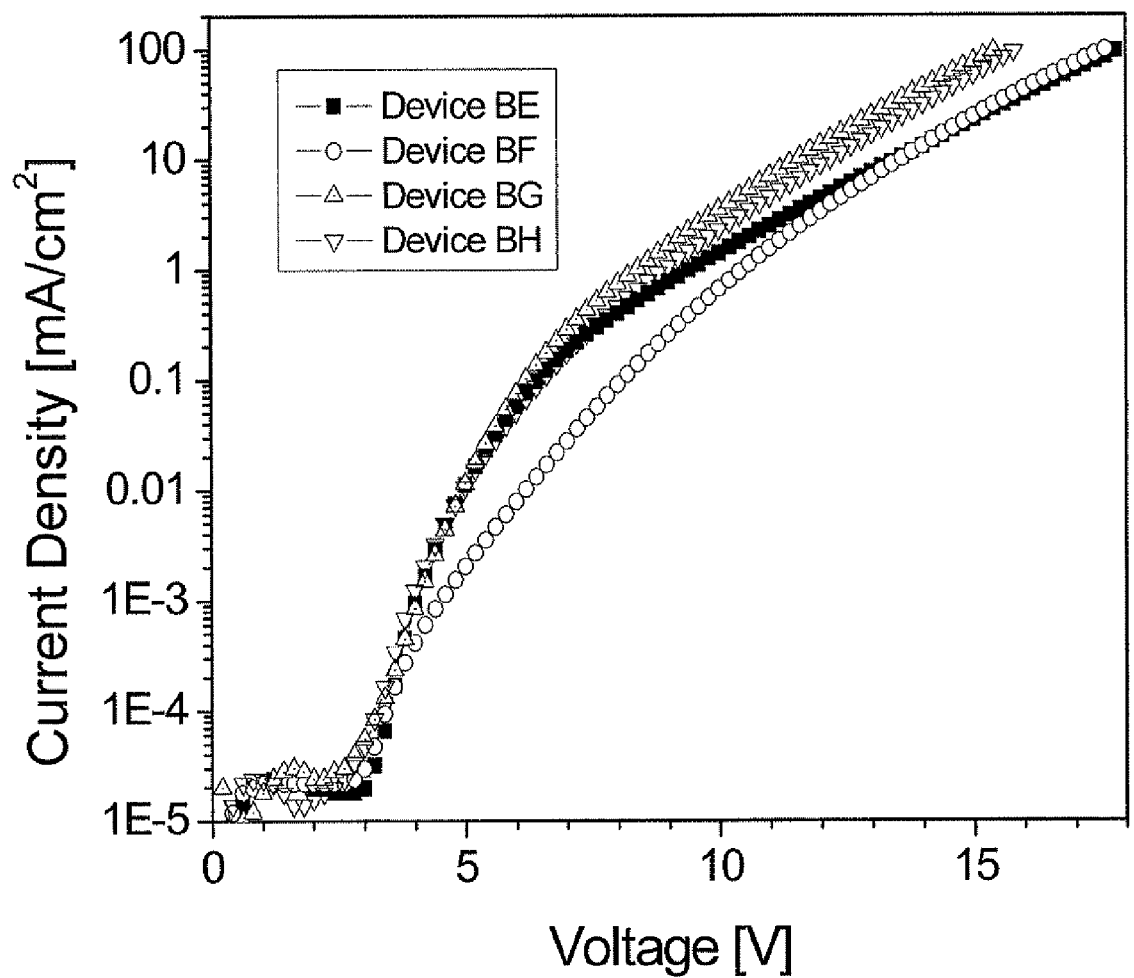
FIG. 65 shows the plot of current density vs. voltage for the devices BE, BF, BG, and BH.
Figure 66:
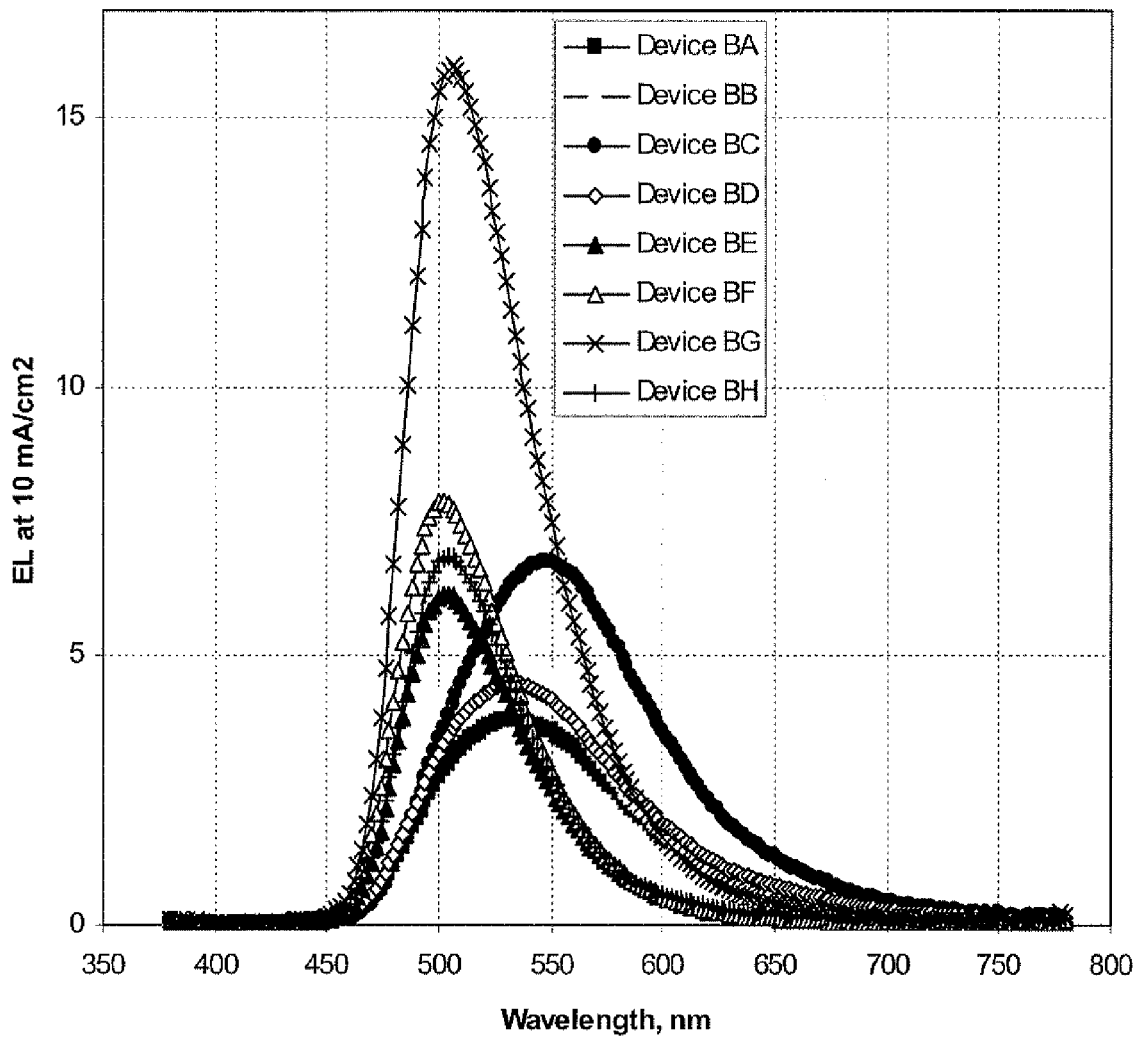
FIG. 66 shows the electroluminescent spectra of the devices BA, BB, BC, BD, BE, BF, BG, and BH.
Figure 67:
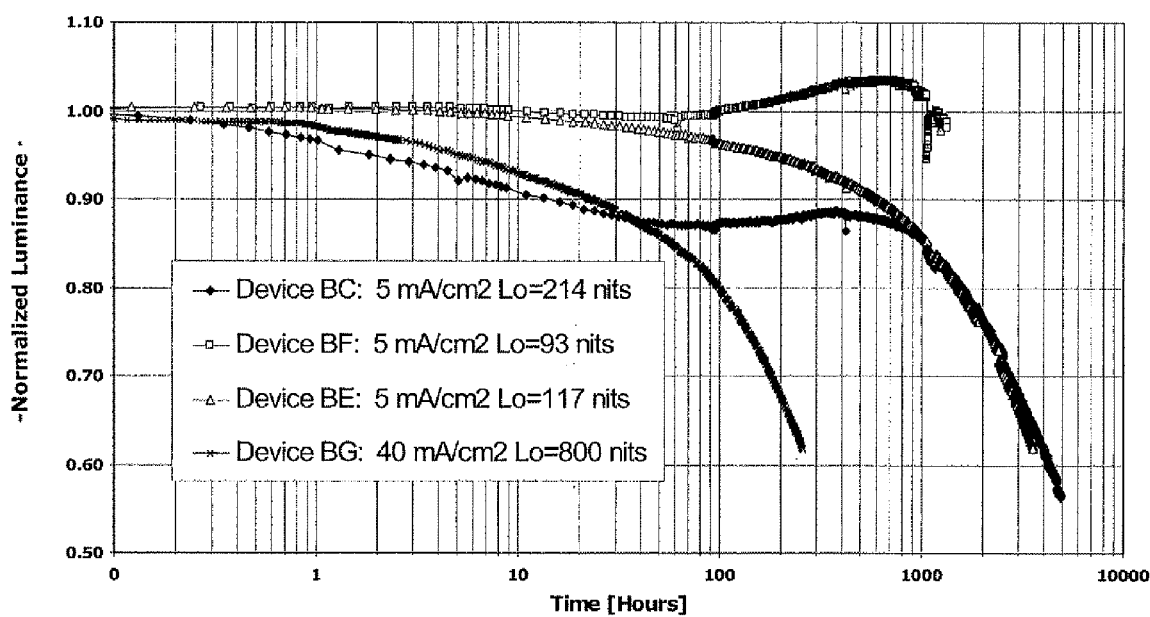
FIG. 67 shows the plot of normalized luminance vs. time for the devices BC, BF, BE, and BG.
Figure 68:
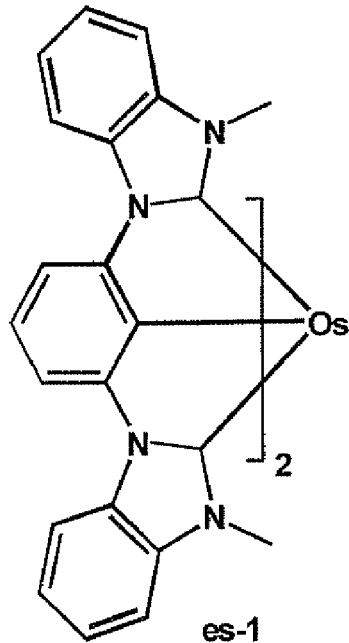
FIG. 68 shows the structures of compounds es-1, es-2, es-3, and es-4.
Figure 68:
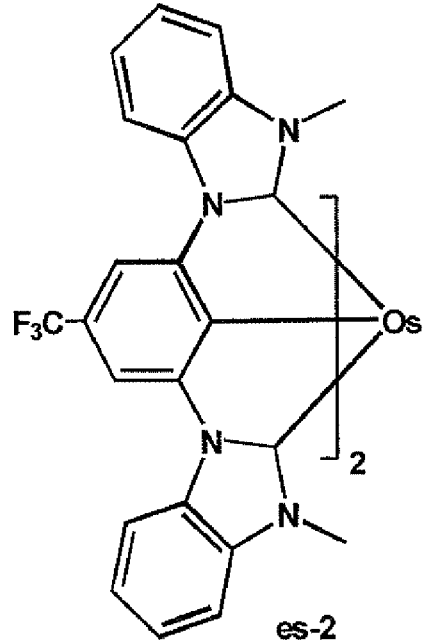
Figure 68:
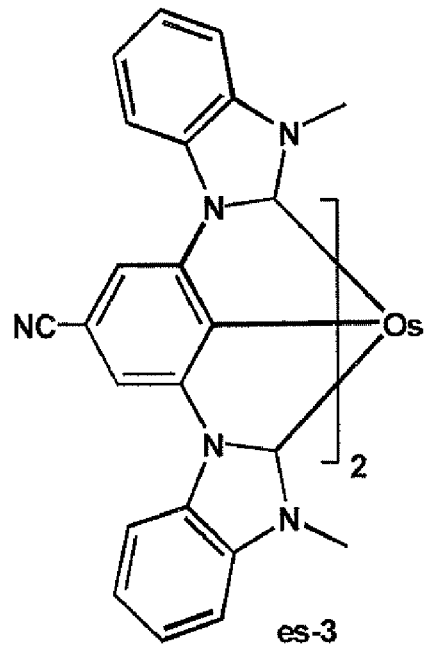
Figure 68:
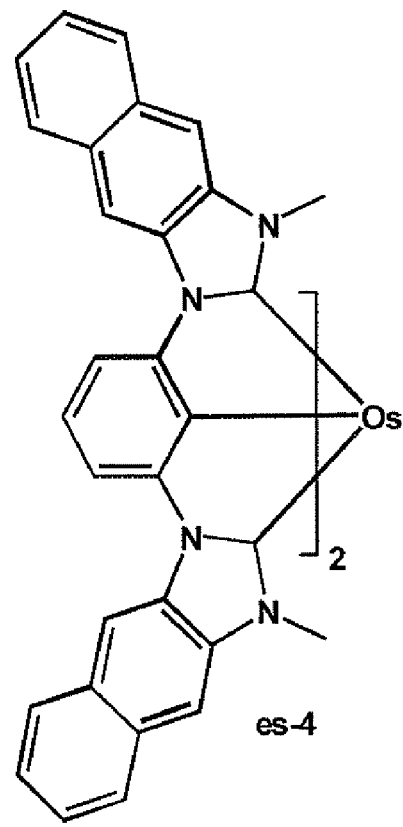
Figure 69:
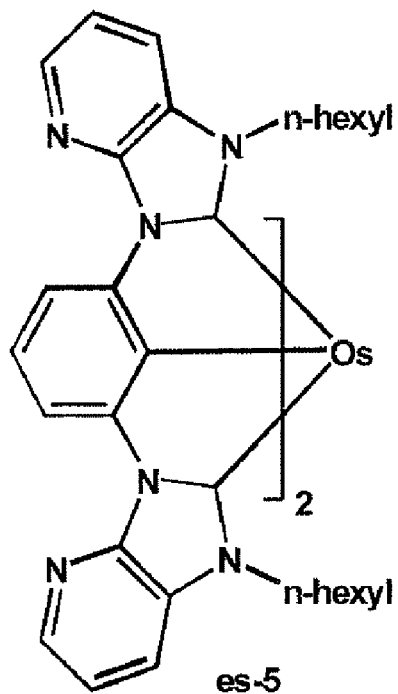
FIG. 69 shows the structures of compounds es-5, es-6, es-7, and es-8.
Figure 69:
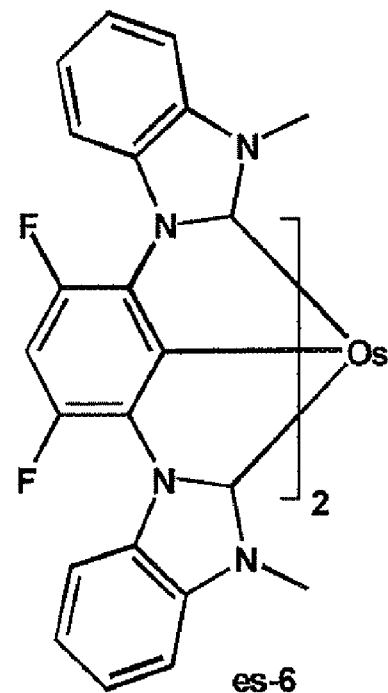
Figure 69:
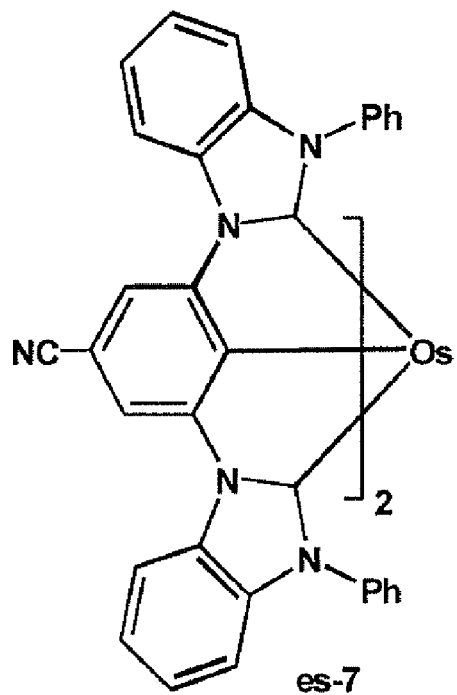
Figure 69:
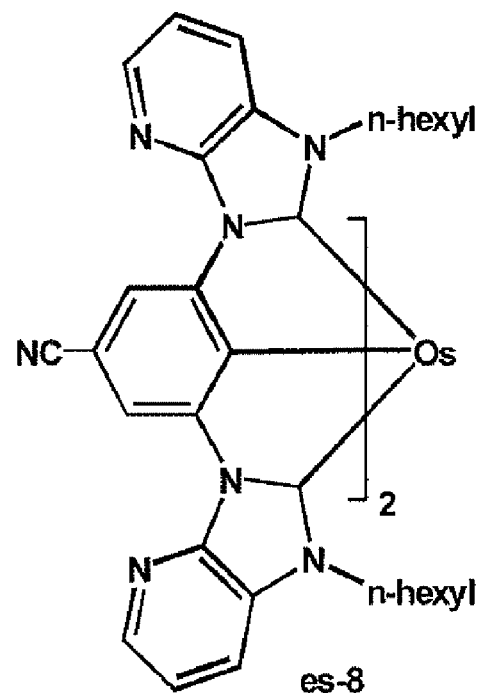

The device characteristics for the devices set forth in Table 2 were measured and are set forth in FIGS. 5 to 69.

Example 9

Figure 70:
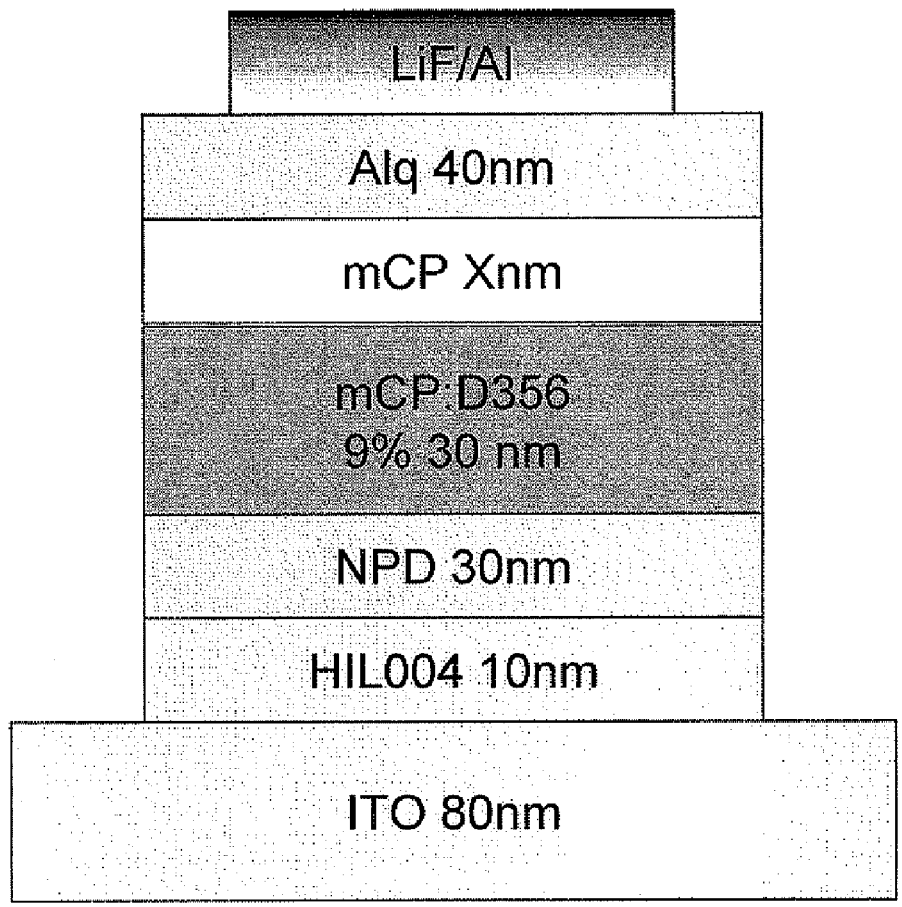
FIG. 70 shows the device structure for Example 9.
Figure 71:
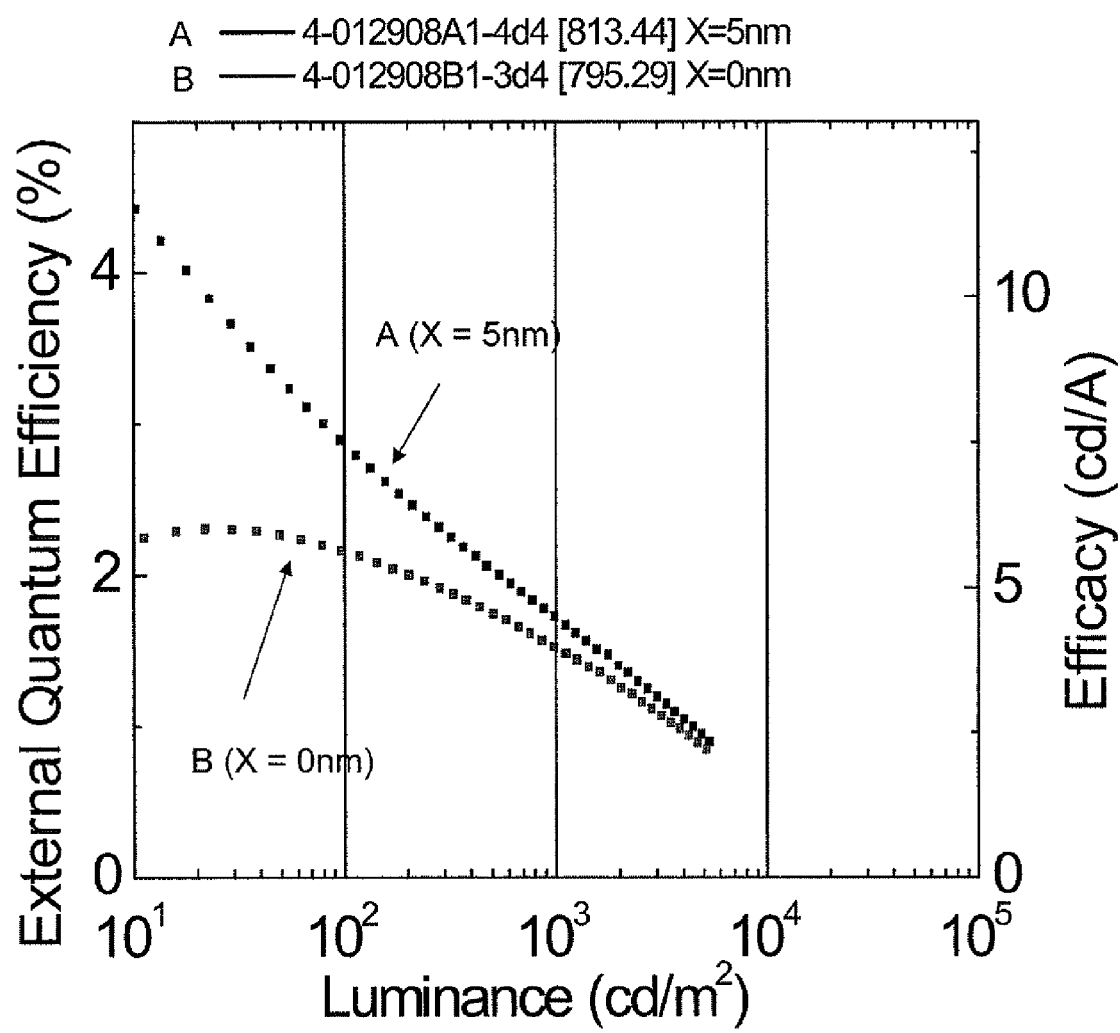
FIG. 71 shows the plot of external quantum efficiency versus luminance for the devices of Example 9.
Figure 72:
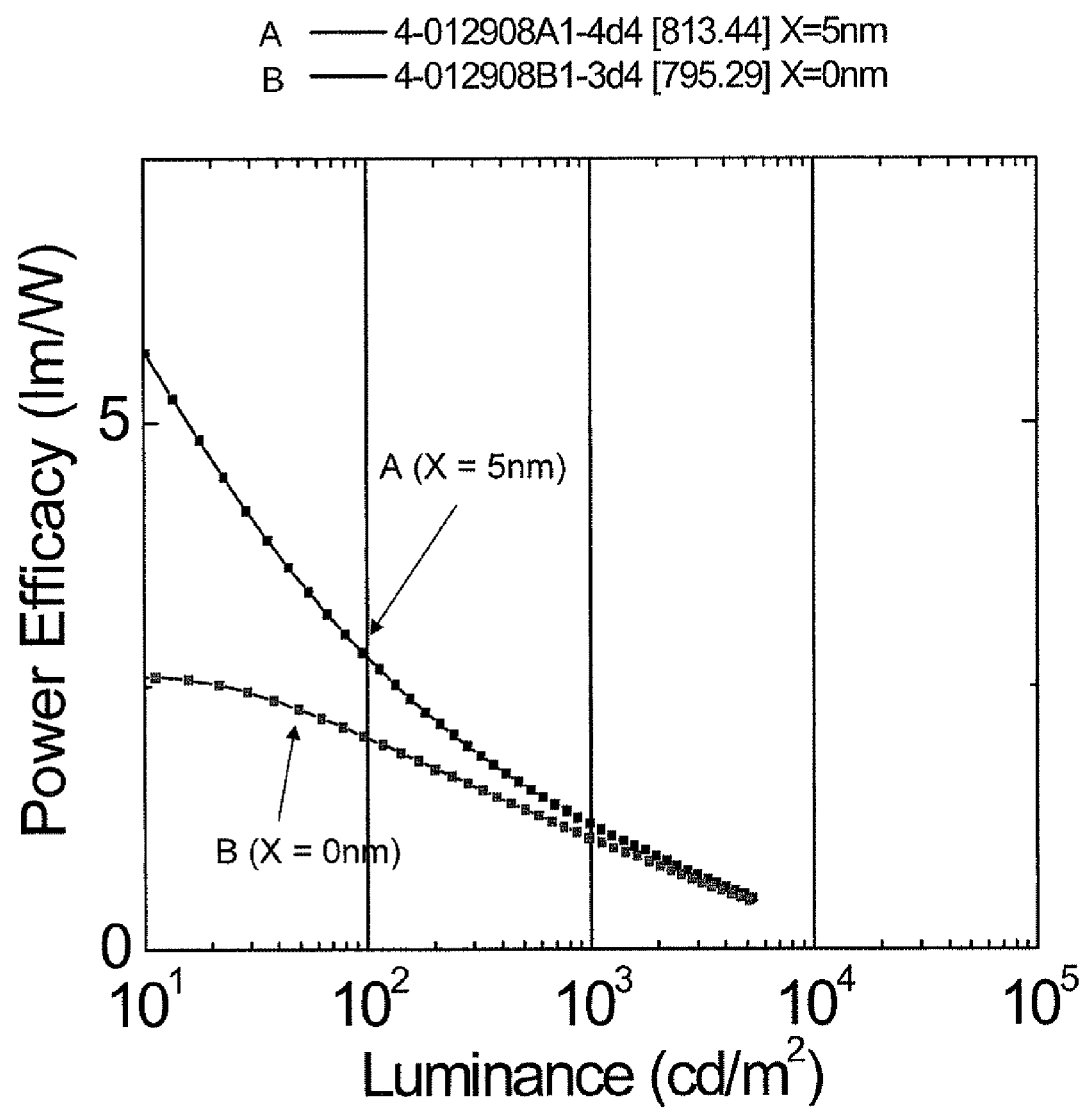
FIG. 72 shows the plot of power efficiency (Lm/W) versus luminance for the devices of Example 9.
Figure 73:
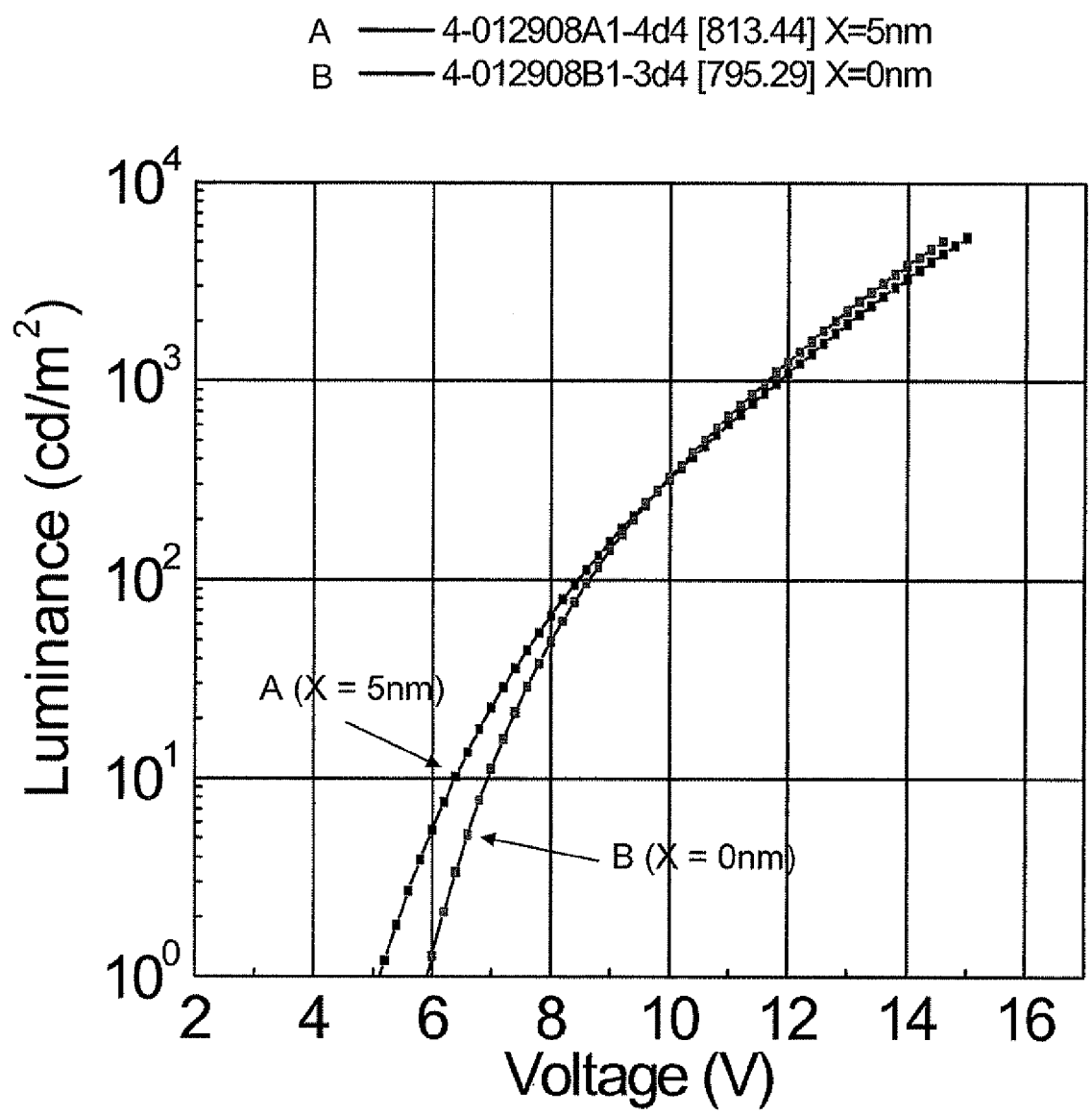
FIG. 73 shows the plot of luminance versus voltage for the devices of Example 9.
Figure 74:
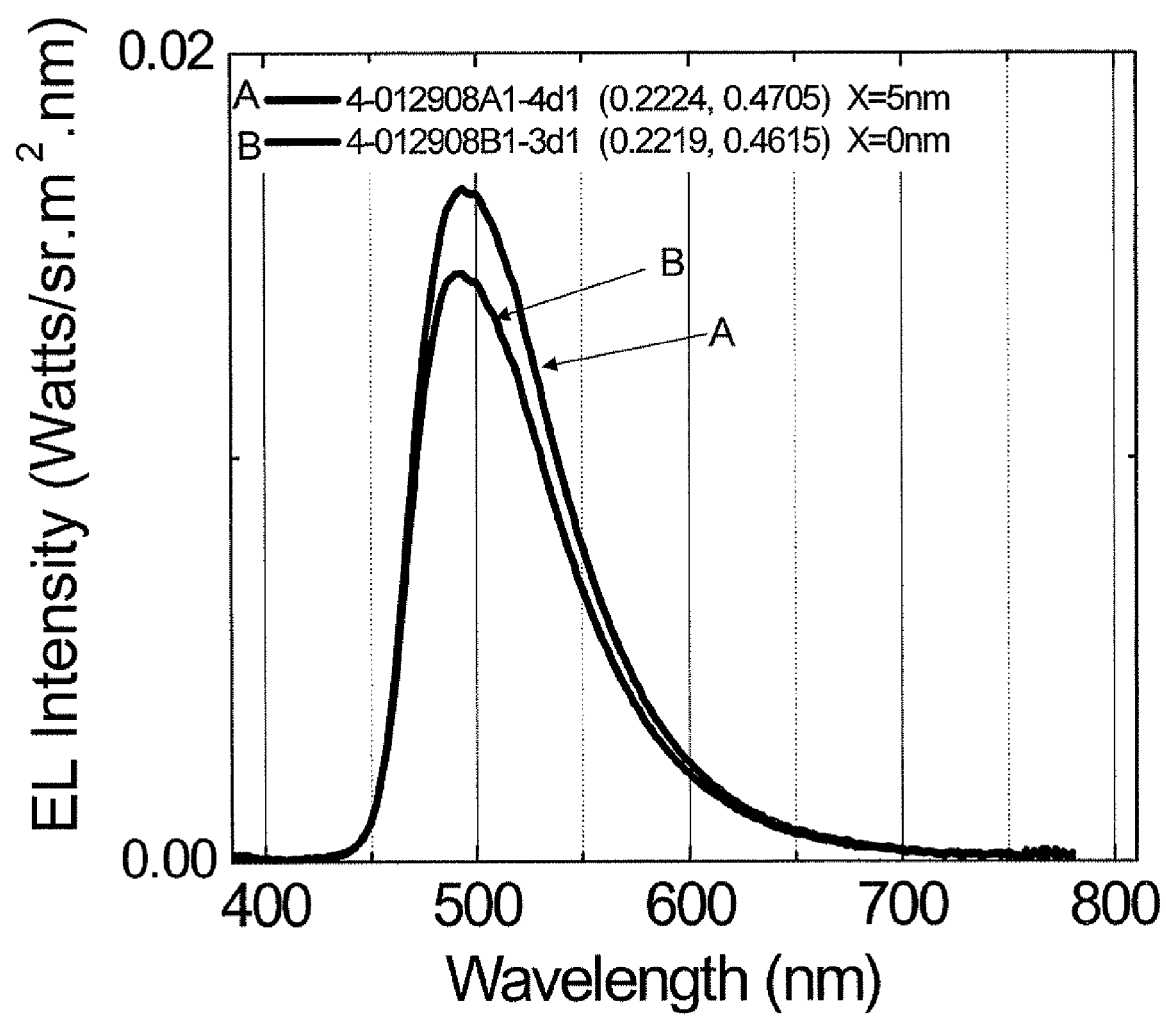
FIG. 74 shows the plot of EL intensity versus wavelength for the devices of Example 9.
Figure 75:
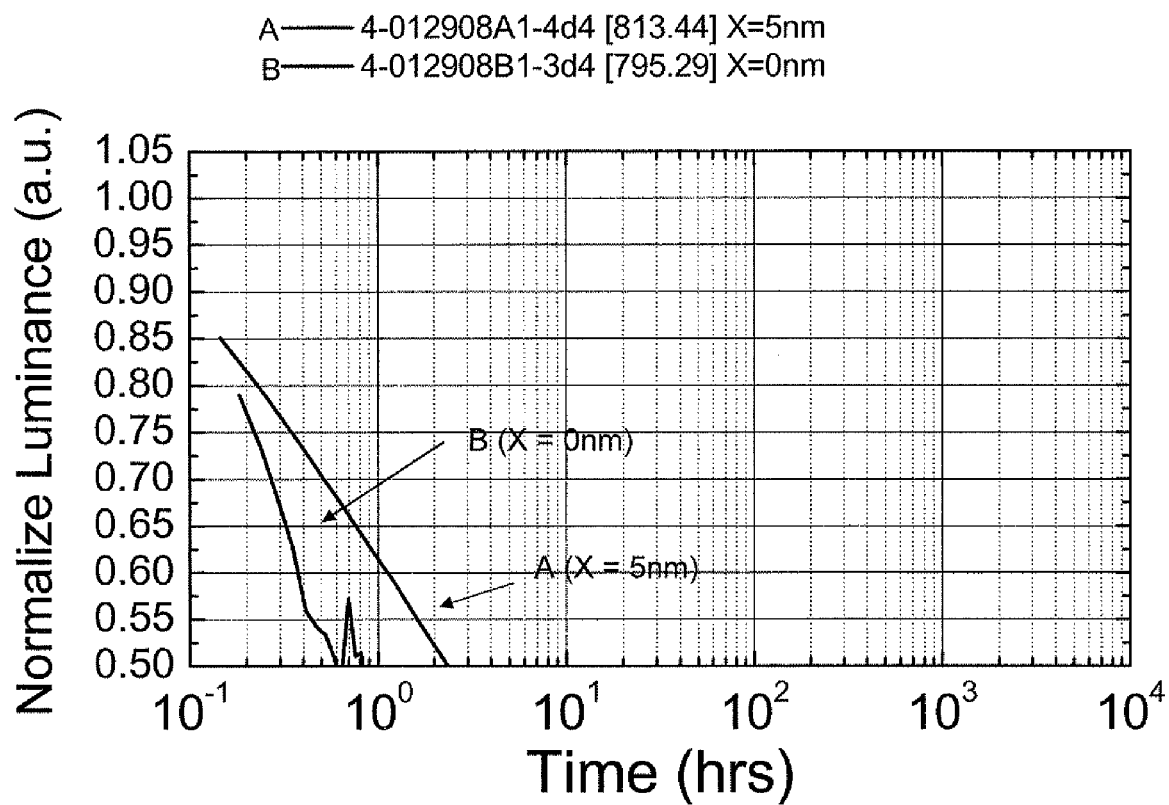
FIG. 75 shows the plot of the device lifetime at 1000 nits (normalized luminance versus time) for the devices of Example 9.

OLEDs comprising the phosphorescent emissive material from Example 7 (D356) according to the present invention was fabricated. The device structures are:

ITO (80 nm)/HIL4 (10 nm)/NPD (30 nm)/mCP: D356, 9% (30 nm)/mCP (X nm)/Alq$_3$ (40 nm)/LiF/Al. See FIG. 70. The device characteristics for these devices were measured and are set forth in FIGS. 71 to 75.

While the present invention is described with respect to particular examples and preferred embodiments, it is understood that the present invention is not limited to these examples and embodiments. The present invention as claimed therefore includes variations from the particular examples and preferred embodiments described herein, as will be apparent to one of skill in the art.

TABLE 2

| Device Name | Device Structure |
|---|---|
| A | CuPc(10 nm)/NPD(40 nm)/CBP:es-4, 6%(30 nm)/Alq$_3$(55 nm)/LiF/Al |
| B | CuPc(10 nm)/NPD(40 nm)/CBP:es-4, 9%(30 nm)/Alq$_3$(55 nm)/LiF/Al |
| C | CuPc(10 nm)/NPD(40 nm)/CBP:es-4, 12%(30 nm)/Alq$_3$(55 nm)/LiF/Al |
| D | CuPc(10 nm)/NPD(40 nm)/CBP:es-4, 9%(30 nm)/CBP(5 nm)/Alq$_3$(45 nm)/LiF/Al |
| E | CuPc(10 nm)/NPD(40 nm)/CBP:es-4, 9%(30 nm)/BAlq$_2$(10 nm)/Alq$_3$(45 nm)/LiF/Al |
| F | CuPc(10 nm)/NPD(40 nm)/CBP:es-4, 9%(30 nm)/HPT(10 nm)/Alq$_3$(45 nm)/LiF/Al |
| AA | CuPc(10 nm)/NPD(30 nm)/mCP:es-3, 6%(30 nm)/HPT(5 nm)/BAlq$_2$(40 nm)/LiF/Al |
| AB | CuPc(10 nm)/NPD(30 nm)/mCP:es-3, 12%(30 nm)/HPT(5 nm)/BAlq$_2$(40 nm)/LiF/Al |
| AC | CuPc(10 nm)/NPD(30 nm)/mCP:es-3, 3%(30 nm)/HPT(5 nm)/BAlq$_2$(40 nm)/LiF/Al |
| AD | CuPc(10 nm)/NPD(30 nm)/mCP:es-3, 9%(30 nm)/HPT(5 nm)/BAlq$_2$(40 nm)/LiF/Al |
| AE | CuPc(10 nm)/NPD(30 nm)/mCBP:es-3, 9%(30 nm)/HPT(5 nm)/BAlq$_2$(40 nm)/LiF/Al |
| AF | CuPc(10 nm)/NPD(30 nm)/mCBP:es-3, 12%(30 nm)/HPT(5 nm)/BAlq$_2$(40 nm)/LiF/Al |
| AG | CuPc(10 nm)/NPD(30 nm)/mCP:es-3, 9%(30 nm)/BAlq$_2$(40 nm)/LiF/Al |
| AH | CuPc(10 nm)/NPD(30 nm)/mCP:es-3, 9%(30 nm)/mCP(5 nm)/BAlq$_2$(40 nm)/LiF/Al |
| AI | CuPc(10 nm)/NPD(30 nm)/mCP:es-3, 9%(30 nm)/HPT(5 nm)/BAlq$_2$(40 nm)/LiF/Al |
| AJ | CuPc(10 nm)/NPD(30 nm)/mCP:es-3, 9%(30 nm)/mCP(5 nm)/HPT(10 nm)/BAlq$_2$(30 nm)/LiF/Al |
| AK | CuPc(10 nm)/NPD(30 nm)/mCP:es-3, 9%(30 nm)/mCBP(5 nm)/HPT(10 nm)/BAlq$_2$(30 nm)/LiF/Al |
| BA | CuPc(10 nm)/NPD(30 nm)/CBP:es-1, 6%(30 nm)/HPT(10 nm)/BAlq$_2$(40 nm)/LiF/Al |
| BB | CuPc(10 nm)/NPD(30 nm)/CBP:es-1, 6%(30 nm)/BAlq$_2$(40 nm)/LiF/Al |
| BC | CuPc(10 nm)/NPD(30 nm)/CBP:es-1, 12%(30 nm)/HPT(10 nm)/BAlq$_2$(40 nm)/LiF/Al |
| BD | CuPc(10 nm)/NPD(30 nm)/CBP:es-1, 12%(30 nm)/BAlq$_2$(40 nm)/LiF/Al |
| BE | CuPc(10 nm)/NPD(30 nm)/mCP:es-1, 6%(30 nm)/HPT(10 nm)/BAlq$_2$(40 nm)/LiF/Al |
| BF | CuPc(10 nm)/NPD(30 nm)/mCP:es-1, 6%(30 nm)/BAlq$_2$(40 nm)/LiF/Al |
| BG | CuPc(10 nm)/NPD(30 nm)/mCP:es-1, 12%(30 nm)/HPT(10 nm)/BAlq$_2$(40 nm)/LiF/Al |
| BH | CuPc(10 nm)/NPD(30 nm)/mCP:es-1, 12%(30 nm)/BAlq$_2$(40 nm)/LiF/Al |
| CA | HIL4(10 nm)/NPD(30 nm)/CBP:es-7, 6%(30 nm)/mCP(5 nm)/Alq$_3$(45 nm)/LiF/Al |
| CB | HIL4(10 nm)/NPD(30 nm)/CBP:es-7, 6%(30 nm)/HPT(5 nm)/Alq$_3$(45 nm)/LiF/Al |
| CC | HIL4(10 nm)/NPD(30 nm)/CBP:es-7, 6%(30 nm)/Alq$_3$(45 nm)/LiF/Al |
| CD | HIL4(10 nm)/NPD(30 nm)/CBP:es-7, 10%(30 nm)/mCP(5 nm)/Alq$_3$(45 nm)/LiF/Al |
| CE | HIL4(10 nm)/NPD(30 nm)/CBP:es-7, 10%(30 nm)/HPT(5 nm)/Alq$_3$(45 nm)/LiF/Al |
| CF | HIL4(10 nm)/NPD(30 nm)/CBP:es-7, 10%(30 nm)/Alq$_3$(45 nm)/LiF/Al |
| CG | HIL4(10 nm)/NPD(30 nm)/mCP:es-7, 6%(30 nm)/mCP(5 nm)/Alq$_3$(45 nm)/LiF/Al |
| CH | HIL4(10 nm)/NPD(30 nm)/mCP:es-7, 6%(30 nm)/HPT(5 nm)/Alq$_3$(45 nm)/LiF/Al |
| CI | HIL4(10 nm)/NPD(30 nm)/mCP:es-7, 6%(30 nm)/Alq$_3$(45 nm)/LiF/Al |
| CJ | HIL4(10 nm)/NPD(30 nm)/mCP:es-7, 10%(30 nm)/mCP(5 nm)/Alq$_3$(45 nm)/LiF/Al |
| CK | HIL4(10 nm)/NPD(30 nm)/mCP:es-7, 10%(30 nm)/HPT(5 nm)/Alq$_3$(45 nm)/LiF/Al |
| CL | HIL4(10 nm)/NPD(30 nm)/mCP:es-7, 10%(30 nm)/Alq$_3$(45 nm)/LiF/Al |
| DA | HIL4(10 nm)/NPD(30 nm)/CBP:es-8, 6%(30 nm)/HPT(5 nm)/Alq$_3$(45 nm)/LiF/Al |
| DB | HIL4(10 nm)/NPD(30 nm)/CBP:es-8, 10%(30 nm)/HPT(5 nm)/Alq$_3$(45 nm)/LiF/Al |
| DC | HIL4(10 nm)/NPD(30 nm)/DTB:es-8, 6%(30 nm)/DTB(10 nm)/Alq$_3$(40 nm)/LiF/Al |
| DD | HIL4(10 nm)/NPD(30 nm)/DTB:es-8, 6%(30 nm)/DTB(10 nm)/Alq$_3$(40 nm)/LiF/Al |
| AAA | CuPc(10 nm)/NPD(30 nm)/mCP:es-6, 9%(30 nm)/mCP(5 nm)/BAlq$_2$(40 nm)/LiF/Al |
| AAB | CuPc(10 nm)/NPD(30 nm)/mCP:es-6, 9%(30 nm)/BAlq$_2$(40 nm)/LiF/Al |

What is claimed is:
1. A compound, having a structure selected from:
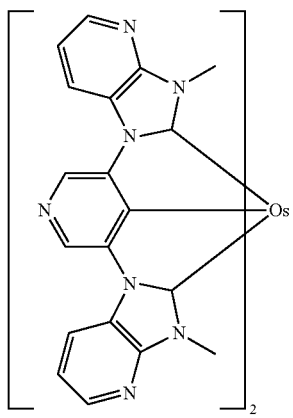 and
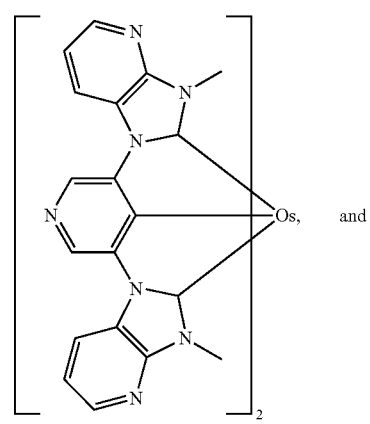 and
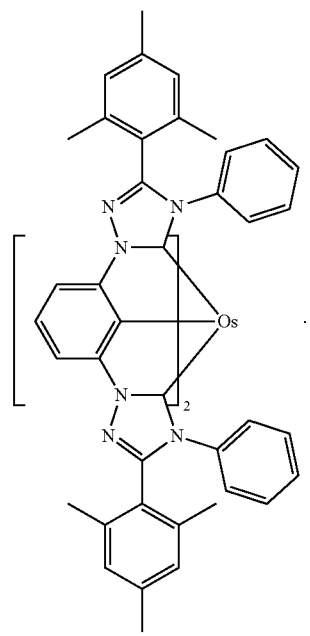
2. An organic light emitting device, comprising:
an anode;
a cathode; and
a phosphorescent emissive region disposed between the anode and the cathode, wherein the emissive material is selected from:
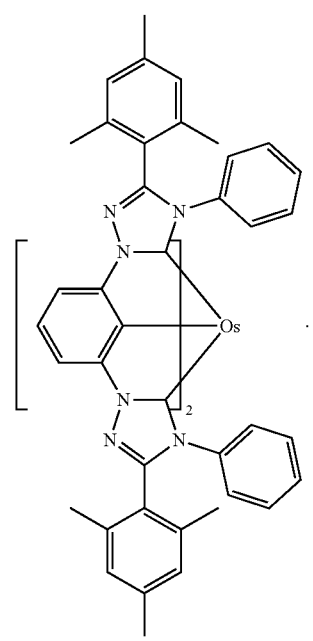
3. The organic light emitting device of claim 2, wherein the emissive material is
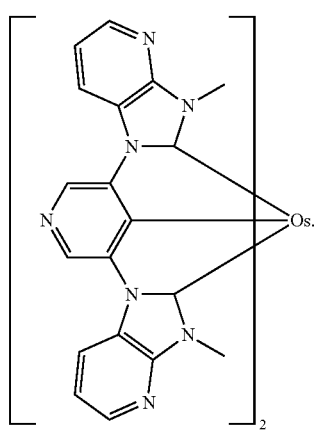

4. The organic light emitting device of claim 2, wherein the emissive material is
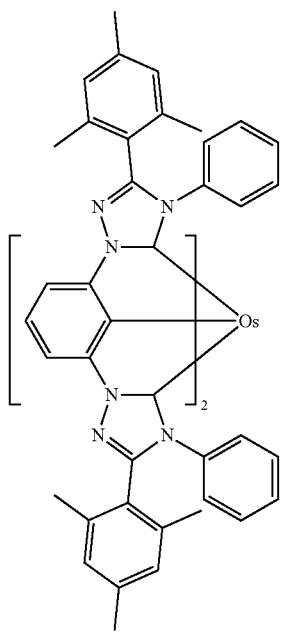
5. The compound of claim 1, having a structure:
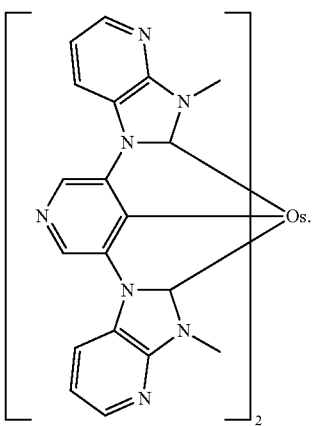
6. The compound of claim 1, having a structure:
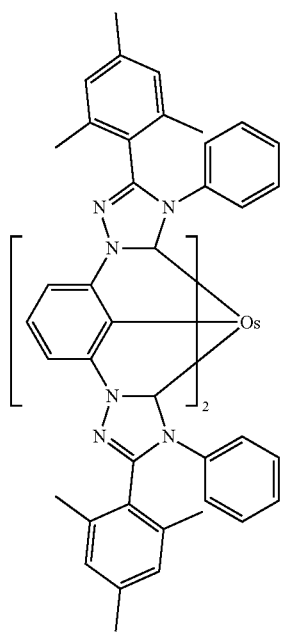
* * * * *